(12) United States Patent
Chye et al.

(10) Patent No.: US 7,256,327 B2
(45) Date of Patent: Aug. 14, 2007

(54) GENETICALLY MODIFIED PLANTS EXPRESSING PROTEINASE INHIBITORS, SAPIN2A OR SAPIN2B, AND METHODS OF USE THEREOF FOR THE INHIBITION OF TRYPSIN- AND CHYMOTRYPSIN-LIKE ACTIVITIES

(75) Inventors: Mee Len Chye, Hong Kong (CN); Zeng-Fu Xu, Guangzhou (CN); Suk-Fong Sin, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 216 days.

(21) Appl. No.: 10/725,829

(22) Filed: Dec. 1, 2003

(65) Prior Publication Data
US 2004/0205846 A1    Oct. 14, 2004

Related U.S. Application Data

(60) Provisional application No. 60/429,992, filed on Nov. 29, 2002.

(51) Int. Cl.
*A01H 5/00* (2006.01)
*C12N 15/82* (2006.01)
*C12N 15/29* (2006.01)

(52) U.S. Cl. ............... 800/302; 536/370; 800/279; 800/305; 435/320.1; 435/418; 424/93.2

(58) Field of Classification Search ............... 800/288; 435/184, 419, 468; 536/23.2
See application file for complete search history.

(56) References Cited

U.S. PATENT DOCUMENTS

| | | | |
|---|---|---|---|
| 4,376,110 | A | 3/1983 | David et al. |
| 4,946,778 | A | 8/1990 | Ladner et al. |
| 5,650,148 | A | 7/1997 | Gage et al. |
| 5,824,842 | A | 10/1998 | MacKay et al. |
| PP10,682 | P | 11/1998 | Plate |
| PP10,704 | P | 11/1998 | Lee |
| PP10,742 | P | 12/1998 | Bautista |
| 5,850,015 | A | 12/1998 | Bauer et al. |
| 5,869,720 | A | 2/1999 | John |
| 5,889,189 | A | 3/1999 | Rodriguez |
| 6,031,087 | A * | 2/2000 | Anderson et al. .......... 536/23.2 |
| 2003/0041353 | A1* | 2/2003 | Daniell et al. ............. 800/288 |
| 2004/0210966 | A1* | 10/2004 | Daniell et al. ............. 800/282 |

FOREIGN PATENT DOCUMENTS

WO    WO-01/42441 A2    6/2001

OTHER PUBLICATIONS

Zeng-Fu Xu et al., A Proteinase Inhibitor II of *Solanum americanum* is Expressed in Phloem, Plant Molecular Biology, 47:727-738, 2001.*

Johnson et al., Expression of Proteinase Inhibitors I and II in Transgenic Tobacco Plants: Effects on Natural Defense Against Manduca sexta larvae, Proceedings of the National Academy of Sciences of the United States of America, 86:9871-9875, 1989.*
Solomon et al., The Involvement of Cysteine Proteases and Protease Inhibitor Genes in The Regulation of Programmed Cell Death in Plants, The Plant Cell, 11:431-443.*
Zhang et al., Targeting a Nuclear Anthranilate Synthase Subunit Gene to the Tobacco Plastid Genome Results in Enhanced Tryptophan Biosynthesis. Return of a Gene to its Pre-Endosymbiotic Origin, Plant Physiology, 127:131-141, 2001.*
Urwin et al., Enhanced Transgenic Plant Resistance To Nematodes by Dual Proteinase Inhibitor Constructs, Planta, 204: 472-479, 1998.*
Hill et al., Functional Analysis of Conserved Histidines in ADP-Glucose Pyrophosphorylase From *Escherichia coli*, Biochemical and Biophysical Research Communications, 244:573-577, 1998.*
Lazar et al., Transforming Growth Factor: Mutation of Aspartic Acid 47 and Leucine 48 Results in Different Biological Activities, Molecular and Cellular Biology, 8:1247-1252, 1988.*
Guo et al., Protein Tolerance to Random Amino Acid Change, PNAS., 101:9205-9210, 2004.*
Wilson, 1997, In: Cellular and Molecular Biology of Plant Seed Development, Larkins et al, eds., p. 331-374.*
Johnson et al, 1989, Proc. Natl. Acad. Sci. USA 86:9871-9875.*
Graham et al, 1985, J. Biol. Chem. 260:6561-6564.*
Balandin et al., Plant Molecular Biology, vol. 27, pp. 1197-1204 (1995).
Thornburg et al., Proc. Natl. Acad. Sci. USA, vol. 84, pp. 744-748 (1987).
Sanchez-Serrano et al., Mol. Gen. Genet., vol. 203, pp. 15-20 (1986.
Gadea et al., Mol. Plant Microbe Interact, vol. 9, pp. 409-415 (1996).

(Continued)

*Primary Examiner*—Anne Kubelik
(74) *Attorney, Agent, or Firm*—Dickstein, Shapiro, LLP.

(57) ABSTRACT

The present invention relates to proteinase inhibitor II genes, SaPIN2a and SaPIN2b, their production in transformed plants, and isolation of SaPIN2a and SaPIN2b proteins from transformed plants of the invention. The invention further relates to use in inhibiting endogenous protease activities in transformed plants. In specific embodiments, the protease activities are trypsin-like and chymotrypsin-like activities. The invention relates to a method for protection of heterologous protein production in transformed plants by the co-expression of a proteinase inhibitor gene, e.g. SaPIN2a or SaPIN2b, which encodes a proteinase inhibitor protein, or a biologically active fragment, analog, and variant thereof, that inhibits protease activities. Specifically, the present invention also provides methods of inhibiting programmed cell death, including senescence, in plants. The invention further relates to methods to enhance resistance of plants to pests or pathogens, including insects. The present invention also relates to genetically modified plants, and in particular genetically modified lettuce. The genetically modified plants have inhibited endogenous trypsin-like and chymotrypsin-like activities following transformation of the plant with a vector comprising one or more proteinase inhibitor II gene, such as SaPIN2a and/or SaPIN2b. The invention further relates to transformed plants having enhanced resistance to insects. The invention further relates to transformed plants in which PCD or senescense is inhibited by transformation of plants using vectors of the present invention.

35 Claims, 21 Drawing Sheets

OTHER PUBLICATIONS

Figure 3:
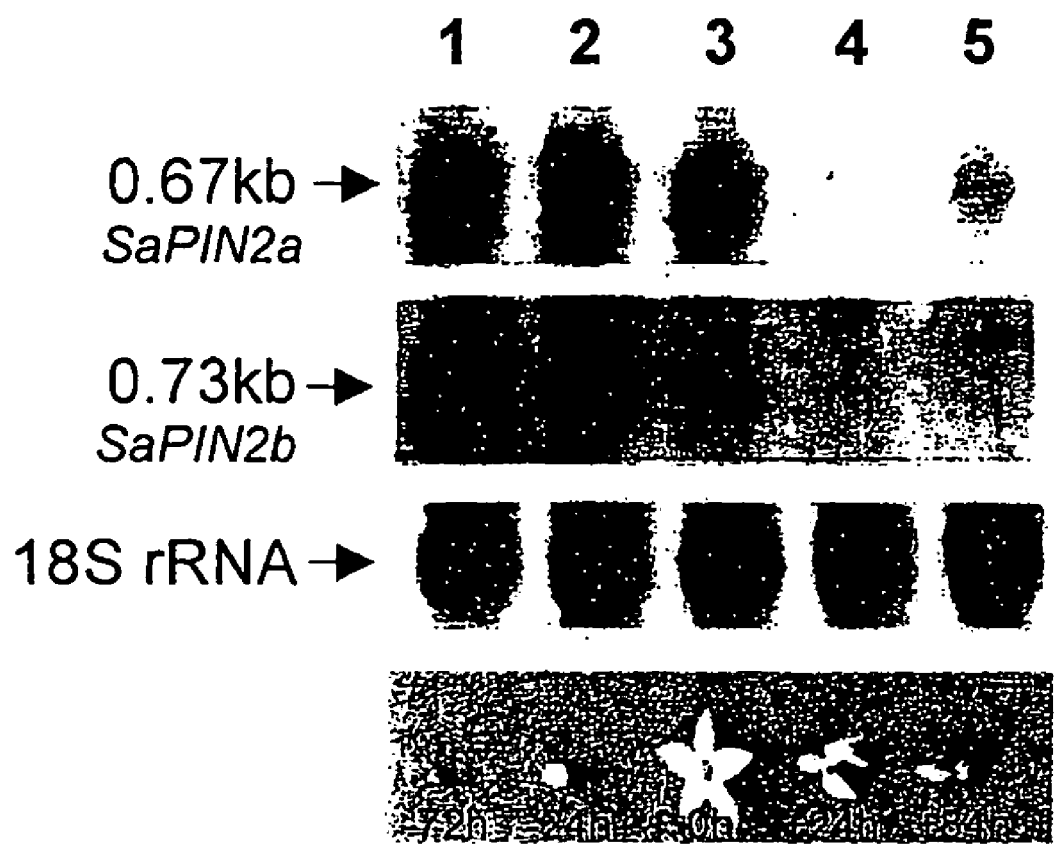

Instruction Manual of Nylon Membranes Optimized for Nucleic Acid Transfer by Amersham Biosciences, pp. 1-40 (2003).
Sambrook et al., A Laboratory Manual of Molecular Cloning, Cold Spring Harbor Laboratory Press, pp. 8.2 8.86 (1989).
Abstract of Nielson et al., Int. J. Neural System, vol. 8, Nos. 5-6, pp. 581-599 (1997).
Alfred Nisonoff, The Journal of Immunology, vol. 147, pp. 2429-2438 (1991).
Huang et al., Planta, vol. 191, pp. 256-264 (1993).
Hendriks et al., Plant Molecular Biology, vol. 17, pp. 385-394 (1991).
Gordon-Kamm et al., The Plant Cell, vol. 2, pp. 603-618 (1990).
Gatehouse et al., Molecular Breeding, vol. 3, pp. 49-63 (1997).
Abstract of Grimsley et al., Nature, vol. 325, pp. 177-179 (1987).
Abstract of C. Gatz, Methods Cell Biol., vol. 50, pp. 411-424 (1995).
Guerrero et al., Plant Molecular Biology, vol. 36, pp. 565-571 (1998).
Jean T. Greenberg, Proc. Natl. Acad. Sci, USA, vol. 93, pp. 12094-12097 (1996).
Ito et al., The Plant Cell, vol. 14, pp. 3201-3211 (2002).
Wu et al., Plant Molecular Biology, vol. 44, pp. 267-281 (2000).
Morrison et al., Proc. Natl. Acad. Sci. USA, vol. 81, pp. 6852-6855 (1984).
Ross et al., The Plant Journal, vol. 21, No. 6, pp. 547-552 (2000).
Margossian et al., Proc. Natl. Acad. Sci. USA, vol. 85, pp. 8012-8016 (1988).
Neuberger et al., Nature, vol. 312, pp. 604-608 (1984).
McNellis et al., The Plant Journal, vol. 14, No. 2, pp. 247-257 (1998).
Klopfenstein et al., Biomass and Bioenergy, vol. 12, pp. 299-311 (1997).
Abstract of Takamatsu et al., EMBO Journal, vol. 6, No. 2, pp. 307-311 (1987).
Abstract of Shimamoto et al., Nature, vol. 338, pp. 274-276 (1989).
Tamayo et al., Planta, vol. 211, pp. 62-71 (2000).
Abstract of Seymour et al., Plant Mol. Biol., vol. 23, No. 1, pp. 1-9 (1993).
Stevens et al., Plant Physiology, vol. 124, pp. 173-182 (2000).
Kolflpara et al., J. Agric. Food Chem., vol. 40, No. 12, pp. 2358-2363 (1992).
Abstract of Myers et al., Comput Appl. Biosci, vol. 4, No. 1., pp. 11-17 (1988).
Lee et al., Molecular Breeding, vol. 5, pp. 1-9 (1999).
Weinmann et al., The Plant Journal, vol. 5, No. 4, pp. 559-569 (1994).
Odell et al., Nature, vol. 313, pp. 810-812 (1985).
Kush et al., Proc. Natl. Acad. Sci., USA, vol. 87, pp. 1787-1790 (1990).
Outchkourov et al., Plant Physiology, vol. 133, pp. 379-390 (2003).
Kollipara et al., J. Agric. Food Chem., vol. 40, pp. 2356-2363 (1992).
U.K. Laemmli, Nature, vol. 227, pp. 680-685 (1970).
Abstract of Lund et al., Plant Mol. Biol., vol. 18, No. 1, pp. 47-53 (1992).
Abstract of Ward et al., Nature, vol. 341, pp. 544-546 (1989).
Clarence A. Ryan., BioEssays, vol. 10, pp. 20-24 (1989).
Lorberth et al., The Plant Journal, vol. 2, No. 4, pp. 477-486 (1992).
Morrison et al., Proc. Natl. Acad. Sci., USA, vol. 81, pp. 6851-6855 (1984).
Rosahl et al., Mol. Gen. Genet., vol. 202, pp. 368-373 (1986).
Reddy et al., Molecular Breeding, vol. 9, pp. 259-269 (2002).
Passelegue et al., Plant Science, vol. 113, pp. 79-89 (1996).
Pearce et al., Plant Physiol., vol. 102, pp. 639-644 (1993).
Valdes et al., Biochemical and Biophysical Research Communications, vol. 308, pp. 94-100 (2003).
Salinas et al., The Plant Cell, vol. 4, pp. 1485-1493 (1992).
Shilo et al., Proc. Nat'l Acad. Sci. USA, vol. 78, pp. 6789-6792 (1981).
Klein et al., Proceedings of the National Academy of Sciences of the United States of America, vol. 85, pp. 4305-4309 (1988).
Svab et al., Proc. Natl. Acad. Sc. USA, Vol. 90, pp. 913-917 (1993).
Abstract of Potrykus et al., Mol. Gen. Genet., vol. 199, pp. 169-177 (1985).
Pena-Cortes et al., The Plant Cell, vol. 3, pp. 963-972 (1991).
Jones et al., Plant Molecular Biology, vol. 28, pp. 505-512 (1995).
Chen et al., Plant Molecular Biology, vol. 35, pp. 821-831 (1997).
Chye et al., The Plant Journal, vol. 18, pp. 205-214 (1999).
Abstract of Coruzzi et al., EMBO, J., vol. 3, pp. 1671-1679 (1984).
Cordero et al., The Plant Journal, vol. 6, pp. 141-150 (1994).
Nielson et al., Protein Engineering, vol. 12, pp. 3-9 (1999).
Beers et al., Plant Molecular Biology, vol. 44, pp. 399-415 (2000).
Abstract of Jefferson et al., EMBO J., vol. 6, No. 13, pp. 3901-3907 (1987).
Janknecht et al., Proc. Natl. Acad. Sci. USA, vol. 88, pp. 8972-8976 (1991).
Abstract of Florack et al., Plant Mol. Biol., vol. 24, pp. 83-96 (1994).
Abstract of Curtis et al., Journal of Experimental Botany, vol. 45, pp. 1441-1449 (1994).
Abstract of Franck et al., Cell, vol. 21, pp. 285-294 (1980).
Abstract of Caddick et al., Nat. Biotechnol., vol. 16, pp. 177-180 (1998).
Johnson et al., Proc. Natl. Acad. Sci. USA, vol. 86, pp. 9871-9875 (1989).
Abstract of Huang et al., Planta et al., vol. 194, pp. 200-214 (1994).
Felton et al., "Antinutritive plant defence mechanisms", Biology of the Insect Midgut, published by Chapman & Hall, London, U.K. (1996).
Walker-Simmons et al., Plant Physiol., vol. 60, pp. 61-63 (1977).
Karlin et al., Proc. Natl. Acad. Sci. USA, vol. 87, pp. 2264-2268 (1990).
Daniell et al., TRENDS in Plant Science, vol. 7, pp. 84-91 (2002).
Daniell et al., TRENDS in Plant Science, vol. 6, pp. 219-226 (2001).
Duan et al., Nature Biotechnology, vol. 14, pp. 494-498 (1996).
Abstract of Dellaporta et al., Plant Molecular Biology Reporter, vol. 1, pp. 19-21 (1983).
Dominguez et al., The Plant Journal, vol. 15, pp. 569-574 (1998).
Fromm et al., Proc. Natl. Acad. Sci. USA, pp. 5824-5828 (1985).
Brzin et al., Biotechnology and Genetic Engineering Reviews, vol. 13, pp. 420-467 (1995).
Bryant et al., Biochemistry, vol. 15, pp. 3418-3423 (1976).
Brandstadter et al., Mol. Gen. Genet, vol. 252, pp. 146-154 (1996).
Pfitzner et al., Nucleic Acids Research, vol. 15, pp. 4449-4465 (1987).
Karlin et al., Proc. Natl. Acad. Sci. USA, vol. 90, pp. 5873-5877 (1993).
Hensel et al., The Plant Cell, vol. 5, pp. 553-564 (1993).
Greenspan et al., The FASEB Journal, vol. 7, pp. 437-444 (1993).
Michael Bevan, Nucleic Acids Research, vol. 12, pp. 8711-8721 (1984).
Boothe et al., Drug Development Research, vol. 42, pp. 172-181 (1997).
Altschul et al., Nucleic Acids Research, vol. 25, pp. 3389-3402 (1997).
Atkinson et al., The Plant Cell, vol. 5, pp. 203-213 (1993).
Huston et al., Proc. Natl. Acad. Sci. USA, vol. 85, pp. 5879-5883 (1988).
Brisson et al., Nature, vol. 310, pp. 511-513 (1984).
Abstract of Broglie et al, Science, vol. 224, pp. 838-843 (1984).
Hooykaas-Van Slogteren et al., Nature, vol. 311, pp. 763-764 (1984).
Abstract of Altschul et al., Journal of Molecular Biology, vol. 215, pp. 403-410 (1990).
Abstract of Applebaum et al., Journal of Insect Physiology, vol. 2, pp. 665-669 (1966).
Abstract of Bevan et al., Annu Rev Genet., vol. 16, pp. 357-384 (1982).
Abstract of Birk et al., Biochim Biophys Acta., vol. 67, pp. 326-328 (1963).
Marion M. Bradford, Analytical Biochemicstry, vol. 72, pp. 248-254 (1976).
Gustafson et al., The Journal of Biological Chemistry, vol. 251, pp. 7004-7010 (1976).

Computer Corner, "PSORT: a program for detecting sorting signals in proteins and predicting their subcellular localization", TIBS 24, pp. 34-35 (1999).

Hilder et al., "Transgenic plants conferring insect tolerance: protein-ance inhibitor approach", editors: Transgenic Plants. 1. Engineering and Utilization, San Diego: Academic Press, USA, pp. 317-338 (1993).

Reeck et al., "Proteinase inhibitors and resistance of transgenic plants to insects", editors: Advances in Insect Control: The Role of Transgenic Plants, Taylor and Francis, London, United Kingdom, pp. 157-183 (1997).

Angharad M.R. Gatehouse, "Biotechnological applications of plant genes in the production of insect resistant crops", editors: In Global Plant Genetic Resources for Insect Resistant Crops, SL Clement, SS Quisenberry, London, United Kingdom, pp. 263-280 (1998).

Cox et al., "Analysis of plant gene expression", editors: Plant molecular biology: a practical approach, Oxford: IRL Press, United Kingdom, pp. 1-34 (1988).

* cited by examiner

```
  1 CATAATGGCT GTTCACAAAG TTAGCTTCCT TGCTTGCCTA CTTGTTCTTG GATGGATGTT
 61 TCTACTTGCG AAACATGTTG ATGCCAAGGC TTGTACTAGA GAATGTGGTC ATTTTAGCTA
121 TGGCATATGC CCACGTTCAG AAGGAAGTCC CCAAAAACCT ATATGCACCA ATTGTTGCTC
181 AGGCTATAAG GGTTGCAACT ATTACAGTGC TAAAGGAGAT TTGATTTGTG AAGGAGAATC
241 TGACCCTAGA AACCCAAAAG ATTGTACCTT CGAATGTGAT ACACAGATTG CTTATTCAAA
301 ATGTCCTCGT TCAGAAGGAA AGATGATAAT TAAACCCACT GGATGCACCA CTTGTTGCAC
361 GGGCTATCAG GGTTGCTACT ATTTCGATCA AGATGGTGAT TTTGTCTGTG AAGGAGAGAG
421 TCCTGAACCC AAGACCACTG CTTATTTCTA ATCAATCATA TGTTGTTATC TATCAAAAAA
481 AAATATGTAT GCATGATATA TGCTGGTTAC TGTAATGTGG ACTTTATTG
```

FIG. 1a

```
  1   MAVHKVSFLA CLLVLGWMFL LAKHVDAKAC TRECGHFSYG ICPRSEGSPQ
 51   KPICTNCCSG YKGCNYYSAK GDLICEGESD PRNPKDCTFE CDTQIAYSKC
101   PRSEGKMIIK PTGCTTCCTG YQGCYYFDQD GDFVCEGESP EPKTTAYF
```

FIG. 1b

A SaPIN2b nucleotide sequence

```
  1 GAAGATAATT AATCACGATC GAGAAAGAAT AAATGGCTGT TCACAAAGAA
 51 GTTAGTTCCC TTGCTTACCT ACTTGTTCTT GGATTAATGT TTCTACATGT
101 AAGCGCGGTA AAACATGTTG ATGCCAAGCC ATGTACAAGA GAATGTGGTA
151 ATCTTGGGTA TGGAATATGC CCGCGTTCAG AAGGAAGTCC GGAAAATCCC
201 ATATGCACGA ATTGTTGCTC AGGCTATAAA GGTTGCAACT ATTATAGTGC
251 TAATGGGACT TTTATTTGCG AAGGAAGTTC TGACCCTAAA AACCCAAATA
301 CTTGCCCCTT ATTTTGTGAT GGAGATATTG CCTATTCAAA ATGTCCCCGT
351 TCAGAAGGAG AGACTATAAT ATATCCCACG GGATGCACCA CCTGTTGCAC
401 GGGGTACAAG GGTTGCTACT ATTTTAGTAA AGAAGGTGAG TTTGTGTGTG
451 AAGGAGAGAG TGATGAACCC AACGTTATTT CTAATCAATG AAATGCGTTG
501 TAGTTTTTAA TATAATGTAT GAAATAAAAG TATGCAGTAC GGCAATATAT
551 GATAATCACT ATAGTGTGGG CATCACAGTT GTGCTTTATA TGTAATTACT
601 AATTATCTGA ATAAGAGAAA AAGATCATCC ATGAGGACTT GGCTCCTCTC
651 CAGTAGTGGT GATCTCCTTC CTAAAAAAAA AAAAAAAAA AA
```

B SaPIN2b amino acid sequence

```
  1 MAVHKEVSSL AYLLVLGLMF LHVSAVKHVD AKPCTRECGN LGYGICPRSE
 51 GSPENPICTN CCSGYKGCNY YSANGTFICE GSSDPKNPNT CPLFCDGDIA
101 YSKCPRSEGE TIIYPTGCTT CCTGYKGCYY FSKEGEFVCE GESDEPNVIS
151 NQ
```

FIGS. 2a-b

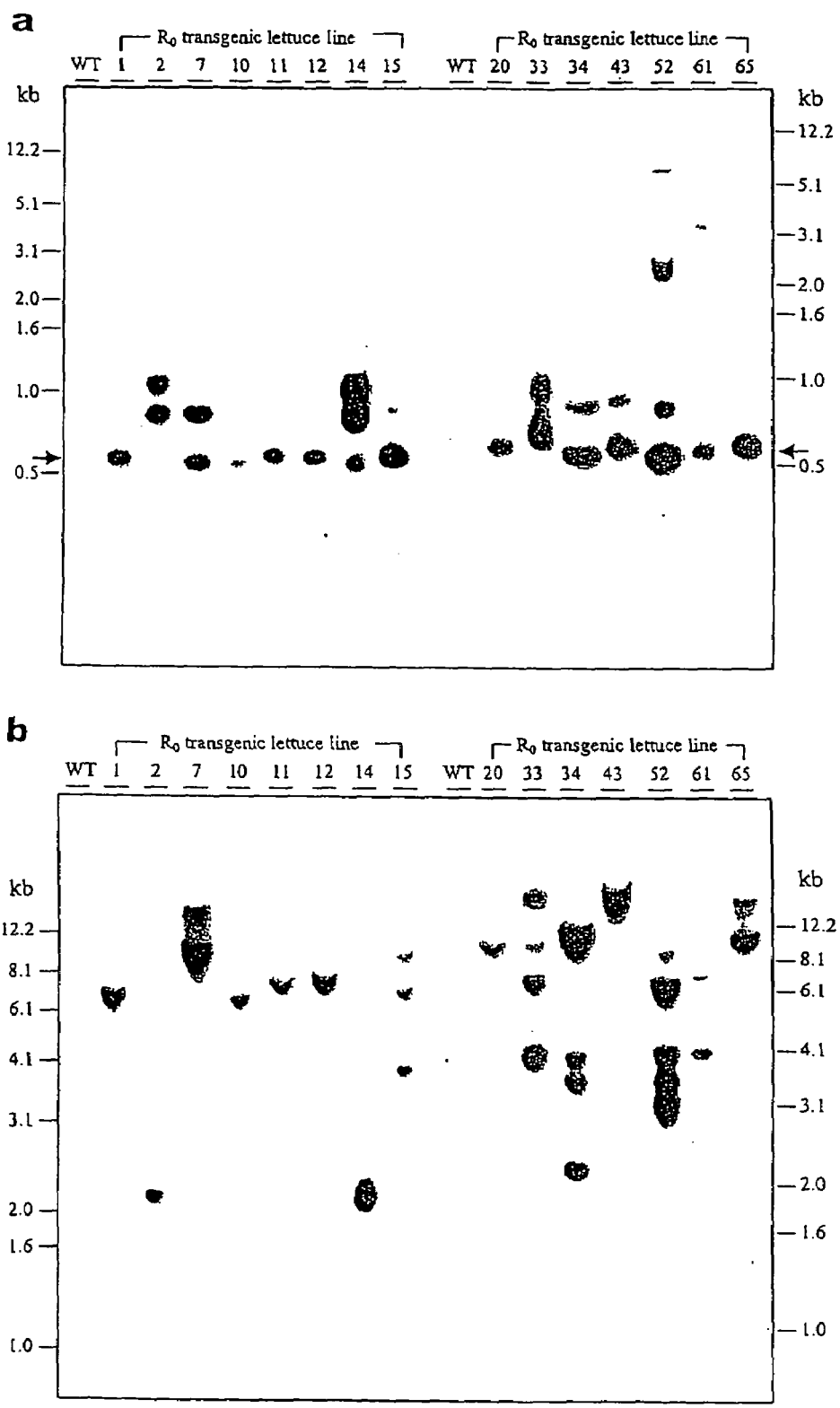
FIGS. 11a-b

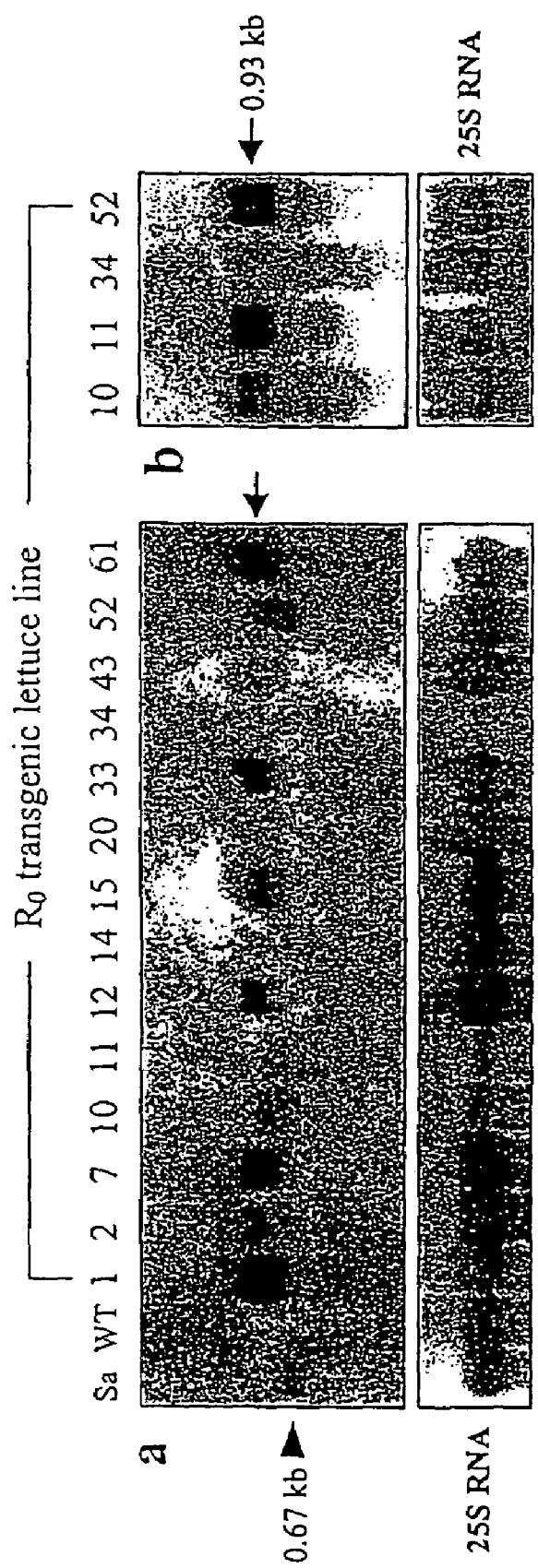
FIGS. 12a-b

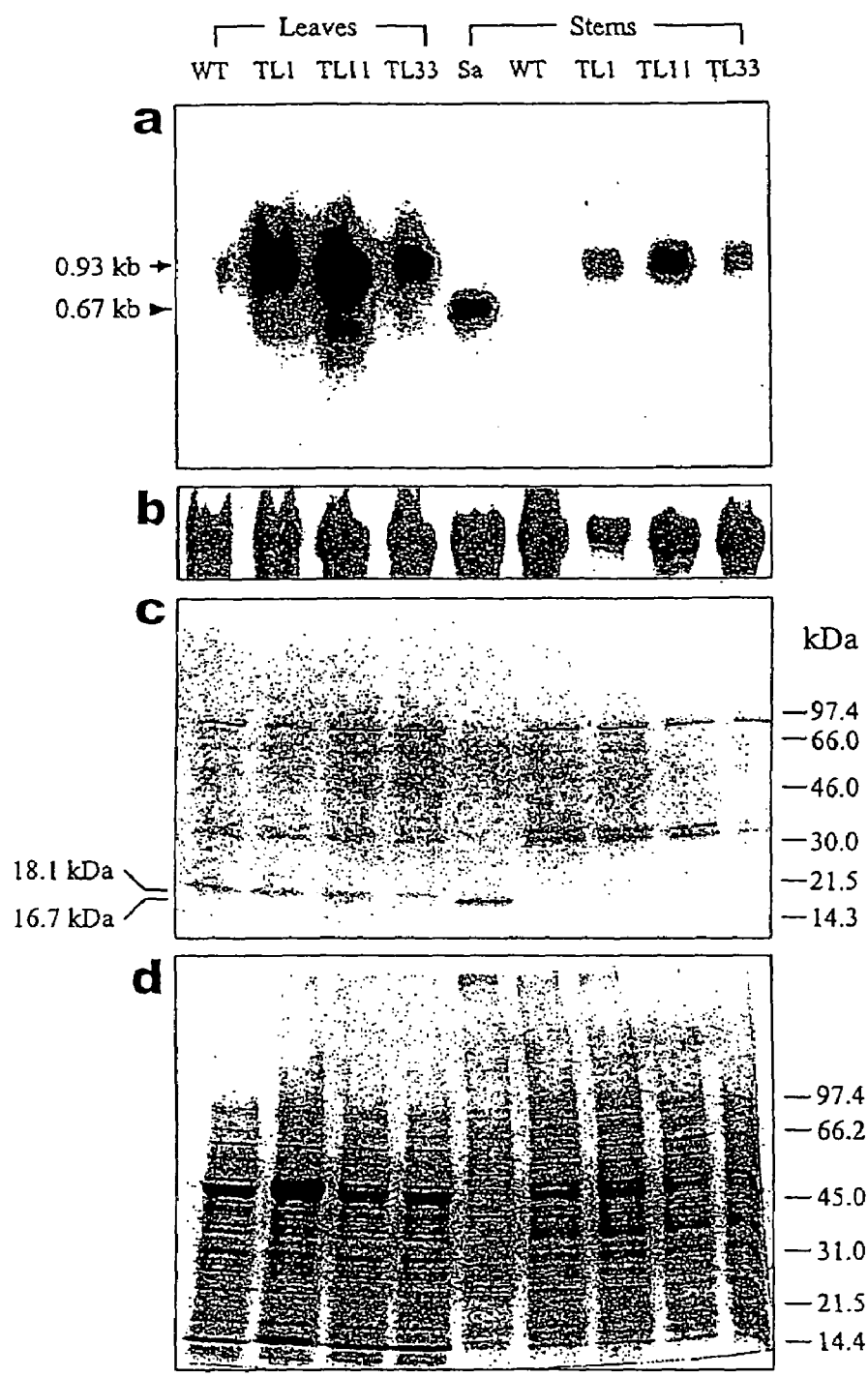
FIGS. 13a-d

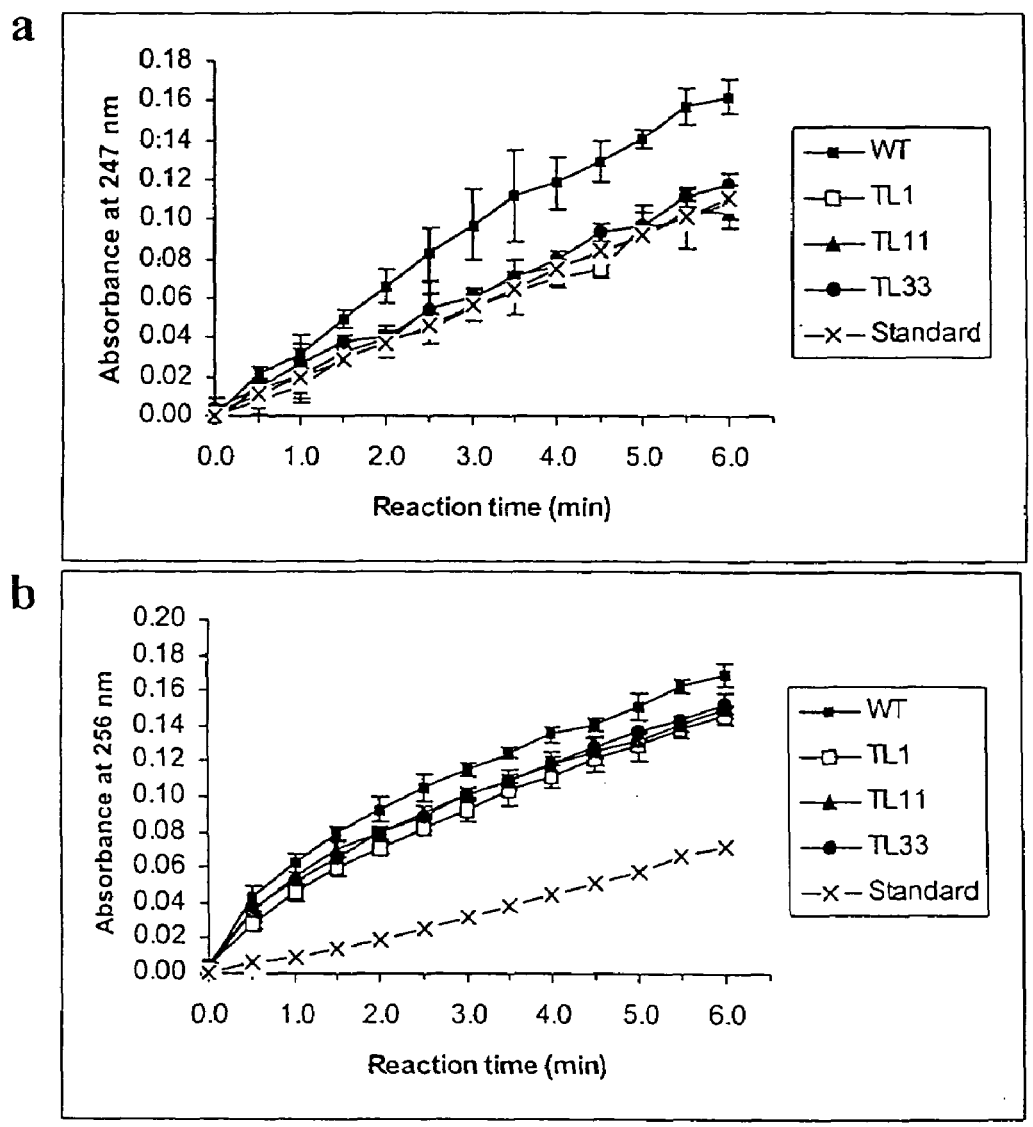
FIGS. 14a-b

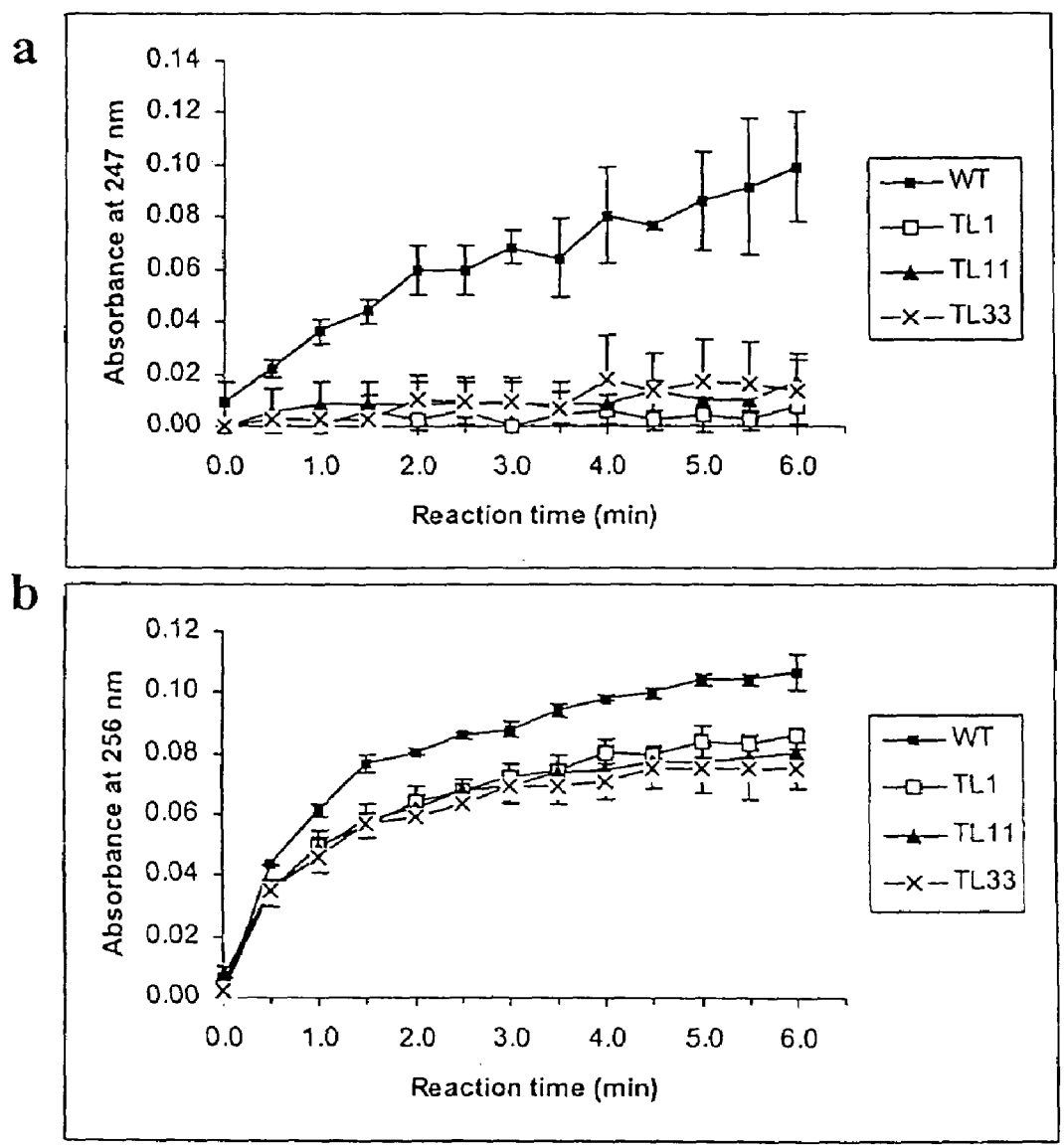
FIGS. 15a-b

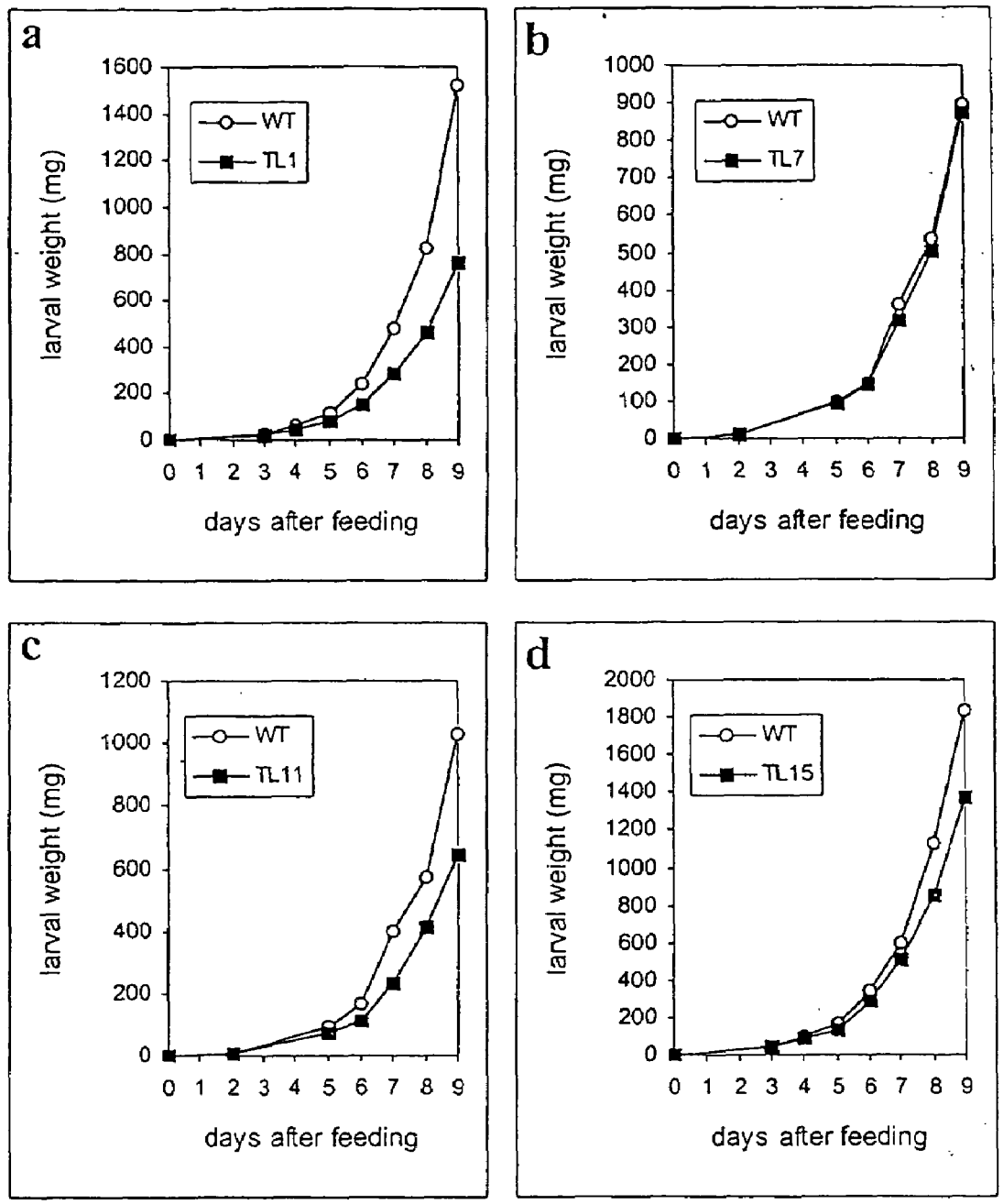
FIGS. 16a-d

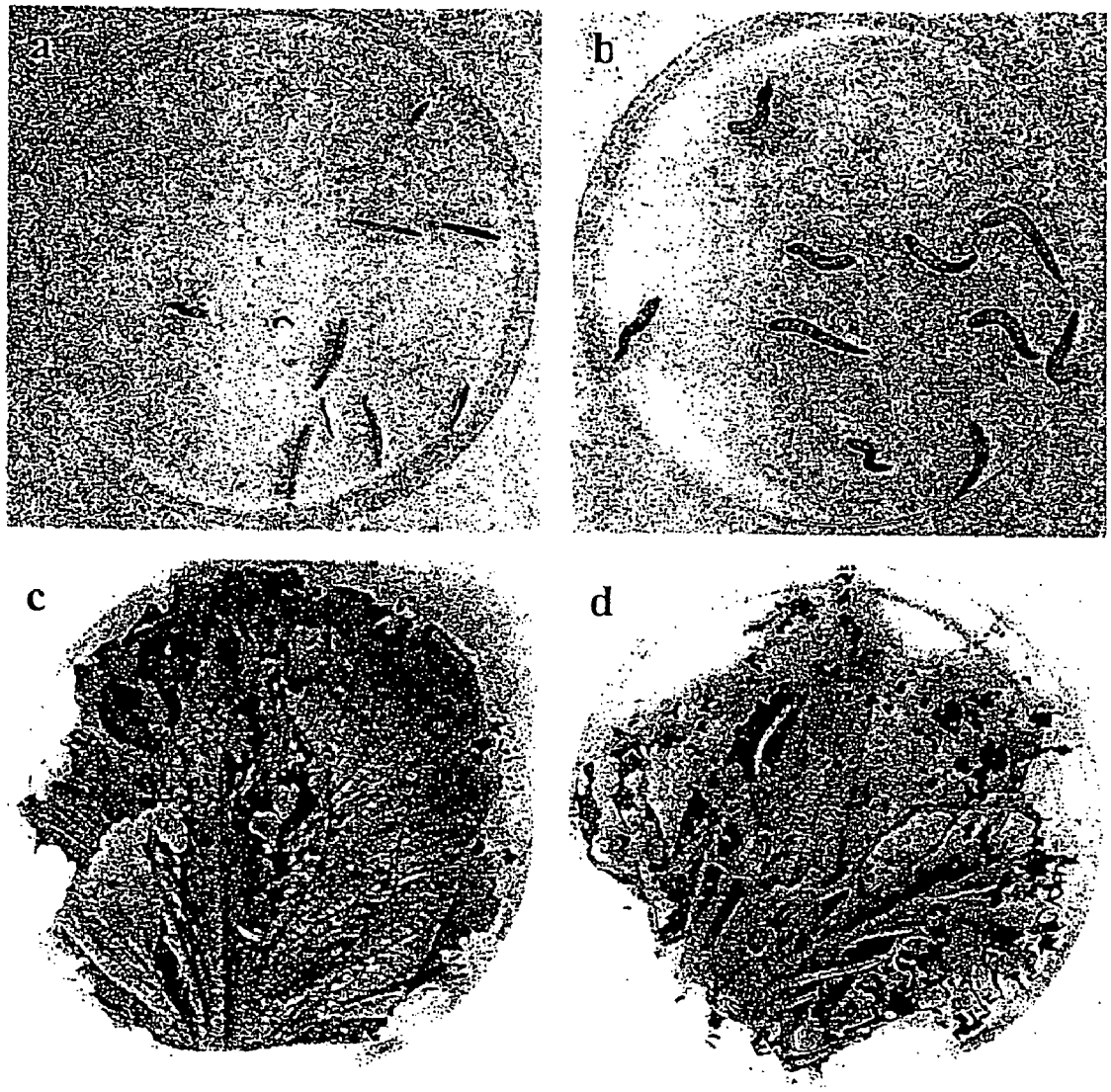
FIGS. 17a-d

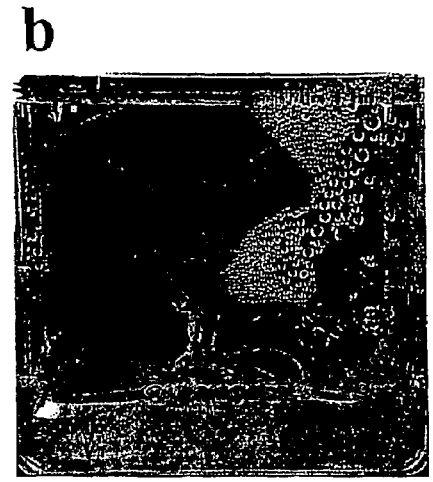
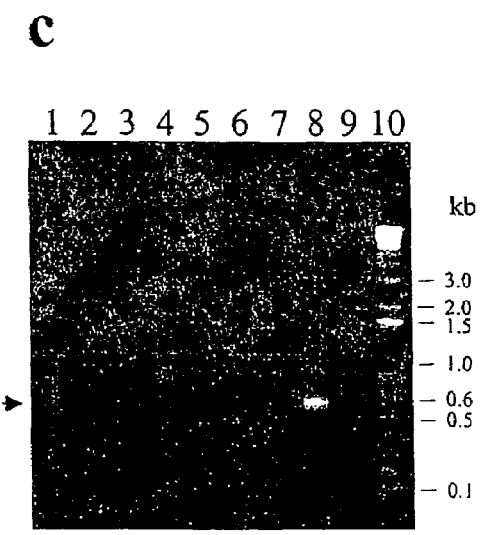
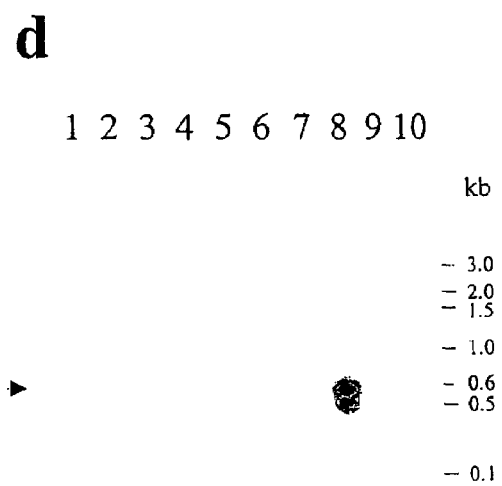
FIGs. 20a-d

GENETICALLY MODIFIED PLANTS EXPRESSING PROTEINASE INHIBITORS, SAPIN2A OR SAPIN2B, AND METHODS OF USE THEREOF FOR THE INHIBITION OF TRYPSIN- AND CHYMOTRYPSIN-LIKE ACTIVITIES

This application claims the benefit of U.S. Provisional Application No. 60/429,992, filed Nov. 29, 2002, which is incorporated by reference herein in its entirety.

1. FIELD OF INVENTION

The present invention relates to proteinase inhibitor II genes, SaPIN2a and SaPIN2b, and their use in inhibiting endogenous protease activities in transformed plants and in inhibiting exogenous protease activities in the preparation of plant-derived biopharmaceuticals. In specific embodiments, genetically modified plants comprising proteinase inhibitor II genes have inhibited endogenous protease activities. In specific embodiments, the protease activities are trypsin-like and chymotrypsin-like activities. The invention relates to a method for protection of heterologous protein production in transformed plants by the co-expression of a proteinase inhibitor gene, e.g., SaPIN2a or SaPIN2b, which encodes a proteinase inhibitor protein, or a biologically active fragment, analog, and variant thereof, that inhibits protease activities. The invention further relates to a method of inhibiting endogenous trypsin-like and chymotrypsin-like activities in a plant by expressing one or more proteinase inhibitor II genes. Specifically, the present invention also provides methods of inhibiting programmed cell death, including senescence, in plants and methods to enhance resistance of plants to pests or pathogens, including insects. The present invention also relates to genetically modified plants, and in particular genetically modified lettuce. The genetically modified plants have inhibited endogenous trypsin-like and chymotrypsin-like activities following transformation of the plant with a vector comprising one or more proteinase inhibitor II gene, such as SaPIN2a and/or SaPIN2b. In certain embodiments, genetically modified plants with high expression of a proteinase inhibitor II gene can be used to isolate proteinase inhibitor II protein. In a specific embodiment, the vector is introduced to a plant using *Agrobacterium*-mediated transformation or biolistics. The vector comprises a proteinase inhibitor II gene, SaPIN2a and/or SaPIN2b which encodes a proteinase inhibitor protein or a biologically active fragment, analog, or variant thereof. In a specific embodiment, the expression of the proteinase inhibitor II is driven by the CaMV 35S promoter in nuclear transformation or the psbA promoter in plastid transformation. The invention further relates to transformed plants having enhanced resistance to insects. In specific embodiments, the transformed plants have enhanced resistance to cabbage looper (*Trichoplusia ni*). The invention further relates to transformed plants in which programmed cell death (PCD) or senescense is inhibited by transformation of plants using vectors of the present invention.

2. BACKGROUND

Proteinase inhibitor II (PIN2) is a serine proteinase inhibitor protein with two reactive sites, one inhibiting chymotrypsin and the other, trypsin (Bryant et al., 1976, *Biochemistry* 15: 3418–3424). PIN2 proteins are found in many *Solanaceae* plants including tomato (Gustafson and Ryan, 1976, *J. Biol. Chem.* 251: 7004–7010), potato (Bryant et al., 1976, *Biochemistry* 15: 3418–3424) and tobacco (Pearce et al., 1993, *Plant Physiol*. 102: 639–644). PIN2 proteins are present in leaves, flowers (Atkinson et al., 1993, *Plant Cell* 5: 203–213; Pena-Cortes et al., 1991, *Plant Cell* 3: 963–972; Brandstater et al., 1996, *Mol. Gen. Genet.* 252: 146–154), fruits (Pearce et al., 1988, *Planta* 175: 527–531), stems (Xu et al., 2001, *Plant Mol. Biol.* 47: 727–738) and tubers (Bryant et al., 1976, *Biochemistry* 15: 3418–3424).

Previously, plant proteinase inhibitors (PIs) were not known to inhibit endogenous plant proteases but were thought to have specificities for animal or microbial enzymes (Ryan, 1981, In *The Biochemistry of Plants* Vol.6 (Marcus, A., ed.). New York: Academic Press, pp. 351–370). The role of plant proteinase inhibitor proteins in defense is supported by studies of artificial insect diets and in vitro inhibition assays on insect gut proteases using purified proteinase inhibitor proteins from various plants (Hilder et al., 1993, Transgenic plants conferring insect tolerance: proteinase inhibitor approach. In: S. Kung and R. Wu (Eds.), Transgenic Plants, Volume 1, Academic Press, New York, pp. 317–338; Felton and Gatehouse, 1996, Antinutritive plant defence mechanisms. In: M. J. Lehane and P. F. Billingsley (Eds.), Biology Of The Insect Midgut, Chapman and Hall, London, pp. 373–416; Reeck et al., 1997, Proteinase inhibitors and resistance of transgenic plants to insects. In: N. Carozzi and M. Koziel (Eds.), Advances In Insect Control: The Role of Transgenic Plants, Taylor and Francis, London, pp. 157–183; Gatehouse, 1999, Biotechnological applications of plant genes in the production of insect-resistant crops. In: S. L. Clement and S. S. Quisenberry (Eds.), Global Plant Genetic Resources For Insect-resistant Crops, CRC Press, Boca Raton, pp. 263–280). Hence, the function of plant proteinase inhibitors was thought to be in the prevention of invasion through inhibition of foreign proteolytic enzymes of pests or pathogens (Ryan, 1989, *BioEssays*, 10: 20–24; Brzin and Kidric, 1995, *Biotechnol. Genet. Eng. Rev.* 13: 420–467).

There have been reports on the developmental regulation and tissue-specific accumulation of plant PIs (Rosahl et al., 1986, *Mol. Gen. Genet.* 202: 368–373; Sanchez-Serrano et al., 1986, *Mol. Gen. Genet.* 203: 15–20; Margossian et al., 1988, *Proc Natl Acad Sci USA* 85(21):8012–8016; Hendriks et al., 1991, *Plant Mol. Biol.* 17: 385–394; Pena-Cortes et al., 1991, *Plant Cell*, 3, 963–972; Lorberth et al., 1992, *Plant J.* 2: 477–486; Xu et al., 2001, *Plant Mol. Biol.* 47: 727–738). Proteinase inhibitor II from *Solanum americanum* (SaPIN2a) is highly expressed in the phloem and has possible involvement in regulating proteolysis in the sieve elements (Xu et al., 2001, *Plant Mol. Biol.* 47: 727–738). The localization of SaPIN2a mRNA and protein to the companion cells and sieve elements suggests regulation of proteolysis in phloem development/function.

What is needed are methods and compositions for expressing proteinase inhibitor proteins SaPIN2a and SaPIN2b by heterologous expression in transformed plants (i) to inhibit activities of endogenous proteases, particularly trypsin- and chymotrypsin-like activities; (ii) to delay the onset of senescence and/or programmed cell death, and/or increase their resistance to pests; and (3) for high level expression of proteinase inhibitor proteins for their isolation.

3. SUMMARY

The present invention relates to proteinase inhibitor II genes, SaPIN2a and SaPIN2b, and is based, in part, on the isolation of cDNAs encoding SaPIN2a (SEQ ID NO:1) and SaPIN2b (SEQ ID NO:3) from a *Solanum americanum* cDNA library using a tomato proteinase inhibitor II (PIN2) cDNA as hybridization probe (Xu et al., 2001, *Plant Mol. Biol.* 47:727–738, which is incorporated by reference in its entirety) and the isolation of a complete-length SaPIN2b cDNA (SEQ ID NO:3) using SaPIN2b-specific primers to amplify total RNA from *S. americanum* by the present inventors. Accordingly, the present invention relates to nucleic acid molecules comprising nucleotide sequences of SEQ ID NO:1 and SEQ ID NO:3 and nucleic acid molecules comprising nucleotide sequences that encode SaPIN2a protein having an amino acid sequence of SEQ ID NO:2 or SaPIN2b protein having an amino acid sequence of SEQ ID NO:4. In another embodiment, the present invention relates to a nucleic acid molecule comprising a nucleotide sequence that hybridizes under stringent conditions to the complement of a nucleotide sequence of SEQ ID NO:1 or SEQ ID NO:3. By way of example and not limitation, high stringency hybridization conditions can be defined as follows: The filter-bound DNA were hybridized in a solution containing 50% deionized formamide, 6×SSC, 5× Denhardt's, 1% SDS, 100 µg/ml denatured salmon sperm DNA at 42° C. overnight (about 4–16 hours), and washing in 0.1×SSC, 0.1% SDS at 65° C. (Ausubel F. M. et al., eds., 1989, Current Protocols in Molecular Biology, Vol. I, Green Publishing Associates, Inc., and John Wiley & sons, Inc., New York). In specific embodiments, the nucleic acid molecule is a vector. In another embodiment, the present invention relates to fragments of proteinase inhibitor II nucleic acids which encode a proteinase inhibitor II protein, or a biologically active fragment, analog, or variant thereof, that specifically binds to and inhibits trypsin and/or chymotrypsin in plants. In a specific embodiment, the nucleic acid molecule comprises a minimal active fragment of proteinase inhibitor II.

The present invention further provides an isolated SaPIN2a polypeptide (SEQ ID NO:2), an isolated SaPIN2b polypeptide (SEQ ID NO:4), or a fragment, analog, or variant thereof, that has trypsin-like and chymotrypsin-like inhibitor activities. In another embodiment, the present invention provides isolated polypeptides having trypsin-like and chymotrypsin-like inhibitor activities that are encoded by a nucleic acid molecule comprising a nucleotide sequence of SEQ ID NO:1 or SEQ ID NO:3, or a fragment, analog, or variant thereof, or a nucleotide sequence that hybridizes under stringent conditions to the complement of a nucleotide sequence of SEQ ID NO:1 or SEQ ID NO:3, or a fragment, analog, or variant thereof.

The present invention further relates to the use of SaPIN2a and SaPIN2b genes in inhibiting proteinase activities in transformed plants and is based, in part, on the observation of the present inventors that SaPIN2a and SaPIN2b regulate senescence and programmed cell death (PCD) through inhibited endogenous proteinase activities in plants. In specific embodiments, the proteinase activities are trypsin-like and chymotrypsin-like activities. Expression of these genes late in floral development is useful in preventing senescence and PCD, thereby prolonging the shelf-life of commercially important plants and plant parts, e.g., flowers and fruits.

In a specific embodiment, the present invention further provides a method of protecting heterologous protein production in transformed plants by the co-expression of a proteinase inhibitor gene, e.g., SaPIN2a or SaPIN2b, which encodes a proteinase inhibitor protein, or a biologically active fragment, analog or variant thereof, that inhibits proteinase activity. In a specific embodiment, the plant is a transformed plant that expresses a heterologous protein. The method comprises the steps of introducing into the plant nuclear or plastid genome a nucleic acid sequence encoding a proteinase inhibitor II and a heterologous gene and generating a plant having an altered genome. The heterologous gene may be expressed from a separate vector from the vector encoding the proteinase inhibitor. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator.

In a specific embodiment, the present invention further provides a method of inhibiting endogenous proteinase activity in plant. The method comprises the steps of introducing into the plant nuclear or plastid genome a nucleic acid sequence encoding a proteinase inhibitor II and generating a plant having an altered genome. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator.

In a specific embodiment, the present invention further provides a method of inhibiting endogenous trypsin-like activity in plant. The method comprises the steps of introducing into the plant nuclear or plastid genome a nucleic acid sequence encoding a proteinase inhibitor II and generating a plant having an altered genome. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator.

In a specific embodiment, the present invention further provides a method of inhibiting endogenous chymotrypsin-like activity in plant. The method comprises the steps of introducing into the plant nuclear or plastid genome a nucleic acid sequence encoding a proteinase inhibitor II and generating a plant having an altered genome. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator.

In a specific embodiment, the present invention further provides a method of preventing programmed cell death or senescence in plants. The method comprises the steps of introducing into the plant nuclear or plastid genome a nucleic acid sequence encoding a proteinase inhibitor II and generating a plant having an altered genome. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator. In a preferred embodiment, the promoter expresses the proteinase inhibitor II late in floral development. Assays useful for detecting PCD include the TUNEL assay.

In a specific embodiment, the present invention further provides a method of enhancing the resistance of plant to pests or pathogens. The method comprises the steps of introducing into the plant nuclear or plastid genome a nucleic acid sequence encoding a proteinase inhibitor II and generating a plant having an altered genome. In a specific embodiment, the proteinase inhibitor II gene is from *Solanum americanum*. In another specific embodiment, the proteinase inhibitor II gene is SaPIN2a or SaPIN2b, under the direction of a suitable promoter and a suitable terminator. In specific embodiment, the pest is cabbage looper. In another specific embodiment, the cabbage looper is *Trichoplusia ni*.

In a specific embodiment, the present invention further provides methods for the isolation of proteinase inhibitor II proteins from transformed plant cells. These proteins when expressed in transformed plants, particularly in transplastomic plants as tagged proteins (e.g., His-tagged proteins by using a plasmid such as pMLVHisP), can easily be extracted and purified for exogenous applicaitons to protect proteins from degradation.

The present invention is further based on the observation of the present inventors that when SaPIN2a is expressed in transgenic lettuce, it results in the inhibition of plant endogenous protease activity. Lettuce was chosen for expression of SaPIN2a because it neither possesses detectable trypsin inhibitory activity in its leaves nor responds to any treatments by accumulating inhibitors (Walker-Simmons and Ryan, 1977, *Plant Physiol.* 59: 437–439). Further, lettuce is an economically important vegetable crop, grown globally (Ryder, 1999, *Lettuce, endive and chicory*. New York: CABI Publishing) and its transformation methods are available (Michelmore et al., 1987, *Plant Cell Rep.* 6: 439–442; Curtis et al., 1994, *J. Exp. Bot.* 45: 1441–1449). The methods of the present invention are equally applicable to plants other than lettuce such as tomatoes, ginger, scallions, water chestnuts, pepper and eggplant; leafy plants, including lettuce and spinach; *Brassicas*, including broccoli, brussels sprouts, calabrese, kale, cauliflower, red cabbage and white cabbage; cucurbits, including cucumber, melon, watermelon, zucchini and squash; large seeded plants, including peas, beans and sweetcorn; rooted plants, including carrots and onions; vegetatively propagated plants, including berries, grapes, banana, pineapple and rosaceous fruit and nut crops; and tropical crops, including tobacco, mango and papaya.

The invention seeks to provide inhibition of endogenous protease activity in plants by transforming plants, such as crops, and specifically lettuce, with proteinase inhibitor II using nuclear or plastid transformation. In a specific embodiment, the invention provides transgenic lettuce with enhanced inhibition of endogenous trypsin-like activity by the expression of proteinase inhibitor II from *Solanum americanum* (SaPIN2a or SaPIN2b). In a specific embodiment, the inhibition is complete, i.e., more than about 90% and less than or equal to 100%. In a specific embodiment, the inhibition is moderate, i.e, more than about 50% and less than about 90%. In a specific embodiment, the inhibition is low, i.e., more than 5% and less than about 50%. In specific embodiments, the inhibition is at least 5%, 10%, 15%, 20%, 25%, 30%, 40%, 45%, 50%, 55%, 60%, 65%, 70%, 75%, 80%, 85%, 90% or 95%. The percentage inhibition may be determined by any assays well known to one skilled in the art. Inhibition of endogenous protease activity is compared to the endogenous protease activity without the exogenous proteinase inhibitor as the baseline.

The invention seeks to provide inhibition of endogenous trypsin-like activity in plants by transforming plants, such as crops, and specifically lettuce, with proteinase inhibitor II. In a specific embodiment, the invention provides transgenic lettuce with enhanced inhibition of endogenous trypsin-like activity by the expression of proteinase inhibitor II from *Solanum americanum* (SaPIN2a and/or SaPIN2b).

The invention seeks to provide inhibition of endogenous chymotrypsin-like activity in plants by transforming plants, such as crops, and specifically lettuce, with proteinase inhibitor II. In a specific embodiment, the invention provides transgenic lettuce with enhanced inhibition of endogenous chymotrypsin-like activity by the expression of proteinase inhibitor II from *Solanum americanum* (SaPIN2a and/or SaPIN2b).

The invention seeks to provide pests and pathogen protection in plants by transforming plants, such as crops, and specifically lettuce, with proteinase inhibitor II. In a specific embodiment, the invention provides transgenic lettuce with enhanced protection against cabbage looper by the expression of proteinase inhibitor II from *Solanum americanum* (SaPIN2a and/or SaPIN2b).

The present invention provides transformed plants having therein a gene comprising a promoter, operably associated with a coding sequence for SaPIN2a and/or SaPIN2b and a terminator. Plant cells containing a gene comprising a nucleic acid sequence encoding proteinase inhibitor II are also an aspect of this invention, as are other plant parts, such as for example, seeds of the transformed plant containing a gene according to the invention.

In a specific embodiment, the present invention provides transgenic lettuce having therein a gene comprising a promoter, operably associated with a coding sequence for SaPIN2a and/or SaPIN2b, and a terminator. Lettuce plant cells containing a gene comprising a nucleic acid sequence encoding SaPIN2a or SaPIN2b are also an aspect of this invention, as are other plant parts, such as for example, seeds of the transformed plant containing a gene according to the invention.

In a specific embodiment, the genetically modified plants have inhibited endogenous protease activity following the introduction, by recombinant DNA techniques, of vectors comprising coding sequences for proteinase inhibitor II, SaPIN2a or SaPIN2b, or a biologically active fragment, analog, or variant thereof. In a specific embodiment, lettuce is transformed via *Agrobacterium*-mediated transformation. In a specific embodiment, the expression of the proteinase inhibitor II is driven by the CaMV 35S promoter.

In a specific embodiment, the genetically modified plants have inhibited trypsin-like activity following the introduction, by recombinant DNA techniques, of coding sequences for proteinase inhibitor II. In a specific embodiment, lettuce is transformed via *Agrobacterium*-mediated transformation.

In a specific embodiment, the genetically modified plants have inhibited chymotrypsin-like activity following the introduction, by recombinant DNA techniques, of coding sequences for proteinase inhibitor II. In a specific embodiment, lettuce is transformed via *Agrobacterium*-mediated transformation.

In a specific embodiment, the genetically modified plants have enhanced resistance to cabbage looper, *Trichoplusia ni* following the introduction, by recombinant DNA techniques, of coding sequences for proteinase inhibitor II. In a specific embodiment, lettuce is transformed via *Agrobacterium*-mediated transformation.

In a specific embodiment, the invention relates to genetically modified plants in which programmed cell death or senescence is inhibited.

In another embodiment, additional gene sequences coding for proteinase inhibitors may be introduced into the plant in addition to the coding protein for proteinase inhibitor II. Such proteins includes, but are not limited to, genes encoding ribosome-inactivating proteins, lectins, agglutinins, and other pathogenesis-related proteins. In a specific embodiment, additional serine proteinase inhibitors other than SaPIN2a and SaPIN2b may be used.

3.1 Definitions

As used herein, a "proteinase inhibitor II gene" is a nucleic acid molecule comprising a nucleic acid sequence of SaPIN2a or SaPIN2b or fragments thereof. The fragments may be 25, 50, 100, 200, 300, 400, 500 or 600 nucleotides in length, or multiples thereof, which hybridize to nucleic acid sequences of SEQ ID NO:1 or SEQ ID NO:3 and have trypsin-like and chymotrypsin-like inhibitory activities.

As used herein, a "proteinase inhibitor II protein" is a polypeptide encoded by a proteinase inhibitor II gene. The protein may be a biologically active fragment, analog, or variant thereof of SaPIN2a or SaPIN2b. Generally, a proteinase inhibitor II protein has two or more inhibitory domains, each of which corresponds to a specific protease inhibitor activity. For example, SaPIN2a and SaPIN2b each contain an inhibitory domain 1 and an inhibitory domain 2 which correspond to a trypsin-inhibitor domain and a chymotrypsin-inhibitory domain, respectively. Thus, a biologically active fragment of a proteinase inhibitor protein includes fragments corresponding to an inhibitory domain and biologically active portions thereof. The inhibitory domain may be a trypsin inhibitory domain or a chymotrypsin inhibitory domain. A minimal active fragment of SaPIN2a or SaPIN2b corresponds to 54 amino acids. The trypsin inhibitory domain and chymotrypsin inhibitory domain of SaPIN2a corresponds to amino acids 30–83 and 87–140, respectively, while the trypsin inhibitory domain and chymotrypsin inhibitory domian of SaPIN2b corresponds to amino acids 34–87 and 91–144, respectively. The sequences of these amino acids are provided in SEQ ID NO:2 (SaPIN2a) and SEQ ID NO:4 (SaPIN2b).

As used herein, the term "variant" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "variant" as used herein also refers to a proteinaceous agent which has been modified, i.e., by the covalent attachment of any type of molecule to the proteinaceous agent. For example, but not by way of limitation, a protein may be modified, e.g., by glycosylation, acetylation, pegylation, phosphorylation, amidation, derivatization by known protecting/blocking groups, proteolytic cleavage, linkage to a cellular ligand or other protein, etc. A variant of a proteinaceous agent may be produced by chemical modifications using techniques known to those of skill in the art, including, but not limited to specific chemical cleavage, acetylation, formylation, metabolic synthesis of tunicamycin, etc. Further, a variant of a proteinaceous agent may contain one or more non-classical amino acids. A variant of a proteinaceous agent possesses a similar or identical function as the proteinaceous agent from which it was derived. Variants also encompasses precursor proteins from which a protein sequence is derived. Variants also encompasses fragments of full-length proteins that are, for example, 5, 10, 15, 20, 25, 30, 35, 40, 45, 50, 55, 60, 65, 70, 75, 80, 85, 90, 95, 100, or multiples thereof, or more contiguous amino acids of the full-length protein.

As used herein, the term "analog" in the context of a proteinaceous agent (e.g., proteins, polypeptides, peptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264–2268, modified as in Karlin and Altschul, 1993, *Proc. Natl. Acad. Sci. USA* 90:5873–5877. Such an algorithm is incorporated into the NBLAST and XBLAST programs of Altschul et al., 1990, *J. Mol. Biol.* 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucl. Acids. Res.* 25:3389–3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, *Comput. Appl. Biosci.* 4:11–17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, "trypsin-like activity" and "chymotrypsin-like activity" refers to an endogenous proteinase activity as measured in the assays described in the Examples, Section 6.1 under the section entitled "Trypsin and chymotrypsin inhibitory activity and endogenous trypsin- and chymotrypsin-like activity assays".

As used herein, "inhibited endogenous proteinase activity" or "inhibited protease activity" refers to a 0.2-, 0.5-, 2-, 5-, 10-, 20-, or 50-fold reduction in endogenous proteinase activity as compared to a plant without exogenous proteinase inhibitor II.

As used herein, "inhibited programmed cell death" or "inhibited senescence" refers to the inhibition of biochemical markers associated with PCD such as DNA fragmentation or the expression of genes and/or proteins associated with PCD. Examples of biochemical markers of PCD in plants include, but are not limited to, cysteine proteases and cysteine protease inhibitor (cystatin) (Solomon et al., 1999, *Plant Cell* 11: 431–443), S1-type nuclease, *Zinnia* endonuclease 1 (ZEN1) (Ito and Fukuda, 2002, *Plant Cell* 14: 3201–11), plant proteases including cysteine proteases, aspartic proteases, serine proteases (reviewed in Beers et al., 2000, *Plant Mol. Biol.* 44: 399–415), and SAG (senescence-associated genes) (Hensel et al., 1993., *Plant Cell* 5: 553–564; Lohman et al., 1994, *Plant Physiol.* 92: 322–328). The terms can also refer to morphological changes associated with inhibiting PCD or senescence, such as, but not limited to, increased biomass, increased shelf-life, improved color retention, and reduced cellular deterioration of plant organs, e.g. rigidity in fruit, etc. Inhibition can be measured by any method known to one of skill in the art to measure a biochemical or morphological change. Inhibition can be at least 5%, at least 10%, at least 20%, at least 30%, at least 40%, at least 50%, at least 60%, at least 70%, at least 80%, at least 90% or more compared to a plant or plant part without added proteinase inhibitor II. The terms refer to both the whole plant and plant parts once detached from the whole plant.

As used herein, "heterologous protein" refers to any protein which is desired to be expressed in a particular plant species which is not normally expressed in that plant species. In a preferred embodiment, the heterologous protein is not a PIN2 protein. Examples of heterologous proteins include plant-expressed heterologous proteins/enzymes (e.g., those involved in improving amino acid biosynthesis/protein content, phytoremediation, biosynthesis of bioplymers), plant-expressed biopharmaceuticals (e.g. recombinant subunit vaccines, monoclonals, recombinant antibodies, human/animal proteins expressed in plants) and plant-expressed proteins for improvement of traits (e.g. herbicide-resistance, insect-resistance, pathogen-resistance, drought- or salt-tolerance and cold-tolerance) (Daniell et al., 2002, *Trends in Plant Sci.* 7: 84–91; Ma et al., 2003, *Nat. Rev. Genet.* 4:794–805).

As used herein, "part" of a plant refers to parts of a plant that may be detached from the whole plant, such as flowers, seeds, fruits, leaves, stems, roots, etc.

As used herein, "transformed plant" or "modified plants" refers to plants comprising plant cells that express the exogenous PIN2 protein of the present invention. The term includes, but is not limited to, plants produced by nuclear transformation, i.e., where the transformed gene is expressed from the nuclear genome (transgenic plants), and plants produced by plastid transformation, i.e., where the transformed gene is expressed from the plastid genome (transplastomic plants). Transformed plants include plant seedlings and plant progeny that are produced via sexual or asexual reproduction.

As used herein, "biolistics" refers to a method for injecting DNA into cells by mixing the DNA with small metal particles and then firing the particles into the host cell at very high speeds.

4. DESCRIPTION OF THE FIGURES

The application contains drawings executed in color, particularly FIGS. 5a–n, 6a–u, 7a–l, 8a–n, and 20a–20d. Copies of this patent application publication with color drawings will be provided by the United States Patent and Trademark Office upon request and payment of the necessary fee.

FIGS. 1a & b. (a) Nucleotide sequence (SEQ ID NO:1) and (b) amino acid sequence (SEQ ID NO:2) of SaPIN2a.

FIGS. 2a & b. (a) Nucleotide sequence (SEQ ID NO:3) and (b) amino acid sequence (SEQ ID NO:4) of SaPIN2b.

FIG. 3. Northern blot analysis of SaPIN2a and SaPIN2b mRNA at different stages of *S. americanum* flower development. The blot was probed with a $^{32}$P-labeled SaPIN2a cDNA, reprobed with $^{32}$P-labeled SaPIN2b cDNA followed by $^{32}$P-labeled 18S ribosomal DNA. Each lane contains 20 µg of total RNA extracted from young floral buds 72 h before opening (lane 1), mature buds 24 h before opening (lane 2), open flowers (lane 3), old flowers 24 h after opening (lane 4) and senescent flowers 84 h after flower opening (lane 5). Bar=0.5 cm.

Figure 4:
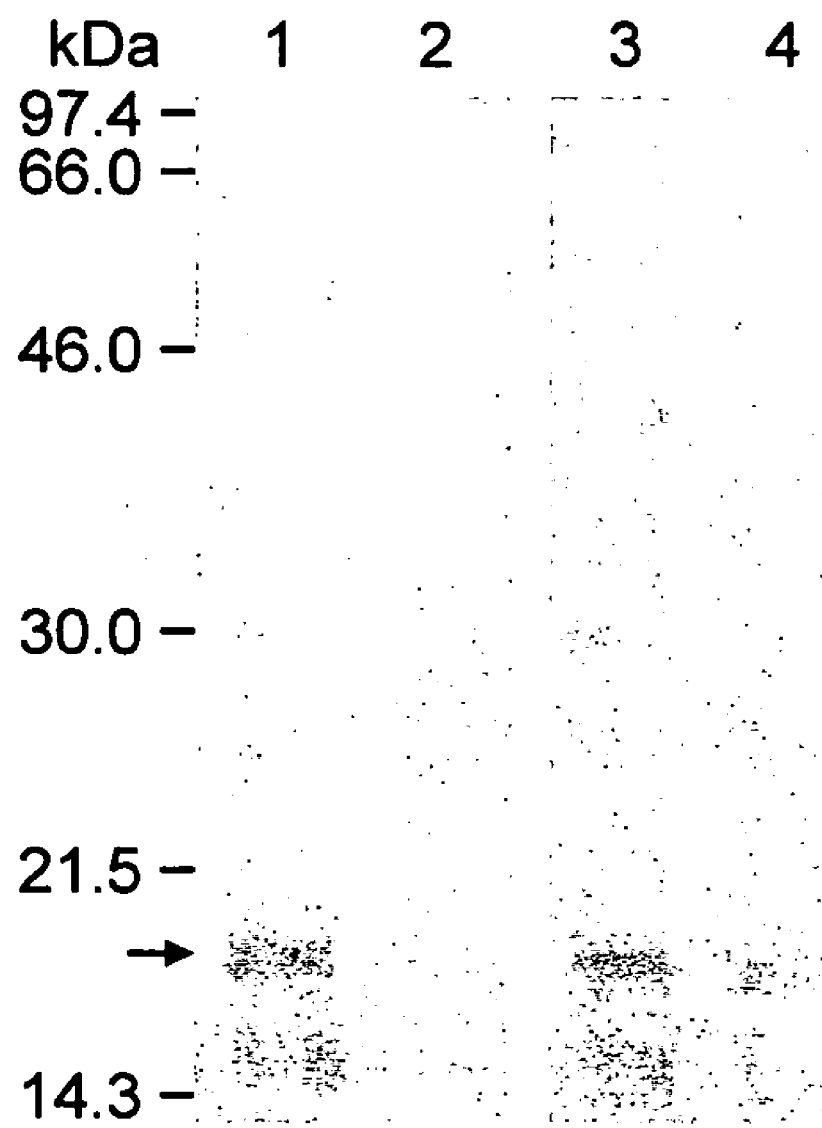

FIG. 4. Western blot analysis of SaPIN2a and SaPIN2b expression in *S. americanum* floral buds and open flowers. Total protein (20 µg) extracted from *S. americanum* floral buds or open flowers was separated by SDS-PAGE, transferred onto Hybond-C membrane and cross-reacted with antibodies specific to SaPIN2a (lanes 1–2) or SaPIN2b (lanes 3–4). Arrow indicates an SaPIN2a cross-reacting band of apparent molecular mass 16.7 kDa detected in floral buds (lane 1) and open flowers (lane 2) and an SaPIN2b cross-reacting band of apparent molecular mass 16.7 kDa detected in floral buds (lane 3) and open flowers (lane 4).

FIGS. 5a–n. In situ hybridization analysis of SaPIN2a mRNA (a–f) and immunolocalization of SaPIN2a (g–n) in floral buds and open flowers. Tissue sections were hybridized with either digoxigenin-labeled antisense SaPIN2a RNA probe (b, f) or sense SaPIN2a RNA probe (a, d) as control. Tissue sections were stained with either affinity-purified SaPIN2a-specific antibodies (h, j, k, m) or preimmune serum (g, i, l). Longitudinal sections of young floral bud (a, b). Magnification of panel b at the stigma (c). Longitudinal sections of open flowers (d, f). Magnification of panel f at the stigma (e). Longitudinal sections of young floral bud (g, h). Longitudinal sections of mature bud (i, j).

Transverse section of ovary in an open flower (k). Longitudinal sections of open flower (l, m). Longitudinal section of stigma and style from an open flower (n). Bar=100 µm. O, nucellar cells in ovule; P, placenta; Po, pollen; S, stigma; T, tapetum; Tt, stylar transmitting tissue; Vb, vascular bundle.

FIGS. 6a–u. In situ hybridization analysis of SaPIN2b mRNA (a–j) and immunolocalization of SaPIN2b (k–u) in floral buds and open flowers. Tissue sections were hybridized with either digoxigenin-labeled antisense SaPIN2b RNA probe (b, c, e–i) or sense SaPIN2b RNA probe (a, d and j) as control. Tissue sections were stained with either affinity-purified SaPIN2b-specific antibodies (l–q, s–u) or preimmune serum (k, r). Longitudinal sections of young floral bud (a, b). Magnification of panel b at the anther (c). Longitudinal sections of mature buds (d, e, f). Magnifications of the stigmas from panels e and i, respectively (g, h). Longitudinal sections of open flowers (i, j). Longitudinal sections of mature buds (k, l). Longitudinal sections of young floral bud (m). Magnification of panel m at the anther (n) Transverse section of mature bud (o). Longitudinal section of stigma and style in young bud (p). Longitudinal section of stigma and style in open flower (q). Longitudinal sections of open flower (r, s). Transverse section of ovary in open flower (t). Transverse section of anther and style in open flower (u). Bar=100 µm. O, nucellar cells in ovule; P, placenta; Po, pollen; S, stigma; T, tapetum; Tt, stylar transmitting tissue; Vb, vascular bundle.

FIGS. 7a–l. In situ hybridization analysis of SaPIN2a mRNA (a–c) and SaPIN2b mRNA (d–e) and immunolocalization of SaPIN2a (g–i) and SaPIN2b (j–l) in senescent flowers. Tissue sections were hybridized with either digoxigenin-labeled antisense SaPIN2a RNA probe (b–c) or sense SaPIN2a RNA probe (a) as control, and with either digoxigenin-labeled antisense SaPIN2b RNA probe (e–f) or sense SaPIN2b RNA probe (d) as control. In immunolocalization of SaPIN2a and SaPIN2b, tissue sections were stained with either affinity-purified SaPIN2a-specific antibodies (h–i) or preimmune serum (g), and with either affinity-purified SaPIN2b-specific antibodies (k–l) or preimmune serum (j). Bar=100 µm. O, nucellar cells in ovule; P, placenta; Vb, vascular bundle. Yellow arrowheads indicate the inner cell layer of the embryo sac; red arrowheads indicate the subsequent cell layer. Longitudinal sections of ovary in senescent flower (a, b, d, e, g, h, j and k). Magnification of panel b at the ovule (c). Magnification of panel e at the ovule (f). Magnification of panel h at the ovule (i). Magnification of panel k at the ovule (l).

Figure 8:
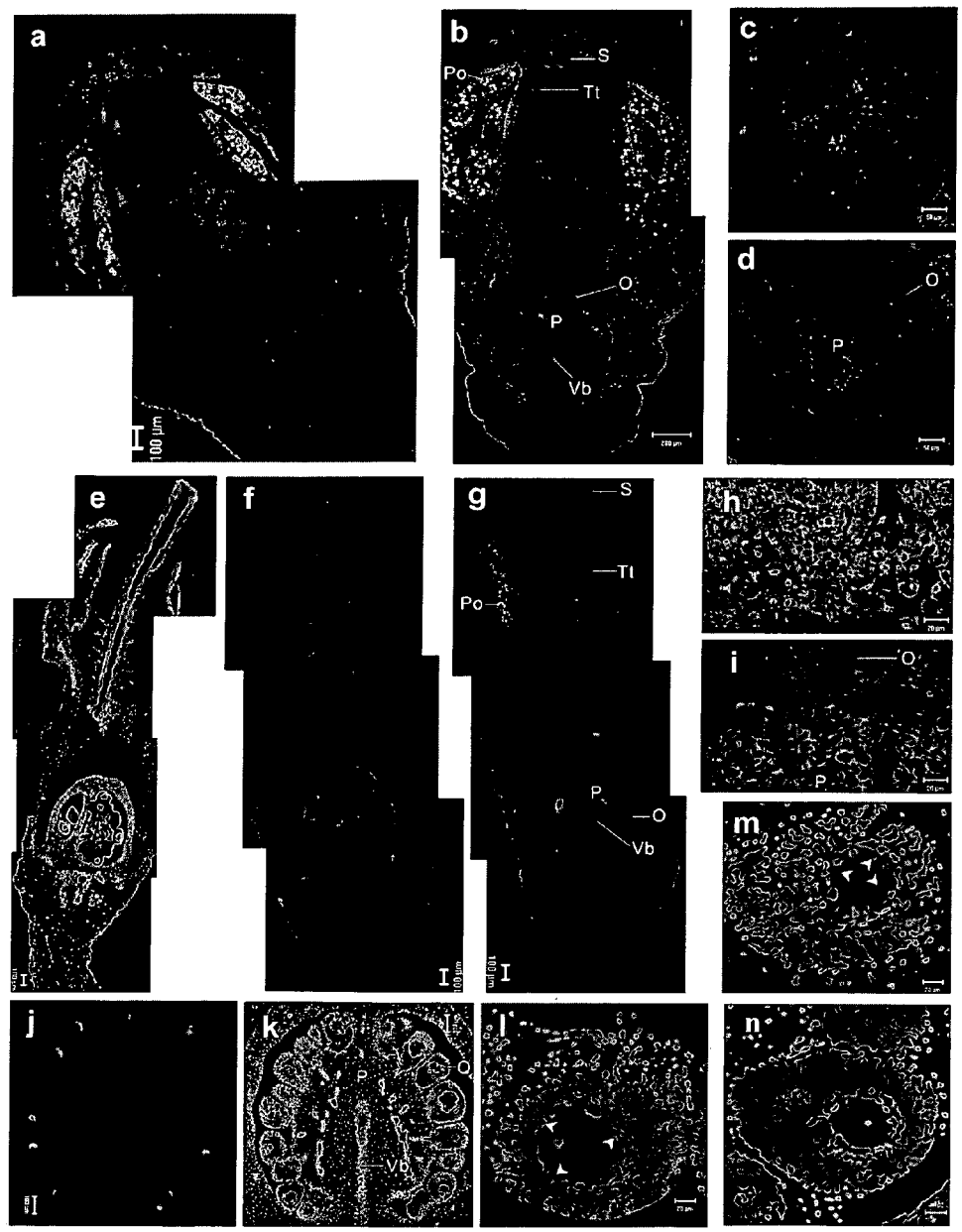
Figure 9:
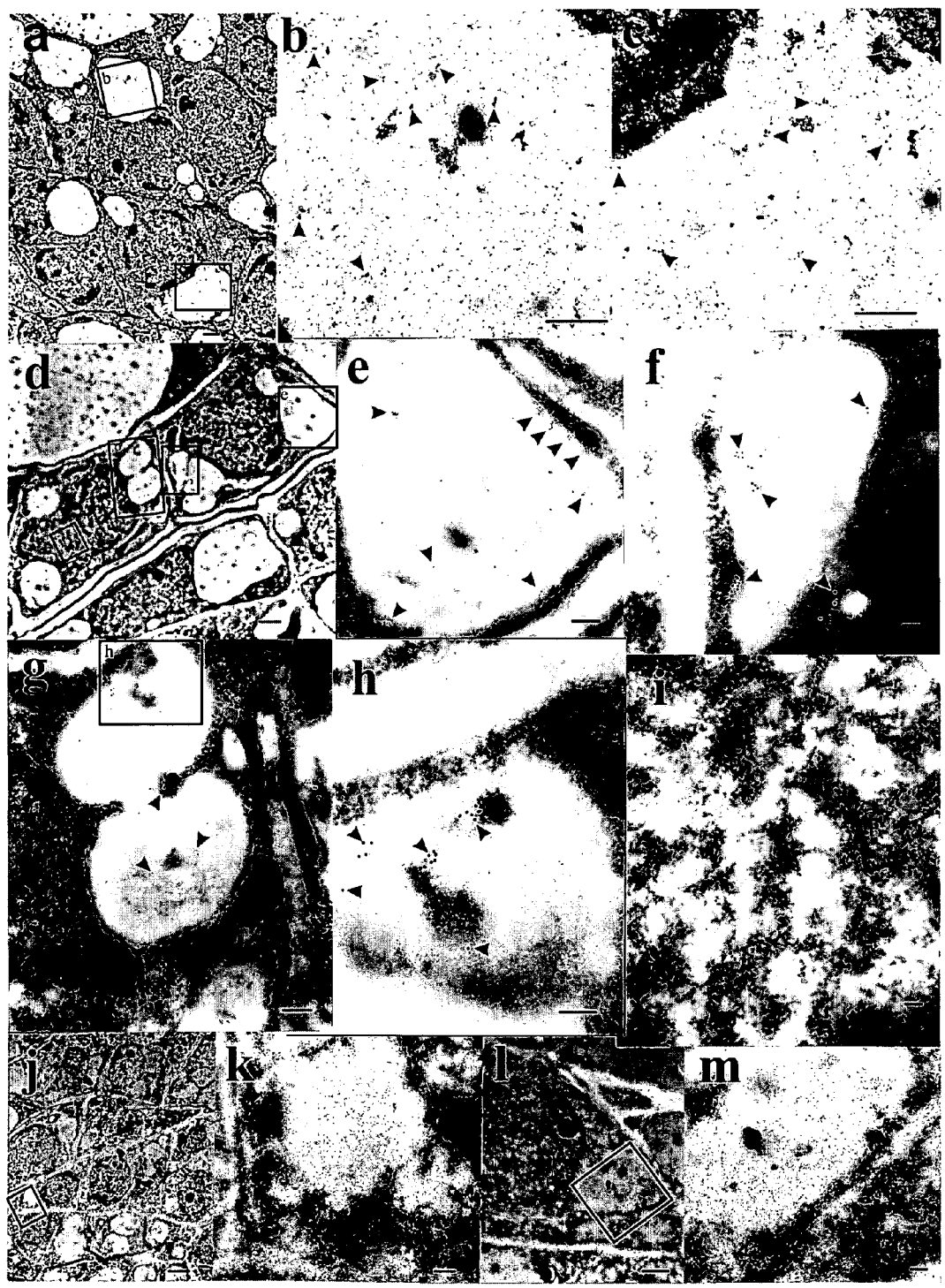

FIGS. 8a–n. Localization of nuclear DNA fragmentation by the TUNEL assay in flower sections. Sections of young floral buds (a–d), mature flowers (e–i) and senescent flowers (j–n) were subjected to the TUNEL assay. Positive control sections at each developmental stage were treated with DNase I prior to labelling; two such sections are shown (e and n). Negative control sections (a, c, f and j) in which TdT was omitted. Longitudinal sections of young floral bud (a, b). Transverse sections of ovary in young floral bud (c, d). Longitudinal sections of mature flowers (e, f, g). Magnification of panel f at the ovary (h). Magnification of panel g at the ovary (i). Longitudinal sections of ovary in senescent flowers (j, k). Magnifications of panel k at ovules (l, m). Longitudinal section of senescent ovule in TUNEL-positive control (n). Arrowheads indicate the inner cell layer of the embryo sac. Bar=20 µm (h, i, l, m, n), 50 µm (c, d), 100 µm (a, e, f, g, j, k) and 200 µm (b). O, nucellar cells in ovule; P, placenta; Po, pollen; S, stigma; Tt, stylar transmitting tissue; Vb, vascular bundle.

FIGS. 9a–m. Immunogold localization of SaPIN2a and SaPIN2b in the nucellar cells of the ovules of S. americanum floral bud using TEM. Transverse sections were stained with affinity-purified SaPIN2a-specific antibodies (a–c), SaPIN2b-specific antibodies (d–i), preimmune serum (j–k) or blocking solution (l–m). Transverse section of ovule stained with affinity-purified SaPIN2a-specific antibodies, Bar=1 µm (a). Magnification of the boxed areas in panel a showing localization of SaPIN2a to the vacuole, Bar=0.3 µm (b, c). Transverse section of ovule stained with affinity-purified SaPIN2b-specific antibodies, Bar=1 µm (d). Magnification of the boxed areas in panel d showing localization of SaPIN2b to the vacuole, Bars=0.3 µm (e, g), 0.1 µm (f). Magnification of the box in panel g, Bar=0.1 µm (h). Magnification of the nucleus boxed in panel d, Bar=0.1 µm (i). Control for panel d, replacing anti-SaPIN2b antibodies with preimmune serum, Bar=2 µm (j). Magnification of the box in panel j, Bar=0.2 µm (k). Control for panels a and d, omission of anti-SaPIN2a and anti-SaPIN2b antibodies, blocking solution only, Bar=1 µm (l). Magnification of the box in panel 1, Bar=0.2 µm (m). Arrowheads indicate gold particles.

Figure 10A:
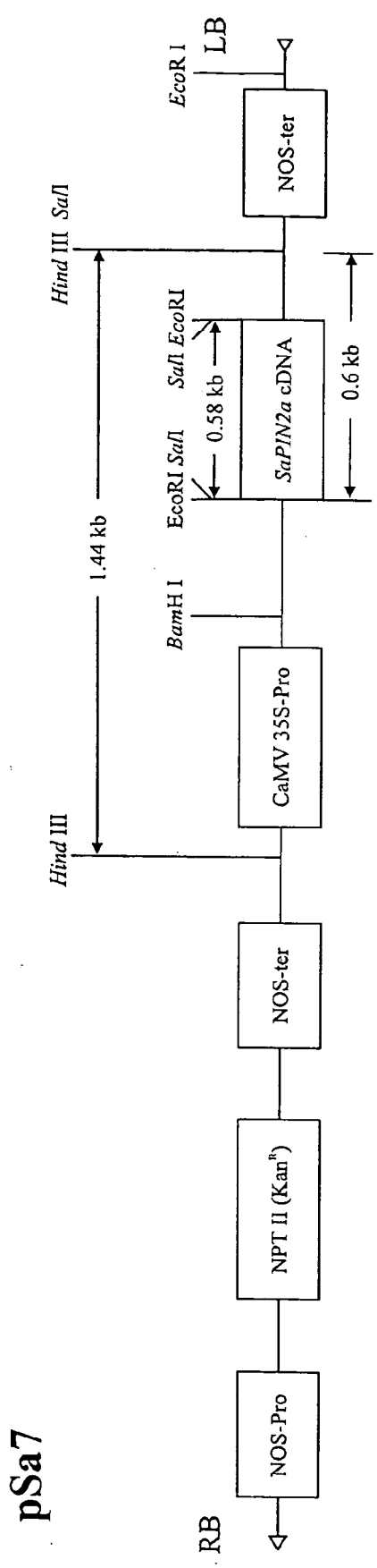

FIGS. 10a & b. (a) Structure of T-DNA region of pSa7. RB, right border of the transferred DNA (T-DNA); NOS-Pro, nopaline synthase (NOS) promoter; NPT II, neomycin phosphotransferase II gene encoding resistance to kanamycin (Kan$^R$); NOS-ter, NOS terminator; CaMV 35S-Pro, promoter of cauliflower mosaic virus (CaMV) 35S RNA; SaPIN2a, Solanum americanum proteinase inhibitor IIa; LB, left border of the T-DNA. (b) DNA sequence of junction of CaMV 35S promoter and SaPIN2a cDNA in pSa7(SEQ ID NO: 15). The sequence in italics is from parent binary vector pBI121 and the remaining sequence is from the plasmid pSa2, a pBluescript II SK-derivative containing the full-length SaPIN2a cDNA (Xu et al., 2001, Plant Mol. Biol. 47: 727–738). The transcription start site (Jefferson et al., 1987, EMBO J. 6,3901–3907) is underlined. The start codon (atg) of SaPIN2a is in bold.

FIGS. 11a & b. Southern blot analysis of DNA from $R_0$ transgenic lettuce plants. Twenty µg of genomic DNA was digested with EcoRI (a) or BamHI (b) and fractionated on a 0.8% agarose gel. A $^{32}$P-labeled probe prepared by random-primed labeling of the SaPIN2a cDNA was used. The identification number of the individual transgenic lettuce line is indicated on the top of each lane. WT, wild-type control plant. The DNA molecular size markers are shown on the sides. Arrows indicate the 0.58-kb hybridization band corresponding to the SaPIN2a cDNA.

FIGS. 12a & b. Northern blot analysis of RNA from $R_0$ transgenic lettuce plants. Total RNA (20 µg) was isolated from leaves of wild-type (WT) or transgenic lettuce (TL) and from stems of S. americanum (ST), as positive control. The blots were probed with a $^{32}$P-labeled SaPIN2a cDNA. The 25S rRNA bands stained with methylene blue are at the bottom panel. The hybridization band corresponding to the transcript of SaPIN2a cDNA is indicated by an arrowhead (in S. americanum stems) or an arrow (in transgenic lettuce leaves). The 25S rRNA bands stained with methylene blue are at the bottom panel. Blot shown in (b) is a repeat of RNA samples from TL10, 11 and 34 that were degraded in (a) together with TL52 as an internal control.

FIGS. 13a, b, c & d. Northern blot and western blot analyses of $R_1$ transgenic lettuce plants. Total RNA (20 µg) and total protein (20 µg) were isolated from identical leaves and stems of 38-day $R_1$ transgenic (TL1, 11 & 33) and wild-type (WT) lettuce plants. Total RNA (20 µg) and total protein (14 µg) isolated from S. americanum (Sa) stems were included as a positive control. (a): Northern blot analysis with a $^{32}$P-labeled SaPIN2a cDNA probe. The hybridization band corresponding to the transcript of SaPIN2a cDNA is indicated by an arrowhead (0.67-kb mRNA in *S. americanum* stems) or an arrow (0.93-kb mRNA in transgenic lettuce leaves). (b): The 25S rRNA bands stained with ethidium bromide are shown to demonstrate amounts of total RNA loaded in (a). (c): western blot analysis with SaPIN2a-specific antibodies. Cross-reacting bands in lettuce leaves (18.1-kDa) and *S. americanum* stems (16.7-kDa) are indicated. (d): Coomassie blue staining of total protein from transgenic and wild-type plants separated on a 4–20% gradient SDS-PAGE to demonstrate amounts of total protein loaded in (c).

FIGS. 14a & b. Proteinase inhibitory activity assay of transgenic lettuce leaf extracts. Leaf extracts were prepared from 54-day old wild-type (WT) or transgenic (TL1, 11 & 33) $R_1$ plants. Each value represents the mean±SE of three replicates. (a) trypsin inhibitory activity assay. One μg of bovine trypsin (Calbiochem) was incubated with 150 μl of assay buffer (standard) or leaf extracts and the residual trypsin activity was determined by measuring the increase of absorbance at 247 nm during the hydrolysis of substrate. (b) chymotrypsin inhibitory activity assay. Two μg of bovine α-chymotrypsin (Calbiochem) was incubated with 50 μl of assay buffer (standard) or leaf extract and the residual chymotrypsin activity was determined by measuring the increase of absorbance at 256 nm during the hydrolysis of substrate.

FIGS. 15a & b. Trypsin- and chymotrypsin-like activity assay of transgenic lettuce leaf extracts. Leaf extracts were prepared from 54-day old wild-type (WT) or transgenic (TL1, 11 & 33) $R_1$ plants. Each value represents the mean±SE of three replicates. (a) trypsin-like activity assay. Leaf extract (150 μl) was directly incubated with substrate in the absence of bovine trypsin and the trypsin-like activity was determined by measuring the increase in absorbance at 247 nm during the hydrolysis of substrate. (b) chymotrypsin-like activity assay. Leaf extract (50 μl) was directly incubated with substrate in the absence of bovine α-chymotrypsin and the chymotrypsin-like activity was determined by measuring the increase in absorbance at 256 nm during the hydrolysis of substrate.

FIGS. 16a, b, c & d. Growth of cabbage loopers (*T. ni*) fed on leaves of $R_0$ transgenic and wild-type lettuce. Newly hatched first-instar larvae were fed with daily fresh leaves from $R_0$ transgenic plants TL1(a), TL7(b), TL11(c) and TL15(d), each with leaves from wild-type control plants (WT). The points shown represent the total weight of ten larvae.

FIGS. 17a, b, c & d. Cabbage loopers (*T. ni*) fed on leaves of transgenic (TL1) and wild-type lettuce. (a) *T. ni* larvae fed 8 days on leaves of transgenic lettuce (TL1); (b) *T. ni* larvae fed 8 days on leaves of wild-type lettuce; (c) resultant leaves of TL1 $R_0$ plants on day 8 of feeding trials; (d) resultant leaves of wild-type lettuce on day 8 of feeding trials.

Figure 18:
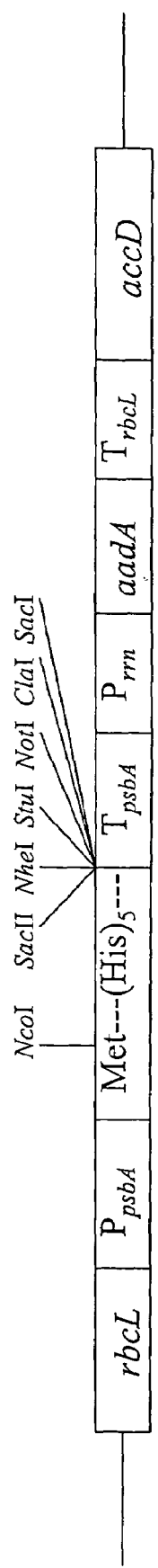

FIG. 18. pMLVHisA plastid transformation vector. The flanking regions rbcL and accD, derived from the tobacco plastid genome, are used in homologous recombination during plastid transformation. $P_{psbA}$ represents the promoter regulating expression of the inserted gene and $T_{psbA}$, the terminator. $P_{rrn}$ represents the promoter driving expression of the spectinomycin-resistance marker aadA and $T_{rbcL}$, the rbcL terminator. Met represents the start codon for the expressed recombinant (His)$_5$-tagged protein (5×His tag disclosed as SEQ ID NO: 16).

Figure 19:
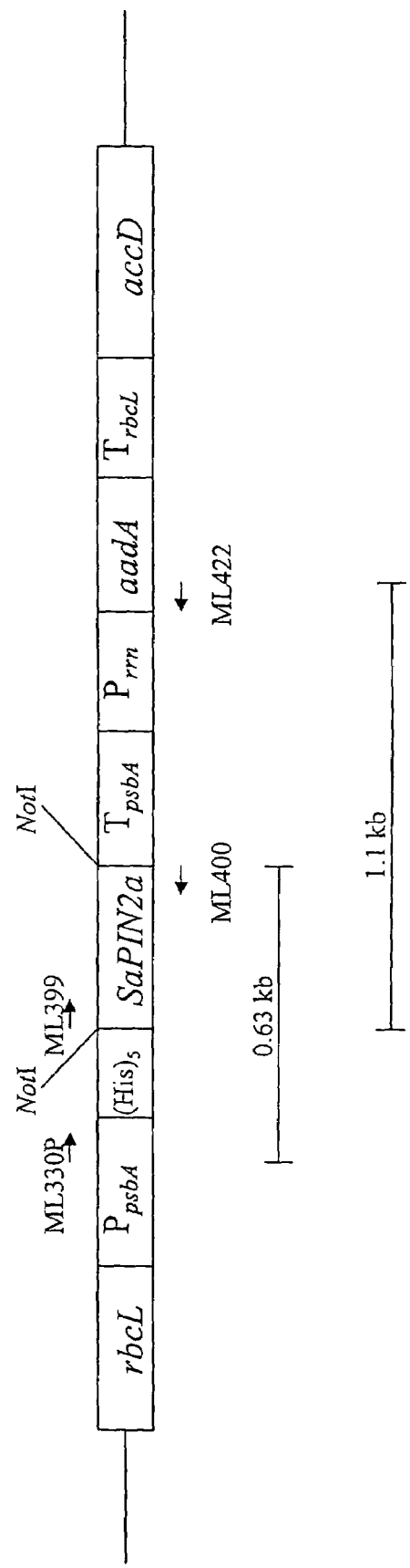

FIG. 19. The pMLVHisP plastid transformation vector containing the SaPIN2a cDNA. To generate pMLVHisP, a 0.5-kb NotI fragment of *S. americanum* cDNA encoding proteinase inhibitor II protein (SaPIN2a) was cloned in the NotI site of pMLVHisA. The (His)$_5$-tag (5×His tag disclosed as SEQ ID NO: 16) and SaPIN2a is fused in-frame. Primers ML330P, ML399, ML400 and ML422 were used in PCR analysis for detection of the recombinant DNA insert in the plastid transformants. The expected PCR-amplified fragments of 0.63-kb and 1.1-kb are indicated.

FIGS. 20a, b, c and d. Analysis of plantlets generated from transformation using plastid transformation vector pMLVHisP. (a) Green shoots developed from bombarded tobacco leaves after plastid transformation with pMLVHisP. (b) A tobacco plant used in PCR analysis. (c) Ethidium bromide stained gel showing a 0.63-kb PCR-amplified fragment using primers ML330P and ML400 from a transplastomic line (lane 8). This band is absent in other putative lines (lane 2–7, lane 9) and wild-type tobacco (lane 1). DNA markers (lane 10). (d) Southern blot analysis on the above gel with $^{32}$P-labeled SaPIN2a probe show a corresponding 0.63-kb SaPIN2a hybridizing band (denoted by arrow) in the transplastomic line (lane 8).

5. DETAILED DESCRIPTION OF THE INVENTION

5.1 SaPIN2a and SaPIN2b

5.1.1 cDNA Cloning

The cloning of SaPIN2a cDNA and the cloning of a portion of SaPIN2b cDNA are disclosed in Xu et al. (2001, supra), which is incorporated by reference in its entirety. The entire sequence of SaPIN2b has been determined using PCR amplification of total RNA using a SaPIN2b specific primer as described in the Examples. Other proteinase inhibitor II DNA related to SaPIN2a DNA may be isolated and characterized using techniques known in the art. A cDNA or genomic DNA specific for proteinase inhibitor II protein or nucleic acid may be cloned and sequenced in a variety of ways, e.g., dideoxy chain termination sequencing, see, e.g., Sambrook et al., 1989, Molecular Cloning: A Laboratory Manual, Cold Spring Harbor Laboratory Press, Cold Spring Harbor, N.Y.

The polynucleotides that may be used in the present invention include polynucleotides having the DNA sequences presented herein, and additionally include any nucleotide sequence encoding a contiguous and functional proteinase inhibitor II encoding open reading frame (ORF) that hybridizes to a complement of the DNA sequences presented herein under highly stringent conditions. The polynucleotide may be 30, 100, 200, 300, 400, 500 or 600 nucleotides in length and encode a functionally active fragment. By way of example and not limitation, high stringency hybridization conditions can be defined as follows: The filter-bound DNA were hybridized in a solution containing 50% deionized formamide, 6×SSC, 5× Denhardt's, 1% SDS, 100 μg/ml denatured salmon sperm DNA at 42° C. overnight (about 4–16 hours), and washing in 0.1×SSC, 0.1% SDS at 65° C. (Ausubel F. M. et al., eds., 1989, Current Protocols in Molecular Biology, Vol. I, Green Publishing Associates, Inc., and John Wiley & sons, Inc., New York).

For oligonucleotide probes, by way of example and not limitation, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos).

Additionally contemplated polynucleotides that may be used in the present invention include any nucleotide sequences that hybridize under moderately stringent conditions to the complement of the DNA sequences that encodes a proteinase inhibitor II. The polynucleotide may be 30, 100, 200, 300, 400, 500 or 600 nucleotides in length and encode a functionally active fragment, analog or variant of a proteinase inhibitor II protein. By way of example but not limitation, such moderately stringent conditions may include, e.g., washing in 0.2×SSC/0.1% SDS at 42° C. (Ausubel et al., 1989, supra).

Additionally contemplated polynucleotides that may be used in the present invention include any nucleotide sequences that hybridize under low stringency conditions to the complement of the DNA sequences that encode a proteinase inhibitor II. By way of example and not limitation, procedures using such conditions of low stringency are described in Shilo and Weinberg, 1981, *Proc. Natl. Acad. Sci. USA* 78:6789–6792.

Moreover, a variant of proteinase inhibitor II can also be used in the present invention. A variant may comprise one or more changes in the amino acid sequence of the proteinase inhibitor, e.g., by way of addition, substitution, or deletion of one or more amino acids, compared with the wild type proteinase inhibitor. Any change should not abolish the biological activities of the proteinase inhibitor, though it may increase or decrease the biological activities depending on the nature of the changes. Preferably, the amino acid changes are conservative. A "conservative amino acid substitution" is one in which the amino acid residue is replaced with an amino acid residue having a side chain with a similar charge. Families of amino acid residues having side chains with similar charges have been defined in the art. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 4th ed., Ed. by L. Stryer, WH Freeman and Co. 1995).

In various embodiments, the proteinase inhibitor II, fragment, variant, analog, or derivative may be expressed as a fusion, or chimeric protein product (comprising the proteinase inhibitor, fragment, analog, or derivative joined via a peptide bond to a heterologous protein sequence (of a different protein)). The size of these fragments may be 20, 30, 40, 50, 60, 70, 80, 90 or 100 amino acids of the proteinase inhibitor II protein. Such a chimeric gene product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Preferably, the fragment, analog, and derivative of the proteinase inhibitor in the fusion protein retains the ability to perform its function.

Alternatively, DNA for the expression of the heterologous desired protein (e.g., edible vaccines, antibodies, etc.) intended for protection against endogenous plant proteases could be introduced on a separate plasmid, using a different selectable marker, into transformed lettuce (or any plant species) that is already expressing SaPIN2a or SaPIN2b. The resultant transformed plant will co-express the heterologous protein and SaPIN2a or SaPIN2b and thus the heterologous protein would gain protection against endogenous plant proteases.

A cDNA or genomic DNA specific for a plant may be cloned through screening a cDNA or genomic DNA library. Such a library may be prepared, for example, from messenger RNA or genomic DNA from the plant. For general background on molecular biology techniques and on how to prepare a cDNA library and a genomic library, see, e.g., Ausubel F. M. et al., supra; Sambrook et al., 1989, supra; and U.S. Pat. No. 5,650,148.

The library may be screened with a nucleotide fragment specific for a part of the proteinase inhibitor II. For example, the protein sequence of a proteinase inhibitor II may be determined using techniques well known to those of skill in the art, such as via the Edman degradation technique. (See, e.g., Creighton, 1983, "Proteins: Structures and Molecular Principles", W.H. Freeman & Co., New York, pp.34–49). The amino acid sequence obtained may be used as a guide for the generation of oligonucleotide mixtures that can be used to screen a cDNA library for the cDNA sequence encoding the proteinase inhibitor II.

Or, for example, two stretches of protein sequences specific for the proteinase inhibitor II may be determined. A set of degenerate oligonucleotides specific for each stretch is prepared and the oligonucleotides are used in a polymerase chain reaction ("PCR") amplification. Oligonucleotides are at least about 6 nucleotides long, more preferably at least about 10, more preferably at least about 15, more preferably at least about 20, more preferably at least about 30, more preferably at least about 40 nucleotides. The template in the PCR reaction would be, for example, a mixture of cDNA or genomic DNA that is known to contain or suspected to contain a DNA polynucleotide specific for the proteinase inhibitor II of interest. A cDNA template may be obtained in a variety of ways, for example, by isolating a mixture of different cDNA species from a cDNA library or, for example, by reverse transcribing total mRNA from a cell or organism known to (or suspected to) express the proteinase inhibitor II. For background on PCR, see, e.g., Ausubel, supra, and PCR Protocols: A Guide to Methods and Applications, 1990, Innis, M. et al., eds. Academic Press, Inc., New York.

In order to clone a full-length cDNA, fragments, analogs, and derivatives thereof, or genomic DNA sequence from any species or to clone variant or heterologous forms of the proteinase inhibitor II, labeled DNA probes made from nucleic acid fragments corresponding to any of the polynucleotides discussed herein or made using the methods of the invention may be used to screen a cDNA library or a genomic DNA library (for example, a phage library) as described in, e.g., Ausubel F. M. et al., supra; Sambrook et al., 1989, supra.

5.1.2 Protein Sequences

SaPIN2a and SaPIN2b are characterized by the presence of two inhibitor domains, Inhibitory domain 1 and Inhibitory domain 2 (Xu et al., 2001, *Plant Mol Biol* 47:727–738). Each inhibitory domain is characterized by the presence of eight cysteine residues. Inhibitory domain 1 contains a putative trypsin-reactive site, $R^{32}$-$E^{33}$ in SaPIN2a. Inhibitory domain 2 contains a putative chymotrypsin-reactive site, $F^{89}$-$E^{90}$ in SaPIN2a.

In certain embodiments of the present invention, the nucleic acid molecules or polypeptides useful for the present invention comprise a minimal active fragment containing a trypsin-reactive site or a chymotrypsin reactive site.

5.2 Production of Antibodies

For the production of antibodies, various host animals may be immunized by injection with the proteinase inhibitor II (e.g., one corresponding to functional domain of the proteinase inhibitor II), truncated proteinase inhibitor II (a proteinase inhibitor II in which one or more domains have been deleted), functional equivalents of the proteinase inhibitor II, mutants of the proteinase inhibitor II, or short peptides (or fragments that are 5, 10, 20, 30, 35, 40, 50, 60, 70, 80, 90 or 100 amino acids in length, or multiples thereof) of proteinase inhibitor II. Epitopes of proteinase inhibitor II which illicit an immune response or provide antigenicity. Such host animals may include but are not limited to rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterologous populations of antibody molecules derived from the sera of the immunized animals.

Antibodies useful for the present invention include monoclonal antibodies (see, e.g., Kohler et al., 1975, *Nature* 256:495–497; and U.S. Pat. No. 4,376,110), chimeric antibodies (see, e.g., Morrison et al., 1984, *Proc. Natl. Acad. Sci. USA*, 81:6851–6855; Neuberger et al., 1984, *Nature*, 312: 604–608; Takeda et al., 1985, *Nature*, 314:452–454), single chain antibodies (see, e.g., U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–546), antibody fragments (see, e.g., Huse et al., 1989, *Science*, 246:1275–1281), anti-idiotypic antibodies or Fab fragments of such anti-idiotypes (see, e.g., Greenspan & Bona, 1993, *FASEB J* 7(5):437–444; and Nissinoff, 1991, *J. Immunol.* 147(8):2429–2438).

5.3 Expression of Proteinase Inhibitor II Using Recombinant DNA Technology

Proteinase inhibitor II, fragments thereof or fusion proteins thereof, are advantageously produced by recombinant DNA technology using techniques well known in the art. Such methods can be used to construct chimeric gene or expression vectors containing a proteinase inhibitor II nucleotide sequence and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. As used herein, the term chimeric gene refers to a combination of nucleic acid sequences for each part of the chimeric gene, which sequences have been engineered into relationship by recombinant DNA techniques, which sequences may also be in their separate parts endogenous or exogenous to the plant into which the chimeric gene is to be introduced.

Alternatively, RNA corresponding to all or a portion of a transcript encoded by a proteinase inhibitor II nucleotide sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

Any of host-expression vector system known in the art of biotechnology may be utilized to express the proteinase inhibitor II nucleotide sequence including, but not limited to, expression in bacteria, yeast, insect cells, mammalian cells, eukaryotic cells and plant cells. In these expression systems, any selection system may be used. Such selection may comprise growth on a selective medium (e.g., antibiotics, minimal media, etc.) or the use of an indicator (e.g., a dye, a fluorescent reagent, etc.).

In cases where plant expression vectors are used, the expression of the proteinase inhibitor II coding sequence may be driven by any of a number of regulatory elements. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, biolistics/particle bombardment, microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9. As used herein, regulatory elements include but are not limited to inducible and non-inducible promoters, enhancers, operators and other elements known to those skilled in the art that drive and regulate expression.

Preferably the promoter is capable of directing expression in a particular tissue of the plant and/or at particular stages of development of the plant. The promoter may be heterologous or homologous to the plant. Preferably the promoter directs expression to the fruit or leaves (as in the case of lettuce) for easy delivery of edible plant vaccines. Fruits or leaves eaten raw would be ideal for this purpose (e.g., tomatoes, lettuce, apples, bananas). Preferably the promoter directs expression to the endosperm of the plant seed or to the roots or tuber of the plant. A preferred promoter is the high molecular weight glutenin (HMWG) gene of wheat. Other suitable promoters will be known to the skilled in the art, such as the promoters of gliadin, branching enzyme, ADPG pyrophosphorylase, starch synthase and actin, for example.

5.4 Transformed Plants Expressing Proteinase Inhibitor II

A transformed plant with the ability to express a plant proteinase inhibitor II polypeptide may be engineered by transforming a plant cell with a gene construct comprising a sequence encoding a plant proteinase inhibitor II protein or polypeptide. In one embodiment, a plant promoter is operably associated with a sequence encoding the desired plant proteinase inhibitor II protein or polypeptide. As used herein, the term "operably associated" or "operably linked" refers to an association in which the regulatory regions (e.g., promoter, enhancer) and the nucleic acid sequence to be expressed are covalently joined and positioned in such a way as to permit transcription, and under the appropriate condition, translation. In a preferred embodiment of the present invention, the associated promoter is a strong and non tissue- or developmental-specific plant promoter (e.g., a promoter that strongly expresses in many or all plant tissue types). Examples of such strong, "constitutive" promoters include, but are not limited to, the CaMV 35S promoter (Odell et al., 1985, Nature 313:810–812), the T-DNA mannopine synthetase promoter, and their various derivatives. In another preferred embodiment, an inducible or repressible promoter is used to express the proteinase inhibitor II of interest in a plant, for example, a tet operator promoter as described in Weinmann et al., 1994, Plant J. 5:559–569; or a glucocorticoid-inducible promoter as described in McNellis et al., 1998, Plant J. 14:247–257; or an ethanol inducible promoter as described in Caddick et al., 1998, Nature Biotechnology 16:177–180. See, also, Gatz, 1995, Methods In Cell Biology 50:411–424, which describes inducible and repressible gene expression systems for plants. In another preferred embodiment, in plastid transformation, the promoter is a strong plastid promoter e.g., the promoter ($P_{psbA}$) of psbA, the plastid gene encoding the photosystem II 32 kD protein.

In one embodiment of the invention, a proteinase inhibitor II is expressed in a plant so that the proteinase inhibitor II polypeptide will be localized in the apoplastic space. The proteinase inhibitor II may be directed to the apoplastic space, when expressed in a plant, by expressing the proteinase inhibitor II polypeptide as a fusion protein together with a peptide that acts as a signal or transporter so that proteinase inhibitor II is localized in the apoplastic space of the transformed plant. A variety of signal or transporter peptides can be used, for example, the PR1b signal sequence as described in Lund et al., 1992, Plant Mol. Biol. 18:47–53; or the PR-1a, b and c signal sequences as described in Pfitzner et al., 1987, Nucl. Acids Res. 15:4449–4465. A fusion protein comprising a signal or transporter peptide and a proteinase inhibitor II polypeptide may be constructed by linking polynucleotides specific for each component to each other (e.g., the polynucleotides are linked in frame) so that the desired fusion protein is made when the fusion polynucleotide is expressed in a transformed plant. A skilled artisan would know how to construct a polynucleotide useful for expressing a proteinase inhibitor II in the apoplastic space of a transformed plant.

In another embodiment of the present invention, it may be advantageous to engineer a plant with a gene construct comprising a sequence encoding a plant proteinase inhibitor II protein or polypeptide operably associated with a tissue- or developmental-specific promoter, such as, but not limited to, the CHS promoter, the PATATIN promoter, etc. Such an embodiment is especially desirable to prevent flower senescence by expressing proteinase inhibitor II proteins or polypeptides during late floral development.

In yet another embodiment of the present invention, methods are provided for inhibiting programmed cell death or senescence in a plant or plant part by expressing proteinase inhibitor II in the plant or plant part. In a specific embodiment, the plant part is a flower, melon, vegetable or fruit.

In yet another embodiment, methods of prolonging the shelf life of vegetables, fruits, and flowers are also part of the present invention.

In yet another embodiment of the present invention, it may be advantageous to transform a plant with a gene construct comprising a sequence encoding a plant proteinase inhibitor II protein or polypeptide operably linked to a modified or artificial promoter. Typically, such promoters, constructed by recombining structural elements of different promoters, have unique expression patterns and/or levels not found in natural promoters. See, e.g., Salina et al., 1992, Plant Cell 4:1485–1493, for examples of artificial promoters constructed from combining cis-regulatory elements with a promoter core.

In yet an additional embodiment of the present invention, the expression of a proteinase inhibitor II polynucleotide may be engineered by increasing the copy number of the gene encoding the desired protein or polypeptide using techniques known in the art.

In yet another embodiment, it may be desirable to generate transformed plants expressing more than one proteinase inhibitor II gene, e.g. SaPIN2a and SaPIN2b. The genes may be located on two separate recombinant vectors or on a single recombinant vector.

For the production of high levels of PIN2 for extraction from the transformed plants of the invention, it is preferable to use plastid transformation. It is believed that plastid transformation will result in much higher levels of protein expression than that achieved in nuclear transformation. PIN2s can be used in applications for the in vitro inhibition of trypsin-like and chymotrypsin-like activities, especially during the preparation, extraction and purification of high-value proteins from plants. During these steps, in the absence of any proteinase inhibitors, the high-value proteins would be subject to degradation by endogenous proteinases. Thus, purified PIN2s can be added to plant, extracts during the preparation and purification of high-value products including recombinant biopharmaceuticals. Representative, plant-derived recombinant biopharmaceuticals for which PIN2 would be useful are described in Ma et al. (2003, Nature Reviews 4: 794–805).

To optimize yield of PIN2s, it is preferred that PIN2s are derived from plastid-transformed plants rather than from nuclear-transformed plants. In general, the yield of heterologous protein is higher from plastid transformation, due to the many more copies of the plastid genome than the nuclear genome (Staub et al., 2000, Plant Journal 6: 547–553; Daniell et al., 2001, J. Mol. Biol. 311: 1001–1009; Daniell et al., 2002, Trends in Plant Sci. 7: 84–91; Fernandez-San Millan et al., 2003, Plant Biotech. 1: 71–79).

To enable easy purification of PIN2s, the PIN2 protein can be tagged with a His-tag, as described in the Examples. Another affinity tag is the FLAG epitope (Ma et al., 2003, Nature Reviews 4: 794–805). Other methods and strategies available for the purification of heterologous proteins that can be applied for PIN2s are described elsewhere (Daniell et al., 2001, Trends in Plant Sci 6: 219–226; Ma et al., 2003, Nature Reviews 4: 794–805).

Isolation of proteins can be accomplished by gel filtration chromatography, affinity chromatography including the use of affinity tags, recombinant protein A expanded bed adsorption chromatography (Valdes R. et al., 2003, Biochem. Biophys. Res. Comm. 308: 94–100); single-step purification without chromatography, e.g. use of oleosin-fusions (Boothe et al., 1997, Drugs Dev. Res. 42:172–181), and the use of protein-based polymer GVGVP (SEQ ID NO: 17) encoded by synthetic genes (Daniell et al., 2001, Trends in Plant Science 6: 219–226). His-tagged proteins can be purified by immobilized-metal affinity chromatography, using an affinity column of Nickel-Nitrilotriacetic acid (Ni-NTA) Agarose (Qiagen) according to the manufacturer's instructions. See also Janknecht et al., 1991, Proc. Natl. Acad. Sci. 88: 8972–8976. The His-tag binds Ni-NTA. This His-tag can be fused at either the N-terminal or the C-terminal end of the desired peptide.

The present invention also encompasses the production of a heterologous protein in a transformed plant using the methods of the invention (see, generally, Outchkourov et al., 2003, *Plant Physiol.* 133:379–390). In these methods, a transformed plant expressing a heterologous protein can be generated before or after transformation with a proteinase inhibitor gene. Isolation of proteins can be accomplished as described for PIN2 proteins.

The present invention encompasses a transformed plant cell, transformed plants, and progreny thereof, that are produced by sexual or asexual reproduction.

5.5 Transformation of Plants and Plant Cells

Plants and plant cells may be transformed using any method known in the art. In an embodiment of the present invention, *Agrobacterium* is employed to introduce the gene construct into plants. Such transformation preferably uses binary *Agrobacterium* T-DNA vectors (Bevan, 1984, Nuc. Acid Res. 12:8711–8721), and the co-cultivation procedure (Horsch et al., 1985, *Science* 227:1229–1231). Generally, the *Agrobacterium* transformation system is used to engineer dicotyledonous plants (Bevan et al., 1982, Ann. Rev. Genet 16:357–384; Rogers et al., 1986, Methods Enzymol. 118:627–641). The *Agrobacterium* transformation system may also be used to transform, as well as transfer, DNA to monocotyledonous plants and plant cells. (see Hernalsteen et al., 1984, *EMBO J* 3:3039–3041; Hooykaas-Van Slogteren et al., 1984, Nature 311:763–764; Grimsley et al., 1987, Nature 325:1677–179; Boulton et al., 1989, *Plant Mol. Biol.* 12:31–40; and Gould et al., 1991, *Plant Physiol.* 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, particle gun bombardment (biolistics), protoplast transformation through calcium-, polyethylene glycol (PEG)- or electroporation-mediated uptake of naked DNA (see Paszkowski et al., 1984, *EMBO J* 3:2717–2722, Potrykus et al., 1985, *Molec. Gen. Genet.* 199:169–177; Fromm et al., 1985, *Proc. Nat. Acad. Sci. USA* 82:5824–5828; and Shimamoto, 1989, *Nature* 338:274–276) and electroporation of plant tissues (D'Halluin et al., 1992, *Plant Cell* 4:1495–1505). Additional methods for plant cell transformation include microinjection, silicon carbide mediated DNA uptake (Kaeppler et al., 1990, *Plant Cell Reporter* 9:415–418), and microprojectile bombardment (see Klein et al., 1988, *Proc. Nat. Acad. Sci. USA* 85:4305–4309; and Gordon-Kamm et al., 1990, *Plant Cell* 2:603–618). In any methods, selectable markers may be used, at least initially, in order to determine whether transformation has actually occurred. Useful selectable markers include enzymes which confer resistance to an antibiotic, such as gentamycin, hygromycin, kanamycin and the like. Alternatively, markers which provide a compound identifiable by a color change, such as GUS, or luminescence, such as luciferase, may be used. For plastid transformation, biolistics according the the method of Svab and Maliga (Svab et al., 1993, *Proc. Natl. Acad. Sci. USA* 90: 913–917) is preferred.

A chimeric gene comprising proteinase inhibitor II sequences may further comprise a gene switch mechanism which determines under what conditions or when the coding sequence is to be expressed. The gene switch may be a chemically induced promoter, a temperature controlled promoter, or developmentally regulated promoter, for example.

According to the present invention, a wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*, tobacco).

5.6 Screening of Transformed Plants and Plant Cells

According to the present invention, desired plants may be obtained by engineering one or more of the gene constructs expressing a proteinase inhibitor II as described herein into a variety of plant cell types, including but not limited to, protoplasts, tissue culture cells, tissue and organ explants, pollens, embryos, as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods may also be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

5.7 Transformed Plants Expressing an Engineered Proteinase Inhibitor II Polynucleotide Transformed plants are generated that express an engineered proteinase inhibitor II gene. A transformed plant expressing a proteinase inhibitor II has inhibited endogenous protease activity. In particular, a transformed plant expressing a proteinase inhibitor II has inhibited endogenous trypsin-like activity or inhibited endogenous chymotrypsin-like activity. A transformed plant expressing a proteinase inhibitor II is less susceptible to the pathogenic effects of the pathogen of interest. Transformed plants may be made using any of the techniques known in the art as described for plant proteinase inhibitor II expressing transformed plants.

The present invention also encompasses the production of a heterologous protein in a transformed plant using the methods of the invention. Such heterologous protein has a longer half-life and/or is not degraded by the endogenous proteinase due to the co-expression of a PIN2 gene.

Transformed plants expressing one or more proteinase inhibitor II gene polynucleotides capable of rendering said plants more resistant to a pathogen of interest may be from any plant species, plant genus, plant family, plant order, plant class, plant division of the kingdom of plants. See, e.g., U.S. Pat. Nos. 5,889,189; 5,869,720; 5,850,015; 5,824,842; PP10,742; PP10,704; PP10,682, which recite plant species, genuses, families, orders, classes and divisions in which the proteinase inhibitor II genes may be used.

Examples of plants are monocots, dicots, crop plants (i.e., any plant species grown for purposes of agriculture, food production for animals including humans, plants that are typically grown in groups of more than about 10 plants in order to harvest for any reason the entire plant or a part of the plant, e.g., a fruit, a leaf, a tuber, a stem, a root, a flower, etc., or a crop, e.g., grain, that the plants bear, etc.), trees (i.e., fruit trees, trees grown for wood production, trees grown for decoration, etc.), flowers of any kind (i.e., plants grown for purposes of decoration, for example, following their harvest), cactuses, etc.

Further examples of plants in which the proteinase inhibitor II genes may be expressed include *Viridiplantae, Streptophyta, Embryophyta, Tracheophyta, Euphyllophytes, Spermatophyta, Magnoliophyta, Liliopsida, Commelinidae, Poales, Poaceae, Oryza, Oryza sativa, Zea, Zea mays, Hordeum, Hordeum vulgare, Triticum, Triticum aestivum, Eudicotyledons, Core eudicots, Asteridae, Euasterids, Rosidae, Eurosids II, Brassicales, Brassicaceae, Arabidopsis, Magnoliopsida, Solananae, Solanales, Solanaceae, Solanum, Nicotiana.*

Also included are, for example, crops of particular interest including Solanaceae, including processing and fresh market tomatoes, ginger, scallions, water chestnuts, pepper and eggplant; leafy plants, including lettuce and spinach; *Brassicas*, including broccoli, brussels sprouts, calabrese, kale, cauliflower, red cabbage and white cabbage; cucurbits, including cucumber, melon, watermelon, zucchini and squash; large seeded plants, including peas, beans and sweetcorn; rooted plants, including carrots and onions; vegetatively propagated plants, including berries, grapes, banana, pineapple and rosaceous fruit and nut crops; and tropical crops, including tobacco, mango and papaya.

Thus, the invention has use over a broad range of plants including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum,* tobacco, *Vicia, Vitis, Vigna,* and *Zea.*

5.8 Polynucleotide Constructs for Expression of Engineered Gene in Transformed Plants A polynucleotide construct capable of directing the expression of an engineered proteinase inhibitor II gene product in a transformed plant of interest is constructed using general recombinant DNA and cloning techniques known in the art of biotechnology, see, e.g., Sambrook et al., supra; Ausubel et al., supra. Such a polynucleotide construct typically comprises a polynucleotide sequence that encodes an engineered proteinase inhibitor II gene product and one or more regulatory polynucleotide sequence. Regulatory sequences useful for the polynucleotide construct of the invention include, but are not limited to, a promoter, an enhancer, an intron, a splice donor, a splice acceptor, a polyadenylation sequence, a RNA stability regulating sequence, or an element of any one of the above (e.g., promoter elements including, but not limited to, a TATA box).

The polynucleotide construct comprises one or more regulatory elements capable of directing the expression of the engineered proteinase inhibitor II gene product of the invention. In a preferred aspect, the regulatory elements are capable of directing expression in a plant species in which expression of the engineered proteinase inhibitor II gene product is desired. In another preferred aspect, the regulatory elements are capable of directing expression in a cell type in which expression of the engineered proteinase inhibitor II gene product is desired in the plant species of interest.

Regulatory elements useful for the polynucleotide construct of the present invention are known to those of skill in the art, for example, promoter and enhancer elements of genes known to be expressed in the cell type and plant species of interest. A promoter useful for expression of the engineered proteinase inhibitor II gene product in a cell type of a plant species of interest may also be isolated using routine experimentation, for example, by isolating a promoter region of a gene known to be expressed in the desired fashion. For example, one may screen a genomic library with a cDNA probe specific for the 5' end of a messenger RNA known to be expressed in the cell type of interest of the plant species of interest. Such a 5' end cDNA probe should preferably be only about 100 base pairs to about 300 base pairs so that the clones identified in the genomic library are likely to include the 5' end of the gene possibly including the promoter region of the gene for which the probe is specific. The promoter region typically includes about 1,000 to about 2,000 base pairs upstream of the transcription initiation site. Thus, a promoter useful for the expression of the engineered proteinase inhibitor II genes of the present invention is a polynucleotide from about 2,000 base pairs upstream to about 50 base pairs downstream of the transcription initiation site of a gene known to be expressed in the cell type of interest in the plant species of interest, or is a portion of the polynucleotide.

In order to facilitate the proper processing of the engineered proteinase inhibitor II gene product, it may be necessary to include a nucleotide stretch that encodes a peptide sequence necessary for such processing. For example, a peptide sequence which is recognized by and functional in the transformed host plant, for example, to facilitate the entry of the proteinase inhibitor II gene product into the endoplasmic reticulum may be necessary, i.e., signal sequence.

5.9 Programmed Cell Death

Programmed cell death (PCD) describes any process by which cell death occurs during development or in response to the environment (see, e.g., Greenberg, 1996, *Proc Natl Acad Sci USA* 93:12094–7 for a review). In plants, cell death mechanistically resembles apoptosis in animal cells. Examples of PCD in plants include senescence and pathogenesis.

5.9.1 Senescence

Senescence is a phase of development during which cells undergo distinct metabolic and structural changes prior to cell death (Nooden, Senescence and Aging in Plants, (L. D. Nooden and A. C. Leopold, Ed.), pp. 391–439, Academic Press, San Diego, Calif., 1988). Senescence is the terminal phase of biological development in the life of a plant. It presages death and occurs at various levels of biological organization including the whole plant, organs, flowers and fruit, tissues and individual cells.

Senescence is not a passive process, but, rather, is an actively regulated process that involves coordinated expression of specific genes. Molecular studies using mRNA from senescing leaves and green leaves for in vitro translation experiments show a changed pattern of leaf protein products in senescing leaves (Thomas et al., 1992, *J. Plant Physiol.*, 139: 403–12). With the use of differential screening and subtractive hybridization techniques, many cDNA clones representing senescence-induced genes have been identified from a range of different plants, including both monocots and dicots, such as Arabidopsis, maize, cucumber, asparagus, tomato, rice and potato.

Plants with inhibited senescence will vegetatively grow longer, producing more flower, seed or fruit, than a corresponding non-transformed plant. Using the methods of the invention, transformed plants are generated and monitored for growth, development and either delayed senescence. Plants or detached parts of plants (e.g., cuttings, flowers, vegetables, fruits, seeds or leaves) exhibiting prolonged life or shelf life, (e.g., extended life of flowers, reduced fruit or vegetable spoilage, enhanced biomass, increased seed yield, reduced seed aging and/or reduced yellowing of leaves) due to inhibition of senescence. Plant lines generated using methods of the present invention that express an engineered proteinase inhibitor II gene product will exhibit prolonged life or shelf life when compared to a plant line of the same species that does not express the engineered proteinase inhibitor II gene product (i.e., a wild-type plant).

5.9.2 Pathogenesis

Pathogenesis refers to a defense mechanism whereby plants recognize certain pathogens and limit the growth of the pathogen to the site of infection. The infected cells undergo a localized cell death response limiting the ability of the pathogen to spread.

Pathogen resistance is an important property in plants and a useful tool for the protection of plants, especially crop plants. The term "plant", as used herein, includes whole plants, plant parts, individual plant cells, groups of plants cells (e.g., cultured plant cells) and progeny thereof. The term "enhance" when used to describe an increase of resistance of a plant to a pathogen, as used herein, includes the increase of the resistance of a plant that may have no resistance, or some resistance or substantial resistance to the pathogen to effecting the increase in resistance.

Plant pathogens include, but are not limited to, bacteria, viruses, fungi, nematodes and insects. A pathogen may infect a plant and cause severe damage to that plant, including death. Upon infection, a plant may initiate a protective reaction to the pathogen, e.g., a hypersensitive response, depending on whether the plant can recognize the pathogen.

Pathogens of the various classes may change, for example, through mutagenesis. Also, new pathogens may arise that were not previously encountered by a plant species. For example, when a plant (e.g., a crop, a fruit, a vegetable, etc.) is introduced into a continent (for example, through importation), a plant species is likely exposed to pathogens it has not encountered before.

It may be desirable to inhibit pathogens which may act by synthesizing proteinases. It may also be desirable to inhibit pathogenesis when the plant is treated with an agent which kills the pathogen to prevent further damage to the plant by PCD.

Plant lines generated using methods of the present invention that express an engineered proteinase inhibitor II gene product are more resistant to the pathogenic effects of a pathogen of interest when compared to a plant line of the same species that does not express the engineered proteinase inhibitor II gene product (i.e., a wild-type plant).

5.9.3 Assays for Programmed Cell Death

Inhibition of PCD in a plant or plant part generated using methods of the invention may be assayed for by any technique known to the skilled artisan. For example, methods used for detecting apoptosis can be used, such as those detecting DNA fragmentation, e.g. TUNEL assay. Additionally, nucleic acid based assays can be used to detect genes that have increased expression during PCD. Protein assays and antibody-based assays can be used to detect increased expression of proteins during PCD.

Plant or plant parts comprising the proteinase inhibitor II gene of the present invention will generally exhibit at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more reduction in the expression of a gene or protein expressed during PCD as compared to a plant or plant part not transformed with a PIN2 gene.

Furthermore, the plants or plant parts can be examined for signs of inhibited senenscence, e.g., extended life of flowers, reduced fruit or vegetable spoilage, enhanced biomass, increased seed yield, reduced seed aging and/or reduced yellowing of leaves.

Plant or plant parts transformed with a proteinase inhibitor II gene will generally exhibit at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or greater increase in the shelf life, size, or any other marker of inhibited senescence as compared to a plant or plant part not transformed with a PIN2 gene.

The increased resistance to a pathogen of a plant line generated using methods of the invention may be assayed for by any technique known to the skilled artisan. For example, one may infect a plant of the generated plant line and a plant of a wild-type plant line with a pathogen of interest. After such infection, the plant of the generated plant line will have at least an approximately 20% higher probability of surviving infection than the wild-type plant, more preferably at least about 40%, more preferably at least about 60% and most preferably at least about 80%.

Another way of testing a transformed plant made using the methods of the invention is by testing for necrosis inducing activity, for example, as described in Mahe et al., 1998, *J. Peptide Res*. 52:482–494. Thus, one can express an engineered proteinase inhibitor II gene in a transformed plant and infect the transformed plant with the pathogen of interest. For example, when applying a pathogen to the transformed plant expressing the engineered proteinase inhibitor II gene, one would observe clear necrosis or severe spreading necrosis in the wild-type plant but not in a transformed plant of the plant line from which the transformed plant was derived. Necrotic cell death can also be observed using histochemical staining reactions in addition to visual inspection.

The following examples are provided to further illustrate the current invention but are not provided to in any way limit the scope of the current invention.

6. EXAMPLES

6.1 Materials and Methods

Plant Material and Growth Conditions

American black nightshade (*S. americanum*) plants were planted in the greenhouse under natural light. Flowers at different stages of development were collected from the mature plant, immediately frozen in liquid nitrogen and stored at −80° C. for extraction of RNA and protein.

Seeds of lettuce (*Lactuca sativa* L. var. Great Lakes No.118) were obtained from Northrup King Co., Mpls., Minn. 55440, USA. Plant tissue cultures were maintained and propagated in vitro in a growth chamber at 22–24° C. under a 12 h light/12 h dark regime. Plants in soil were grown under natural conditions in a greenhouse.

Cloning and DNA Sequence Analysis of the 5'-end of the SaPIN2b cDNA

Total RNA was extracted (Nagy et al., 1988, in: S. B. Gelvin, RA and DPS Verma (Eds.), Plant Molecular Biology Manual, Kluwer Academic Publishers, Dordrecht, Netherlands, pp. B4:1–29) from *S. americanum* flowers for PCR using a SaPIN2b-specific primer (5'-CTCCATCA-CAAAATAAGGGGCAAGTA-3'; SEQ ID NO:5) corresponding to nucleotides 139–164 within the coding region of SaPIN2b cDNA (GenBank accession number AF209709) and the universal primer mix in the SMART RACE cDNA Amplification Kit (Clontech). DNA fragments containing the sequences of interest were cloned into pGEM-T vector (Promega) and sequenced using the DNA Sequencing Kit with Sequenase Version 2.0 (Amersham). The DNA sequence data were analyzed using the GCG sequence analysis software package (Genetics Computer Group Inc.).

Northern Blot Analysis

Twenty μg of total RNA extracted (Nagy et al., 1988, in: S. B. Gelvin, RA and DPS Verma (Eds.), Plant Molecular Biology Manual, Kluwer Academic Publishers, Dordrecht, Netherlands, pp. B4:1–29) from flowers at five different developmental stages (young floral buds, mature buds, open flowers, old flowers and senescent flowers) were denatured at 50° C. in the presence of glyoxal, separated by electrophoresis in 1.5% agarose gel and blotted onto Hybond-N membranes (Amersham). Blots were prehybridized in 50% deionized formamide, 1× Denhardt's solution, 6×SSPE, 0.1% SDS, 100 μg/ml denatured, sonicated salmon sperm DNA and 10% dextran sulfate at 42° C. for 4 h. Either the random-primed $^{32}$P-labeled SaPIN2a-specific probe or the SaPIN2b-specific probe was added to the blot for hybridization at 42° C. overnight. The SaPIN2a-specific probe was generated from a SaPIN2a cDNA derivative consisting of nucleotides 422–529 (GenBank accession number AF174381) and the SaPIN2b-specific probe was generated from a SaPIN2b cDNA derivative consisting of nucleotides 293–418 (GenBank accession number AF209709). The blot was washed at 65° C. in 0.1×SSC, 0.1% SDS. The hot SDS procedure (Amersham) was adopted for striping blots, i.e., the blot was washed in boiling solution of 0.1% SDS for 15 min, allowed to cool to room temperature, and subsequently rinsed briefly in 2×SSC. The RNA blots were rehybridized with an 18S rDNA probe to demonstrate equal loading of RNA in wells. The $^{32}$P-labeled 18S rDNA probe was generated from *S. americanum* cDNA prepared from floral buds using forward (5'-GCTCGAAGACGATCAGATACC-3'; SEQ ID NO:6) and reverse (5'-AGAAAGAGCTCT-CAGTCTGTC-3'; SEQ ID NO:7) primers designed from the *Arabidopsis thaliana* 18S rRNA gene sequence (GenBank accession number X16077) corresponding to nucleotides 1075–1095 and 1321–1341, respectively.

Western Blot Analysis

Synthetic peptides (GESDPRNPKDC; SEQ ID NO:8) and (CEGESDEPNVISNQ; SEQ ID NO:9) corresponding to amino acids 77–87 of SaPIN2a (Xu, et al., 2001, *Plant Mol. Biol*. 47: 727–738.) and amino acids 139–152 of SaPIN2b, respectively, were used for raising polyclonal antibodies in rabbit. Of the eleven residues on the SaPIN2a peptide, only seven occur in SaPIN2b and of the fourteen residues on the SaPIN2b peptide, only seven are in SaPIN2a. Total plant protein was extracted according to Kush et al. (1990, *Proc. Natl. Acad. Sci. USA* 87: 1787–1790). Protein concentration was determined by the method of Bradford (1976, *Anal. Biochem*. 72: 248–254.). Twenty μg of total protein was separated by SDS-PAGE (Laemmli, 1970, *Nature* 227: 680–685) using 15% w/v acrylamide gels and blotted onto Hybond-C membrane (Amersham) for western blot analysis (Sambrook et al., 1989, Molecular Cloning, A Laboratory Manual, 2$^{nd}$ ed. Cold Spring Harbor Laboratory Press, Plainview, N.Y.) with affinity-purified antibodies against SaPIN2a or SaPIN2b. The amplified alkaline phosphatase goat anti-rabbit immunoblot assay kit (Bio-Rad) was used to detect cross-reacting bands.

In situ Hybridization Analysis

In situ hybridization studies were carried out following Cox and Goldberg (1988, Analysis of plant gene expression. In: C. H. Shaw (Ed.), Plant Molecular Biology: A Practical Approach, IRL Press, Oxford, pp. 1–35.) and Drews and Okamuro (1996, In situ hybridization with nonradioactive probes. In: Cold Spring Harbor Arabidopsis Molecular Genetics Manual). A 0.1-kb PCR-derived SaPIN2a cDNA sequence corresponding to nucleotides 422–522 (GenBank accession number AF174381) and a 0.12-kb PCR-derived SaPIN2b cDNA sequence corresponding to nucleotides 293–418 (GenBank accession number AF209709) were each cloned in pGEM-T vector (Promega). Plasmid pGEM-T derivatives were cleaved with either SpeI or NcoI to generate antisense and sense RNA probes, synthesized in vitro with T7 or SP6 RNA polymerase, respectively. The antisense and sense RNA probes were hybridized to 10-μm floral sections at 42° C. overnight. Sections were washed and digoxigenin-labeled RNA probes were detected by an alkaline phosphatase-linked immunoassay (Boehringer Mannheim). This assay uses a color reaction with the substrates 5-bromo-4-chloro-3-indolyl phosphate and nitroblue tetrazolium salt which produces a purple precipitate. Slides were mounted with GelTol (Immunon) aqueous mounting medium and were examined under a light microscope.

Immunohistochemical Localization using Light Microscopy

Immunohistochemical localization was carried out following Chye et al. (1999, *Plant J.* 18: 205–214). Floral buds and flowers were fixed with formaldehyde in 50% ethanol for 16 h. The fixed tissues were dehydrated through a series of ethanol solutions (50%, 70%, 80%, 90%, 100%, 100%) for 30 min each, infiltrated with a xylene/Paraplast (Oxford) mixture and then embedded in Paraplast. Ten-μm thick sections were cut on a Leica microtome (Jung RM 2035) and mounted on slides. Slides were dried overnight at 42° C. and incubated in xylene to remove the Paraplast from the sections. The sections were rehydrated by a series of ethanol solutions (100%, 100%, 90%, 80%, 70%, 50%, 30%) and washed twice with water. Sections were incubated for 1.5 h at room temperature in blocking solution [0.1% saponin, 1% bovine serum albumin (BSA), 2% goat serum, 0.3 mM phenylmethylsulfonyl fluoride (PMSF) in phosphate buffered saline (130 mM NaCl, 3 mM $NaH_2PO_4$, 7 mM $Na_2HPO_4$)] and subsequently overnight at 4° C. with anti-peptide polyclonal antibodies raised in rabbit against either SaPIN2a or SaPIN2b, diluted 1:100 (v/v) in blocking solution. The peptides were purchased from Chiron, Clayton, Vic., Australia and the antibodies against SaPIN2a were raised in rabbit according to Sambrook et al.(1989. Molecular Cloning: A laboratory manual. $2^{nd}$ Edition, Cold Spring Harbor Press) while the antibodies against SaPIN2b were purchased from Chiron, Clayton, Vic., Australia. Slides were washed with TTBS (20 mM Tris, 500 mM sodium chloride, 0.05% Tween 20, pH 7.5) and then incubated for 2 h at room temperature with the secondary antibody, biotinylated alkaline phosphatase-conjugated goat anti-rabbit antibody (Bio-Rad) diluted 1:1,500 (v/v) in TTBS. The alkaline phosphatase reaction was carried out as instructed by the supplier (BioRad). The slides were mounted with GelTol (Immunon) aqueous mounting medium and examined under a microscope. Controls included the replacement of rabbit anti-SaPIN2a antibodies or anti-SaPIN2b antibodies with preimmune rabbit serum.

TUNEL Assay

In situ detection of DNA fragmentation was identified using the In situ Cell Death Detection Kit, Fluorescein (Roche). Sections of young buds, mature flowers and senescent flowers were obtained from the Paraplast Plus-embedded material described above. Once hydrated with a decreasing ethanol series, sections were treated with proteinase K (20μg/ml) in phosphate-buffered saline (PBS; 10 mM sodium phosphate, 130 mM NaCl, pH 7.5) for 30 min at 37° C. and rinsed twice in PBS. Fluorescein-labelled nucleotides were attached to the free 3'-OH termini at nicks in fragmented DNA by incubation for 1 h at 37° C. in the presence of terminal deoxynucleotidyl transferase (TdT) according to the manufacturer's instructions. In the positive controls, sections were treated with DNase I (30 U/ml in 50 mM Tris-HCl, pH 7.5, 10 mM $MgCl_2$, 1 g/ml BSA) for 10 min at RT to induce DNA strand breaks, prior to labelling. In negative controls, TdT was omitted. Sections were viewed using a Zeiss LSM 510 inverted laser-scanning microscope.

Immunoelectron Microscopy

*S. americanum* buds were fixed in a solution of 4% paraformaldehyde and 0.5% glutaraldehyde in 0.1 M phosphate buffer (pH 7.2) for 3 h at room temperature. The specimens were then dehydrated in a graded ethanol series, infiltrated in stepwise increments of LR white resin (London Resin Co. Ltd.) and polymerized at 45° C. for 24 h. Materials for immunogold labelling were prepared according to the procedure of Varagona and Raikhel (1994, Immunocytochemistry for light and electron microscopy. In: M. Freeling and V. Walbot (Eds.) The Maize Handbook, Springer-Verlag, N.Y., pp. 149–157), with modifications as described. Specimens (90 nm) were sectioned using a Leica Reichert Ultracut S microtome and mounted on Formvar-coated slotted grids. Grids were incubated in a blocking solution of TTBS containing 1% fish skin gelatin and 1% BSA for 30 min. Anti-SaPIN2a antibodies diluted 1:20 in blocking solution or anti-SaPIN2b antibodies diluted 1:10 in blocking solution were added and incubated overnight at 4° C. Grids were then rinsed three times, each for 5 min, in TTBS. They were incubated for 40 min with 10 nm gold-conjugated goat anti-rabbit IgG secondary antibody (Sigma), diluted 1:20 with blocking solution. Grids were rinsed three times, each for 5 min in TTBS, followed by three 5 min-rinses in distilled water. After staining in 2% uranyl acetate for 15 min followed by 2% lead citrate for 10 min, the sections were visualized and photographed using a Philips EM208 S electron microscope operating at 80 kV. Control sections consist of replacement of the primary antibody with preimmune rabbit serum or blocking solution.

Generation of Transgenic Lettuce Plants Expressing SaPIN2a

The *Agrobacterium tumefaciens*-mediated transformation vector pSa7 containing the SaPIN2a cDNA (FIG. 1*a*; SEQ ID NO:1) was constructed by replacing the GUS gene (Jefferson et al. 1987, *EMBO J.* 6: 3901–3907) in pBI121 (Clontech) with the SaPIN2a cDNA fragment (Xu et al., 2001, *Plant Mol. Biol.* 47: 727–738). The junction region of the CaMV 35S promoter and the SaPIN2a cDNA in pSa7 was sequenced with a primer 5'-CAA TCC CAC TAT CCT TCG CAA GAC C-3' (SEQ ID NO:10) (corresponding to 7372–7396 of CaMV genome; Franck et al., 1980, *Cell* 21: 285–294) to confirm for the absence of any spurious ATG codon between transcription start site (Jefferson et al., 1987, *EMBO J.* 6: 3901–3907) and the SaPIN2a initiator codon. The binary vector pSa7 was then transferred into *A. tumefaciens* LBA4404 by direct transformation (Holsters et al. 1978, *Mol. Gen. Genet.* 163: 181–187). Lettuce transformation was performed as described by Curtis et al. (1994), with modifications, in that petunia nurse cell cultures were omitted in callus-inducing medium and 100 μg/ml of kanamycin sulphate was added to the media for callus induction, shoot regeneration and rooting.

Segregation Analysis of the Progeny ($R_1$) Plants of Transgenic Lettuce

The segregation ratios of kanamycin-resistant ($Km^R$) to kanamycin-sensitive ($Km^S$) plants in the progeny ($R_1$) of the self-fertilization of primary ($R_0$) transgenic lettuce plants were determined by germinating surface-sterilized seeds from each of $R_0$ plants on Murashige and Skoog medium (MS, Murashige and Skoog, 1962, *Physiol Plant* 15: 473–497) containing 100 μg/ml of kanamycin sulphate. After incubation for 2 to 3 weeks in a tissue culture chamber (22–24° C., 12 h light/12 h dark), the seedlings were scored for the kanamycin resistance. The segregation ratios were assessed by Chi-square analysis.

Southern Blot Analysis

Twenty μg DNA, isolated (Dellaporta et al., 1983, *Plant Mol. Biol. Rep.* 1:19–21) from lettuce leaves, were digested with restriction endonucleases, separated by electrophoresis in 0.8% agarose gel and blotted onto Hybond-N membrane (Amersham) according to Sambrook et al. (1989, Molecular Cloning: A Laboratory Manual, Ed. 2. Cold Spring Harbor Laboratory Press, Cold Spring Harbor, N.Y.). The blot was pre-hybridized in 30% deionized formamide, 6×SSC, 5× Denhardt's, 1% SDS, 50 µg/ml denatured, sonicated salmon sperm DNA at 42° C. for 4 h. The random-primed $^{32}$P-labeled SaPIN2a cDNA probe was added and hybridized at 42° C. overnight. The blot was washed in 0.1×SSC, 0.1 % SDS at room temperature.

Northern Blot Analysis

Total RNA was extracted from nightshade plants, wild-type lettuce or transgenic lettuce (Nagy et al., 1988, In: S. B. Gelvin and R. A. Schilperoort (Eds), Plant Molecular Biology Manual, Kluwer Academic Publishers, Dordrecht, pp. B4: 1–29) and analyzed in northern blot analysis as previously described by Xu et al. (2001, *Plant Mol. Biol.* 47: 727–738).

Western Blot Analysis

Total plant protein was extracted according to the procedure of Wu et al. (1997, *Mol. Breeding* 3:371–380). Protein concentration was determined following Bradford (1976, *Anal. Biochem.* 72: 248–254). Total protein was separated by 4–20% gradient SDS-PAGE (Gallagher, 1995, In *Current protocols in protein science*, Vol. 1 (Coligan, J. E., Dunn, B. M., Ploegh, H. L., Speicher, D. W. and Wingfield, P. T., eds.) New York: John Wiley & Sons, Inc., pp. 10.1.17–10.1.23) for western blot analysis (Sambrook et al., 1989, supra) using polyclonal antibodies raised in rabbit against a synthetic peptide (GESDPRNPKDC) (SEQ ID NO:8) corresponding to amino acids 77 to 87 of SaPIN2a (FIG. 1b; SEQ ID NO:2) (Xu et al., 2001, *Plant Mol. Biol.* 47: 727–738). The Amplified Alkaline Phosphatase Immun-Blot Assay Kit (Bio-Rad) was used to detect cross-reacting bands.

Trypsin and Chymotrypsin Inhibitory Activity and Endogenous Trypsin- and Chymotrypsin-Like Activity Assays Total plant proteins extracted with 50 mM Tris, pH 8.1, 20 mM CaCl$_2$ were used for spectrophotometric assays of trypsin or chymotrypsin inhibitor activity as described by Kollipara and Hymowitz (1992, *J. Agric. Food Chem.* 40, 2356–2363).

For the trypsin inhibitor activity assay, 150 µl of leaf extract was pre-incubated for 3 min at room temperature (RT) in a quartz cuvette (10-mm path length, 3.5-ml capacity) with 100 µl of bovine trypsin (10 µg/ml in 1 mM HCl, Calbiochem Cat. No. 6502) and assay buffer (46 mM Tris-HCl, pH 8.1, 11.5 mM CaCl$_2$), to give a final volume of 1.5 ml. The reaction was initiated by the addition of 1.5 ml of substrate [2 mM p-toluenesulfonyl-L-arginine methyl ester (TAME, Sigma Cat. No. T4626) in assay buffer] to the pre-incubation mixture. The recording of absorbance at 247 nm ($A_{247}$) was immediately initiated. The spectrophotometer was set to auto-zero just before the start of recording and the absorbance was measured at 30-sec intervals for 3 min. In the standard reaction, 100 µl of bovine trypsin (10 µg/ml in 1 mM HCl) was pre-incubated with 1.4 ml of assay buffer without inhibitor. For the chymotrypsin inhibitor activity assay, 50 µl of leaf extract was pre-incubated for 3 min at RT with 100 µl of bovine α-chymotrypsin (20 µg/ml in 1 mM HCl, Calbiochem Cat. No. 230832) and assay buffer (0.1 M Tris-HCl, pH 7.8, 0.1 M CaCl$_2$), to give a final volume of 1.5 ml. To start the reaction, 1.5 ml of substrate [1 mM N-benzoyl-L-tyrosine ethyl ester (BTEE, Sigma Cat. No. B6125) in 50% (w/w) methanol] were added and mixed with the pre-incubation mixture. The absorbance at 256 nm ($A_{256}$) was monitored like that of trypsin described above. In the standard reaction, 100 µl of chymotrypsin (20 µg/ml in 1 mM HCl) was pre-incubated with 1.4 ml of assay buffer without inhibitor.

Endogenous trypsin- and chymotrypsin-like activities in leaves of wild-type and transgenic R$_1$ lettuce plants were determined using the same procedures as in proteinase inhibitory activity assays, with the omission of bovine trypsin or chymotrypsin from the reaction.

Insect Feeding Experiments

Insect feeding trials were carried out as described by Johnson et al. (1989, *Proc. Natl. Acad. Sci.* USA 86, 9871–9875). The larvae of cabbage looper (*Trichoplusia ni*) were reared on lettuce grown in growth chamber (16 h light, 20±2° C.) until pupation. Their pupae were collected and put into a box with a net to give rise to adults. The moths were fed with 5% honey obtained from the local market. The eggs were collected and hatched in Petri dishes. The first and second instar larvae were used for the experiments. Detached lettuce leaves from wild-type and transgenic plants were placed on top of 3 sheets of Whatman No. 1 papers (125 mm diameter) wetted with 6 ml of distilled water in sterile Petri dishes (145 mm diameter). Ten first or second instar larvae of *T. ni* were put into each dish and incubated in plant growth chamber (20±2° C.). Each day, the larvae were weighed and transferred with a brush to new dishes containing fresh leaves.

Plasmid Construction for Plastid Transformation

Plasmid pMLVHisP utilizes the tobacco plastid genome sequences spanning rbcL-accD to target SaPIN2a into the chloroplast genome by homologous recombination. The promoter ($P_{psbA}$) and terminator ($T_{psbA}$) for SaPIN2a are derived from the rice plastid gene psbA (Reddy et al., 2002, *Mol Breeding* 9: 259–269); the psbA gene encoding the photosystem II 32 kD protein. The selectable marker gene aadA, which specifies spectinomycin-resistance, is driven from the rice plastid 16S rRNA operon (rrn) promoter ($P_{rrn}$) and terminated by the rbcL terminator ($T_{rbcL}$).

The SaPIN2a plastid expression vector pMLVHisP was generated from plasmid vector pMLVHisA (FIG. 18). A 0.5-kb NotI fragment of *S. americanum* cDNA encoding proteinase inhibitor II protein SaPIN2a was cloned in the NotI of pMLVHisA, with $(His)_5$ (SEQ ID NO: 16) and SaPIN2a fused in-frame, to produce plasmid pMLVHisP (FIG. 19).

Plastid Transformation of *Nicotiana tabacum* cv. Xanthi

Plastid transformation was carried out following Svab and Maliga (Svab et al., 1993, *Proc. Natl. Acad. Sci. USA* 90: 913–917) by bombardment of leaves with tungsten particles coated with the desired DNA (pMLVHisP). Aseptical seeds were germinated on Murashige and Skoog (MS) medium (Murashige and Skoog, 1962, *Physiol. Plant.* 15: 473–497), supplemented with agar (5 g/liter) and sucrose (30 g/liter). For bombardment, leaves were placed abaxial side facing up on RMOP medium containing MS salts, 6-benzylaminopurine (1 mg/liter), α-naphthalene acetic acid (0.1 mg/liter), thiamine (1 mg/liter), myo-inositol (100 mg/liter), agar (5 g/liter) at pH 5.7 and sucrose (30 g/liter). Bombardment was carried out using the particle delivery system, PDS 1000-He (Bio-Rad) and its accessories. Tungsten particles (M17) were coated with pMLVHisP DNA and leaves bombarded. After bombardment, leaves were cut into small pieces and placed on RMOP selection medium containing spectinomycin dihydrochloride (500 mg/liter). Transformants were passaged for five more cycles in the selection medium to obtain homoplastomic plastid-containing plants.

Screening of the Plastid-Transformed Tobacco for Integration of SaPIN2a cDNA

A primary PCR screen was performed with total DNA extracted from individual lines of the green spectinomycin-resistant shoots rooting on spectinomycin-containing RMOP medium. Oligonucleotide primers (ML330P: 5'GTCTATAT-TATACTGTTAAATAACAAGCC3' (SEQ ID NO:11), ML399: 5'GAGAATCCACCATGGCTCATCATCAT-CATCATCATATGGCTGTTCACAAAGTT AGC3' (SEQ ID NO:12), ML400: 5'GAGCGGCCGCTTAGAAATAAG-CAGTGG3' (SEQ ID NO:13) and ML422: 5'CGATACT-TCGGCGATAACCGC3' SEQ ID NO:14)) were used in PCR amplification. Each PCR reaction (25 µl) consisted of 25 ng DNA, 10 pmol of each primer, 1 U Taq polymerase (Perkin Elmer), 2.5 µl of 25 mM $MgCl_2$ and 0.25 µl each of 10 mM dNTPs. PCR amplification was initiated with denaturation at 95° C. for 3 min, followed by 36 cycles of 94° C. for 30 sec, 57° C. for 30 sec and 68° C. for 2 min, and extension at 72° C. for 10 min. The PCR products were separated by electrophoresis on a 0.8% agarose gel and DNA was transferred to a nylon membrane (Hybond-N, Amersham) according to Sambrook et al. (1989. Molecular Cloning: A Laboratory Manual. Cold Spring Harbor Laboratory Press, Cold Spring Harbor). The blot was prehybridized in 30% deionized formamide, 6×SSC, 5× Denhardt's solution, 1% SDS, 500 µg/ml denatured salmon sperm DNA at 42° C. for 6 h and hybridized overnight at 42° C. to a random-primed $^{32}P$-labeled SaPIN2a probe. The blot was washed in 0.1×SSC, 0.1% SDS at 65° C. for 15 min.

6.2 Results

Isolation of a Complete-Length *S. americanum* cDNA Encoding SaPIN2b

The 532-bp SaPIN2b cDNA (GenBank accession number AF209709) we previously identified (Xu et al., 2001, *Plant Mol. Biol.* 47: 727–738) consists of 328-bp coding region and 204-bp 3'-untranslated region. To obtain the remaining 5'-end of the SaPIN2b cDNA, the SMART RACE cDNA Amplification Kit was used with the universal primer mix and a SaPIN2b-specific primer located within the coding region of the SaPIN2b cDNA sequence. The resultant 0.35-kb fragment was PCR-amplified and cloned into plasmid pGEM-T for DNA sequence analysis. The full-length SaPIN2b cDNA (SEQ ID NO:3) consists of 32-bp 5'-untranslated region, 456-bp coding region and 204-bp 3'-untranslated region (GenBank AF209709). SaPIN2a and SaPIN2b cDNAs share 78.5% nucleotide identity and 74.3% deduced amino acid sequence identity. The DNA sequences and amino acid sequences were analyzed using the Wisconsin Package Version 10.0 of the Genetics Computer Group (1999).

Expression Patterns of SaPIN2a and SaPIN2b

Northern Blot Analysis of SaPIN2a and SaPIN2b Expression During Floral Development Northern blot analysis of total RNA from young buds, mature buds, open flowers, old flowers and senescent flowers using SaPIN2a- or SaPIN2b-specific probes, that share 63.36% identity, were carried out to investigate the expression pattern of SaPIN2a and SaPIN2b mRNAs during floral development (FIG. 3). Results show that expression of SaPIN2a and SaPIN2b mRNAs decreases as the flower matures and senescence begins (FIG. 3, lanes 1–5). In both cases, lower expression occurred in old and senescent flowers (FIG. 3, lanes 4–5). With SaPIN2b, decreased expression was observed earlier, following bud maturation.

Western Blot Anaylsis of SaPIN2a and SaPIN2b in *S. americanum* Flowers

Western blot analysis using SaPIN2a- or SaPIN2b-specific polyclonal antibodies detected SaPIN2a (FIG. 4, lanes 1–2) and SaPIN2b (FIG. 4, lanes 3–4) cross-reacting bands of apparent molecular mass of 16.7 kDa in *S. americanum* floral buds (lanes 1, 3) and open flowers (lanes 2, 4). The apparent molecular mass of SaPIN2a is consistent with our previous estimation (Xu et al., 2001, *Plant Mol. Biol.* 47: 727–738). In both cases, consistent with results from northern blot analysis (FIG. 3), the cross-reacting bands were stronger in floral buds (FIG. 4, lanes 1, 3) than in mature open flowers (FIG. 4, lanes 2, 4).

Localization of SaPIN2a and SaPIN2b mRNA in Flowers

Figure 5:
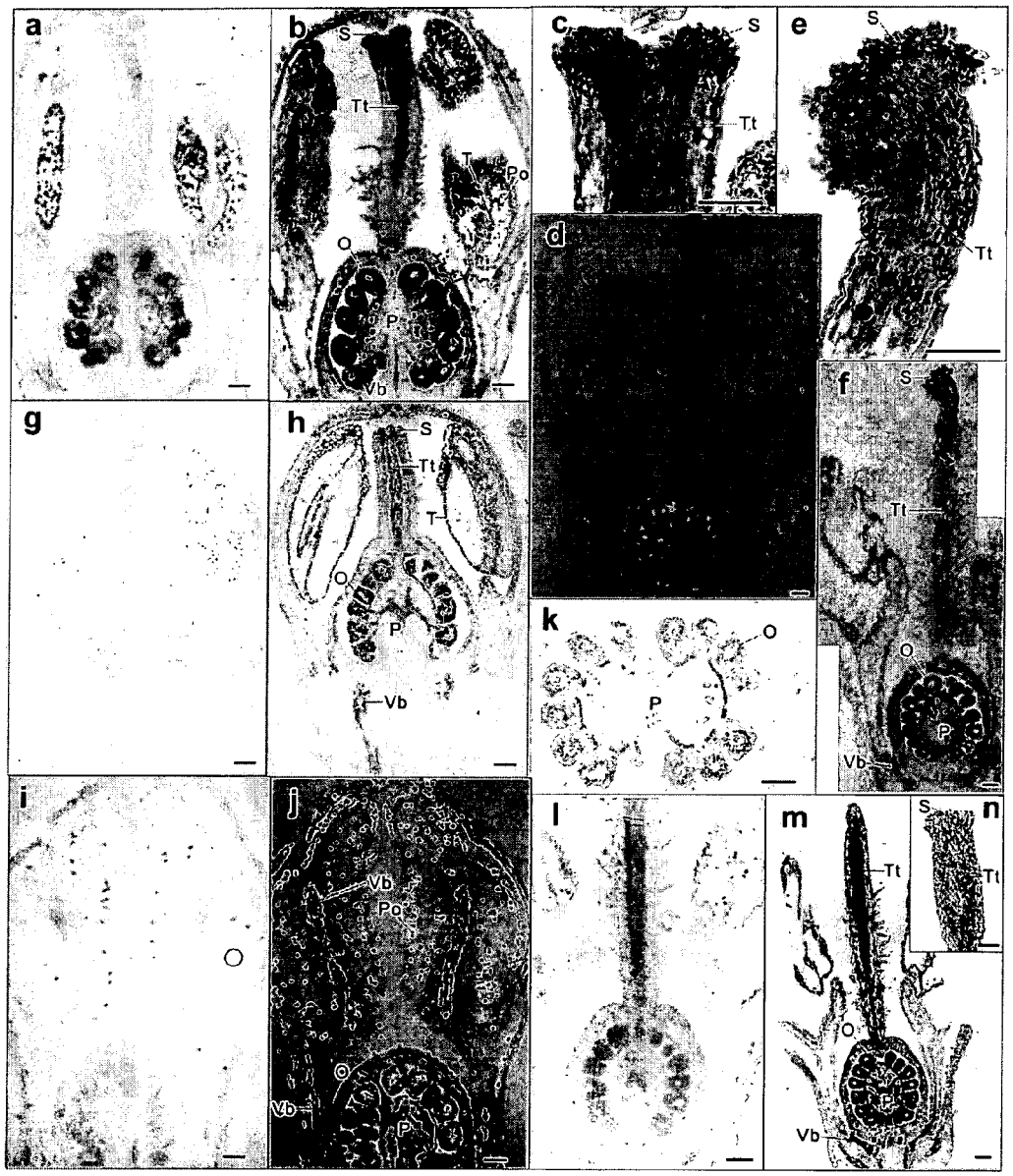
Figure 6:
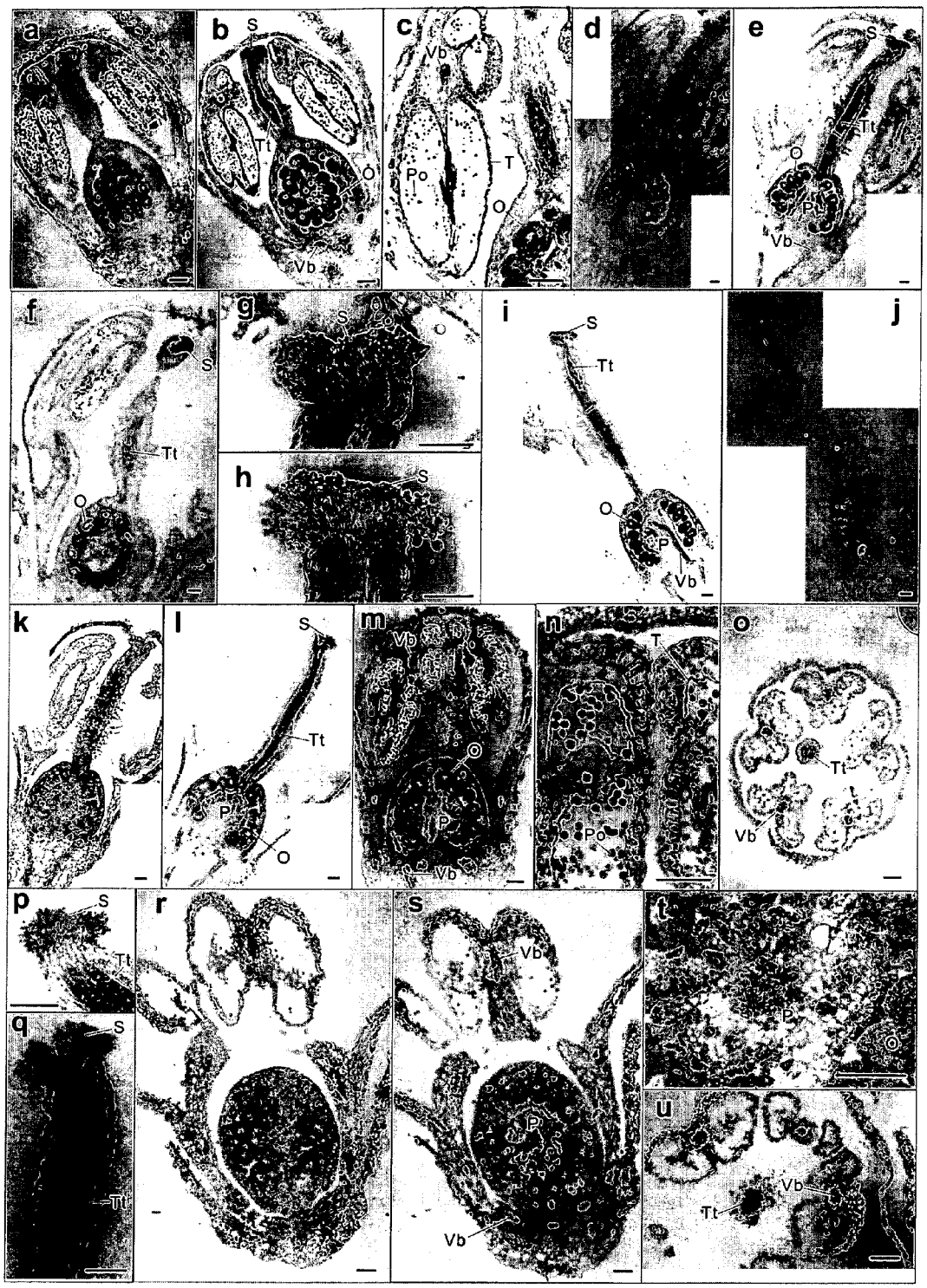
Figure 7:
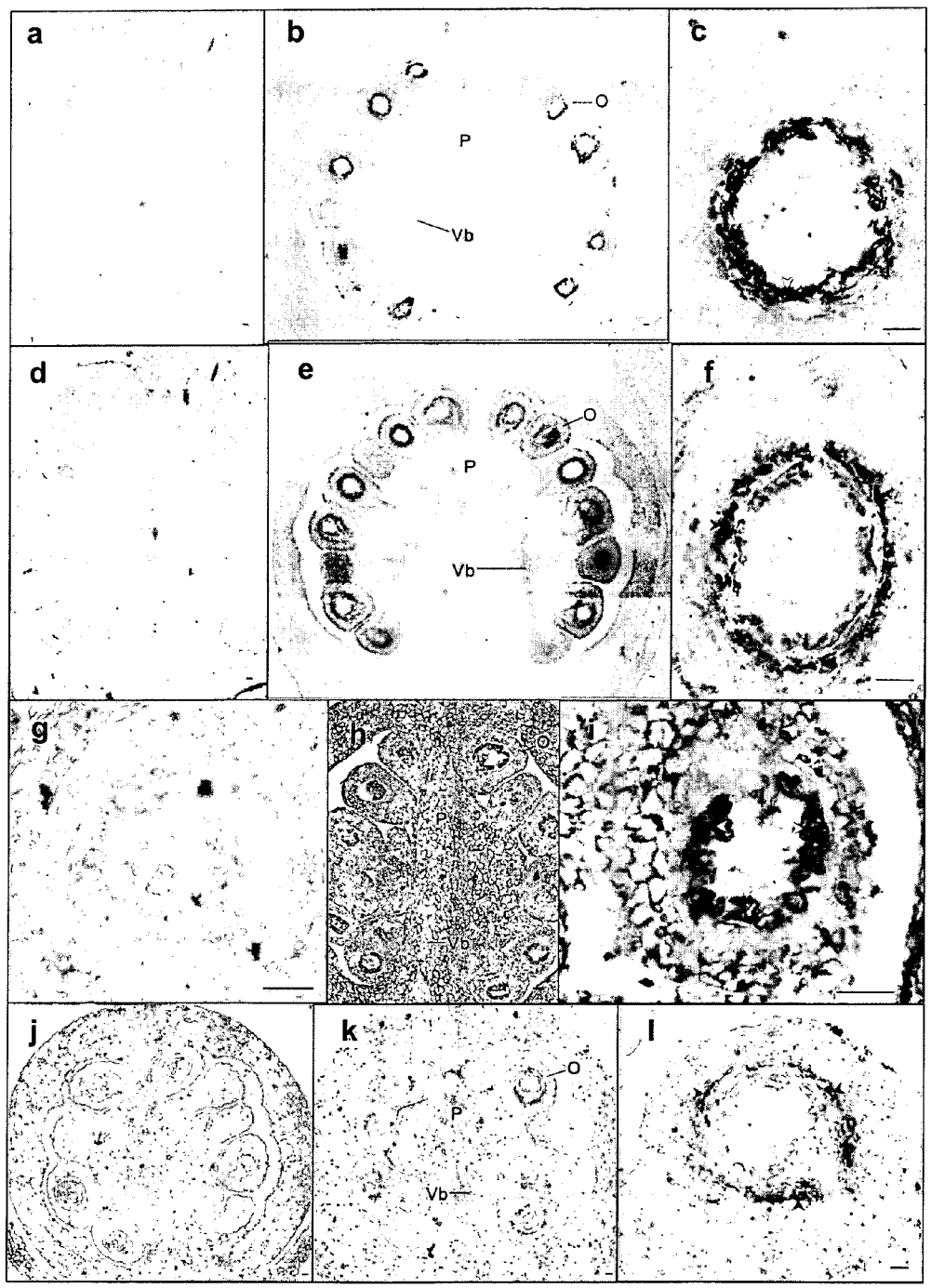

To further investigate the expression of SaPIN2a and SaPIN2b in floral buds, open flowers and senescent flowers, in situ hybridization studies were carried out using antisense SaPIN2a- and SaPIN2b-specific RNA probes (FIGS. 5, 6 and 7). These probes share only 63.36% nucleotide sequence identity. Using the sense RNA probe as control (FIG. 5a, d), SaPIN2a mRNA accumulated in the stigma, stylar transmitting tissue, vascular bundles, pollen, tapetum, nucellar cells of the ovule and the outermost cell layer of the placenta (FIG. 5b, c) in the young floral bud (−72 h stage, FIG. 3). In the open flower (0 h stage, FIG. 5), SaPIN2a mRNA was expressed in the stigma, stylar transmitting tissue, vascular bundles, nucellar cells of the ovule and the outermost cell layer of the placenta (FIG. 5e, f) but expression in the tapetum was lacking.

Using the sense RNA probe as control (FIG. 6a, d, j), in young (FIG. 6b, c) and mature buds (FIG. 6e–g), SaPIN2b mRNA was detected in the stylar transmitting tissue, vascular bundles, nucellar cells of the ovule and the outermost cell layer of the placenta. In the young bud, SaPIN2b mRNA was also expressed in pollen and tapetum, but not in stigma (FIG. 6b, c), unlike in mature bud where expression in stigma was clearly visible (FIG. 6e–g). In the open flower (FIG. 6h, i), SaPIN2b mRNA expression was similar to that in mature buds (FIG. 6e, f) and that of SaPIN2a mRNA expression in open flowers (FIG. 5e, f). In senescent flowers, using sense RNA probes as controls (FIGS. 7a and d), we localized SaPIN2a (FIG. 7b, c) and SaPIN2b (FIG. 7e, f) mRNAs in the inner cell layers of the embryo sac. While SaPIN2a (FIG. 7b, c) mRNA was confined to the innermost layer, SaPIN2b (FIG. 7e, f) expression was detected just beneath the innermost cell layer of the embryo sac.

Localization of SaPIN2a and SaPIN2b Proteins in Flowers

Immunolocalization of SaPIN2a and SaPIN2b in flowers was carried out using affinity-purified SaPIN2a- and SaPIN2b-specific antibodies (FIGS. 5, 6 and 7). In floral buds, SaPIN2a (FIG. 5h, j) and SaPIN2b (FIG. 6l–p) were detected in the stylar transmitting tissue, vascular bundles, nucellar cells of the ovule and the outermost cell layer of the placenta. SaPIN2a (FIG. 5h) and SaPIN2b (FIG. 6n) were also detected in the tapetum of young floral buds but were absent in the tapetum of mature buds (FIGS. 5j, 6o). In open flowers, SaPIN2a accumulated in the stigma, stylar transmitting tissue, vascular bundles, nucellar cells of the ovule and the outermost cell layer of the placenta but not in pollen or tapetum (FIG. 5m, n). In the mature bud and open flower, SaPIN2b was detected only in the stylar transmitting tissue, vascular bundles and the outermost cell layer of the placenta (FIG. 6l, o, s–u). Unlike SaPIN2a, SaPIN2b expression was not detected in stigmas and developing ovules of young bud (FIG. 6p), mature bud (FIG. 6l) or open flower (FIG. 6q). Nonetheless, SaPIN2b was detected in the tapetum of the young bud (FIG. 6n) and in the vascular bundles of the young bud (FIG. 6m), mature bud (FIG. 6o) and open flower (FIG. 6s, u). In senescent flowers, using preimmune sera in control sections (FIGS. 7g and j), SaPIN2a (FIG. 7h, i) and SaPIN2b (FIG. 7k, l) were immunolocalized to the innermost cell layer of the embryo sac and the layer beneath this, respectively, corresponding to the localization in tissues as their mRNA.

Detection of in situ Nuclear DNA Fragmentation During PCD

Localization of PCD, as indicated by DNA fragmentation in nuclei, on floral sections of young buds, mature flowers and senescent flowers was verified using the TUNEL assay. TUNEL signals, i.e., green fluorescence, were absent in the negative controls (FIG. 8a, c, f, h, j) in which TdT was omitted. A similar pattern in the absence of green fluorescence was seen in young floral buds (FIG. 8b, d) and mature flowers (FIG. 8g, i). In contrast, green fluorescence was observed in the DNase I-treated positive control sections (FIG. 8e, n). In the ovaries of senescent flowers, green fluorescence was detected in the vascular bundle, ovules and the outermost layer of the placenta (FIG. 8k). At higher magnification of the ovule, TUNEL positive nuclei were visible in cells at the outermost layer of the placenta and nucellar cells, with the exception of the innermost cell layer in the embryo sac (FIG. 8l, m). This layer of cells in the DNase I-treated positive control shows green fluorescence (FIG. 8n). In young floral buds (FIG. 8d) and mature flowers (FIG. 8i), the nuclei of cells in the ovules and at the outermost layer of the placenta were TUNEL negative.

Immunogold Labelling of SaPIN2a and SaPIN2b in *S. americanum* Ovule

To determine the subcellular localization of SaPIN2a and SaPIN2b in the ovule, immunoelectron microscopy was carried out using floral buds of *S. americanum*. Results obtained on the transverse sections of the ovule showed that SaPIN2a (FIG. 9a–c) and SaPIN2b (FIG. 9d–i) were immunolocalized to the vacuoles in the nucellar cells. Immunogold particles were lacking in the nucleus (FIG. 9i). In comparison, immunogold labelling was absent in the controls in which preimmune serum for SaPIN2a (data not shown) or SaPIN2b (FIG. 9j–k) was used or when the primary antibody was replaced with blocking solution (FIG. 9l–m).

Transformation of Lettuce with pSa7 Containing SaPIN2a cDNA

Figure 10B:
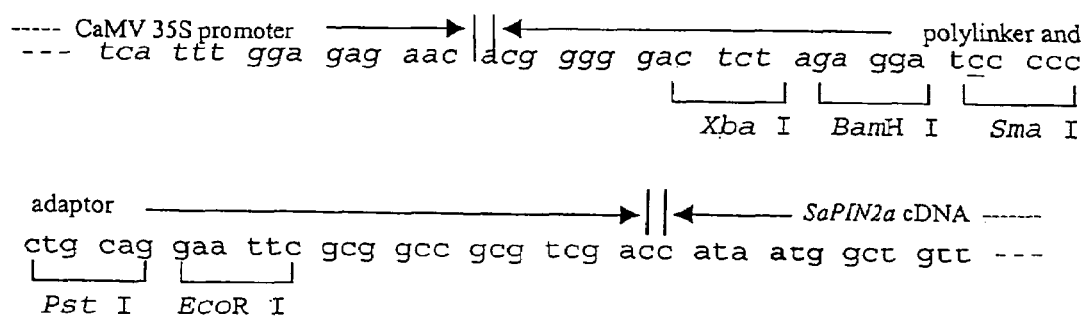

FIG. 10a shows the binary vector pSa7 used in lettuce transformation. The expression of SaPIN2a cDNA is driven by the Cauliflower Mosaic Virus (CaMV) 35S promoter. DNA sequence analysis at the junction of the CaMV 35S promoter and the SaPIN2a cDNA in pSa7 confirmed the absence of any spurious ATG codon between the transcription start site (Jefferson et al., 1987, *EMBO J.* 6: 3901–3907) and the SaPIN2a initiator codon (FIG. 10b). *A. tumefaciens* LBA4404 harboring pSa7 was used to transform lettuce and transformants were selected on kanamycin-containing media.

Southern Blot Analysis of Transgenic Lettuce

To confirm the integration of the SaPIN2a cDNA into the lettuce genome and to estimate the copy number of the transgene in different transgenic lines, Southern blot analyses were performed with a $^{32}$P-labeled SaPIN2a cDNA probe.

Results of Southern blot analysis with EcoRI-digested DNA extracted from putative transgenic and regenerated ($R_0$) lettuce plants is shown in FIG. 11a. The presence of an expected 0.58-kb EcoRI fragment (indicated by arrow in FIG. 11a) in all transgenic lines (FIG. 11a, TL1, 7, 11, 15 and 33) suggests integration of the SaPIN2a cDNA. This band was lacking in wild-type (FIG. 11a, lane WT). Additional strong hybridization bands in TL7 and 33 suggest incomplete EcoRI digestion of genomic DNA or the presence of rearranged copies of the SaPIN2a cDNA in the genome of these transgenic lettuce lines. Rearrangements of the transgene have been observed previously in many other transgenic plants (Jorgensen et al., 1987, *Mol. Gen. Genet.* 207:471–477; Deroles and Gardner, 1988, *Plant Mol. Biol.* 11, 365–377; Radke et al., 1988, *Theor. Appl. Genet.* 75: 685–694; Lee et al., 1999, *Molecular Breeding* 5: 1–9).

Since only one BamHI site is present between the 35S promoter and the SaPIN2a cDNA within the T-DNA region of pSa7 (FIG. 10a), the number of bands observed in the Southern blot of BamHI-digested genomic DNA probed with a $^{32}$P-labeled SaPIN2a cDNA fragment should give a good estimation of the transgene copies integrated into lettuce genomic DNA. The different hybridization patterns of BamHI-digested DNA shown in FIG. 11b suggest these transgenic plants resulted from independent transformation events, and also revealed that the number of strong bands which hybridized to SaPIN2a cDNA probe ranged from one (TL1, 2, 10, 11, 12, 14, 20, 43) to four (TL34 and 52) corresponding to single or multiple copies of the transgene in these lines. Single copies of the transgene in TL1 and 11 and multiple copies of the transgene in TL33 were further confirmed by segregation analysis of their progenies (Table 1).

TABLE 1

Segregation of NPT-II gene (kanamycin resistance) in the progeny of transgenic lettuce plants.

| Parent transgenic line ($R_0$) | Progeny ($R_1$) plants[a] | | Expected ratio[b] | | |
|---|---|---|---|---|---|
| | Kan$^R$ | Kan$^S$ | (Kan$^R$:Kan$^S$) | Chi-square | Probability |
| TL1 | 67 | 21 | 3:1 | 0.061 | 1.000 |
| TL11 | 30 | 10 | 3:1 | 0.000 | 1.000 |
| TL33 | 176 | 3 | 255:1 | 7.587 | 0.667 |
| | | | 63:1 | 0.015 | 1.000 |

[a]Kan$^R$ = kanamycin-resistant; Kan$^S$ = kanamycin-sensitive;
[b]Ratio 3:1 is for a single function locus, 255:1 for four functional loci and 63:1 for three functional loci.

Expression of SaPIN2a mRNA in Transgenic Lettuce

The transcription of SaPIN2a in transgenic lettuce plants was examined by northern blot analysis. Total RNA, isolated from leaves of $R_0$ transgenic lettuce identified in Southern blot analysis (FIG. 11) and from wild-type plants, was hybridized to the SaPIN2a cDNA probe. As shown in FIG. 12, SaPIN2a mRNA was detected in most transgenic lines, with the exception of TL14, and no signal was present in the RNA from leaves of wild-type plants. The size of most SaPIN2a transcripts in transgenic lettuce (0.93 kb, indicated by an arrow in FIG. 12) is slightly larger than that of endogenous transcript of 0.67 kb in *S. americanum* (indicated by an arrowhead in FIG. 12 lane Sa) due to about 0.26 kb from the NOS-terminator (FIG. 10a). A more complex mRNA expression pattern was observed in the $R_1$ transgenic lines, with the presence of a shorter transcript below the expected 0.93-kb band (FIG. 13a). It is worth noting that the shorter transcript found in leaves of some $R_0$ plants (FIG. 12) became more prominent in leaves of $R_1$ plants (FIG. 13a).

Non-Detection of SaPIN2a Protein in Transgenic Lettuce by Western Blot Analysis

Total leaf proteins were extracted from leaves of $R_0$ transgenic plants that showed SaPIN2a mRNA accumulation in northern blot analysis (FIG. 12) and wild-type plants for western blot analysis with affinity purified SaPIN2a-specific antibodies. No SaPIN2a protein could be detected in the leaves of these $R_0$ transgenic plants in western blot analysis despite detection of SaPIN2a mRNA in northern blot analyses. Western blot analysis was also carried out with total proteins extracted from the progeny ($R_1$) plants of three self-pollinated $R_0$ transgenic plants (TL1, 11 and 33) as well as the progeny of self-pollinated regenerated wild-type plants. FIG. 13 shows the results of western blot analysis of total proteins prepared from $R_1$ transgenic plants, together with the corresponding results of northern blot analysis of total RNA prepared from identical tissue samples. Although very high levels of SaPIN2a mRNA accumulated in the leaves of these transgenic plants (FIG. 13a), again no protein band corresponding to SaPIN2a in *S. americanum* stem was detected in transgenic lettuce leaves (FIG. 13c). Some non-specific cross-reacting bands were found and one of them (18.1 kDa), present in lettuce leaves but not stems, is very close to the size of native SaPIN2a (16.7 kDa) (FIG. 13c). Since native SaPIN2a in *S. americanum* accumulates in stem (Xu et al., 2001, *Plant Mol. Biol.* 47: 727–738), the cellular transport of SaPIN2a might account for its apparent absence in transgenic lettuce leaves. To investigate this possibility, northern blot and western bolt analyses were carried out with samples from stems of transgenic lettuce plants. Although SaPIN2a mRNA was detected in their stems (FIG. 13a) at lesser amounts than leaves, SaPIN2a protein remained undetected in both, on western blot with SaPIN2a-specific antibodies (FIG. 13c).

Trypsin and Chymotrypsin Inhibitory Activities and Endogenous Trypsin- and Chymotrypsin-Like Activity Assays Although the SaPIN2a coding sequence in pSa7 was confirmed by DNA sequencing (FIG. 10b), the integration of SaPIN2a cDNA in transgenic lines, by Southern blot analysis (FIG. 11) and SaPIN2a mRNA by northern blot analysis (FIGS. 12–13), the SaPIN2a protein was undetectable upon western blot analysis. The relatively low sensitivity of western blot analysis may have resulted in the failure to detect SaPIN2a protein in transgenic lettuce. Based on the quantitative assays of *Bacillus thuringiensis* (B.t.) protein expressed in transgenic plants using three assay methods (bioassay, ELISA and western blot analysis), it has been shown that the western blot analysis is the least sensitive assay, although it is the most frequently used (Fuchs et al., 1990, In *ACS Symposium Series No.432, Analytical Chemistry of Bacillus thuringiensis*. pp 105–113). Hence we further examined the presence of SaPIN2a in transgenic lettuce by using proteinase inhibitory activity assays, which may be more sensitive than western blot analysis.

Crude leaf extracts prepared from leaves of $R_1$ transgenic and wild-type plants were tested for inhibitory activity against bovine trypsin and chymotrypsin. Results of trypsin inhibitory activity assays (FIG. 14a) showed no significant inhibitory activity against bovine trypsin in transgenic lettuce. Leaf extracts from all three transgenic lines analyzed (TL1, 11 & 33) showed trypsin activity similar to the standard reaction. Surprisingly, leaf extracts of wild-type plants had much higher trypsin activity than the standard reaction containing bovine trypsin (FIG. 14a). In the case of chymotrypsin inhibitory activity assays (FIG. 14b), all reactions containing leaf extracts from both transgenic and wild-type plants showed higher chymotrypsin activity than the standard, while the transgenic plants had slightly decreased activity compared with wild-type plants. These results of the inhibitory activity assays suggest that lettuce leaves might possess considerable endogenous trypsin- and chymotrypsin-like activities.

Accordingly, the endogenous trypsin- and chymotrypsin-like activity in leaves of wild-type and transgenic $R_1$ lettuce plants were determined using the same procedures for above proteinase inhibitory activity assay except that no bovine trypsin or chymotrypsin was added to the reaction. The results of these experiments are shown in FIG. 15. As expected, both endogenous trypsin- and chymotrypsin-like activities were detected in leaf extracts from wild-type lettuce plants. The results of assays on leaves from transgenic plants, however, are unexpected and interesting. The endogenous trypsin-like activity in all three transgenic plants was almost completely inhibited (FIG. 15a), while the endogenous chymotrypsin-like activities in these transgenic plants moderately decreased (FIG. 15b). The inhibition of endogenous trypsin- and chymotrypsin-like activities in transgenic lettuce leaves suggests that SaPIN2a protein accumulates in transgenic lettuce at amounts that are undetectable by western blot analysis but that could inhibit the endogenous trypsin- and chymotrypsin-like activities.

Preliminary Insect Feeding Assay with Primary Transgenic Lettuce Plants

Since transgenic plants expressing potato or tomato PIN2 show the enhanced resistance to herbivorous insects (Johnson et al., 1989, *Proc. Natl. Acad. Sci.* USA 86: 9871–9875; Duan et al., 1996, *Nat. Biotech.*, 14:494–498; Klopfenstein et al., 1997, *Biomass and Bioenergy* 12:299–311), transgenic lettuce plants expressing SaPIN2a were tested for their protection against the cabbage looper (*Trichoplusia ni*), a very destructive lettuce pest (Barbour, 1999, Vegetable crops: search for arthropod resistance in genetic resources. In Global plant genetic resources for insect-resistant crops (Clement, S. L. and Quisenberry, S. S., eds.). Boca Raton: CRC Press, pp. 171–189).

Due to limited availability of the larvae at the same developmental stage, all of the feeding trials could not be carried out concurrently. The experiments shown in FIG. 16 were performed separately, each trial with its own set of control. Larvae fed on leaves from TL1 and TL11 plants (FIGS. 16a & c) grew significantly slower than those fed on control leaves, with a 49.8% and 37.7% reduction in larval weight respectively after feeding for 8 days. A moderate reduction (25.5% on day 9) in larval growth was observed with TL15 (FIG. 16d), while growth was not retarded when larvae were fed on TL7 leaves (FIG. 8b). FIG. 17 shows the growth of larvae fed on leaves of TL1 was arrested and the larvae consumed much less leaf tissue compared to the larvae fed on leaves of wildtype lettuce. There is considerable variability of the growth of larvae fed even on leaves from wild-type plants was observed in four independent trials presented in FIG. 9.

Plastid Transformation of Tobacco with Plasmid pMLVHisP

Plastid transformation of tobacco with plasmid pMLVHisP (FIG. 19), a derivative of vector pMLVHisA (FIG. 18), yielded several green shoots on selective medium (FIG. 20a). From these regenerated tobacco plantlets, total DNA was extracted for PCR analysis using primers ML330P and ML400 (FIG. 20b). The results of PCR analysis showed the presence of an expected 0.63-kb band on agarose gel electrophoresis (FIG. 20c). Subsequently, Southern blot analysis using a $^{32}$P-labeled S1 probe confirmed the presence of one transplastomic line (FIG. 20d).

6.3 Discussion

Although PCD occurs in various tissues within the plant reproductive organs (Wu and Cheung, 2000, *Plant Mol Biol* 44: 267–281), little is known of the identities and roles of participating proteinases and their corresponding proteinase inhibitors. Cysteine proteinases and their inhibitors have been shown to modulate PCD induced by oxidative stress and pathogen attack (Solomon et al., 1999, *Plant Cell* 11: 431–443). The expression of cysteine proteinase in brinjal (*S. melongena*) coincides with developmental events associated with PCD (Xu and Chye, 1999, *Plant J.* 17: 321–327). Others have observed cysteine proteinase expression has also been observed during petal senescence in carnation (Jones et al., 1995, *Plant Mol. Biol.* 28: 505–512) and day-lily (Guerrero et al., 1998, *Plant Mol. Biol.* 36: 565–571). In contrast, evidence is lacking for the role of serine proteinases other than the subtilisins (reviewed in Beers et al., 2000, *Plant Mol. Biol.* 44: 399–415), or their inhibitors in PCD. Hence, to better understand the role of serine proteinase inhibitors SaPIN2a and SaPIN2b in regulating developmental PCD in flowers, the localization of their mRNAs and corresponding proteins were investigated. The occurrence of developmental PCD in floral sections at various stages in development was verified by TUNEL assays that detect in situ nuclear DNA fragmentation, a hallmark of PCD.

A correlation was observed between results of northern blot and western blot analyses. Both SaPIN2a and SaPIN2b mRNAs and proteins showed the highest expression during early floral development. In situ mRNA hybridization and immunolocalization located their expression to floral tissues destined to undergo developmental PCD, suggesting that these serine proteinase inhibitors could have an endogenous role in impeding PCD during flower development. The ectopic expression of SaPIN2a from the Cauliflower Mosaic Virus promoter results in the inhibition of endogenous trypsin- and chymotrypsin-like activities in transgenic lettuce, suggesting of an endogenous role in the regulation of serine proteinases.

PIN2 mRNA expression has been detected in potato floral buds and tomato flowers (Pena-Cortes et al., 1991, *Plant Cell* 3: 963–972) and PIN2-like mRNAs, in tomato floral buds (Brandstater et al., 1996, *Mol. Gen. Genet.* 252: 146–154) and tobacco stigmas (Atkinson et al., 1993, *Plant Cell* 5: 203–213). The expression of SaPIN2a and SaPIN2b parallels that of PIN2 in potato and tomato flowers on northern blot analysis (Pena-Cortes et al., 1991, *Plant Cell* 3: 963–972). While PIN2 expression in potato flowers was developmentally confined to floral buds, tomato PIN2 mRNA accumulated in all organs of the mature flower (Pena-Cortes et al., 1991, *Plant Cell* 3: 963–972). Further analysis of potato PIN2 expression in floral buds using a PIN2 promoter-β-glucoronidase fusion in transgenic potato revealed that highest expression occurred in the developing ovules and in the adjacent outermost cell layer of the placenta in young floral buds (Pena-Cortes et al., 1991, *Plant Cell* 3: 963–972). Interestingly, this expression pattern in the ovules and adjacent placenta cell layer, is mimicked by SaPIN2a and SaPIN2b mRNAs in *S. americanum* floral buds and open flowers. Correspondingly, SaPIN2a protein was immunolocalized to the same tissues as its mRNA. However, SaPIN2b was not detected in ovules despite its accumulation in the outermost cell layer of the placenta, possibly due to its lower steady-state levels in ovules. The differential accumulation of SaPIN2a and SaPIN2b in developing ovules implicates that their roles in PCD are overlapping but not necessarily identical, and that the anti-peptide antibodies used were specific for each protein.

The development and expansion of the female gametophyte in the ovule is accompanied by the degeneration of nucellar cells (Wu and Cheung, 2000, *Plant Mol. Biol.* 44: 267–281). SaPIN2a and SaPIN2b may play a role in controlling the degeneration of these cells surrounding the gametophyte, and could effectively block the immature degeneration of the two synergid cells surrounding the egg cell and the three antipodal cells before pollination. Depending on the plant species, synergid degeneration occurs during pollen tube elongation or upon the arrival of the pollen tube to the embryo sac (reviewed in Wu and Cheung, 2000, *Plant Mol. Biol.* 44: 267–281). In tobacco, of the same genus *Solanum* as *S. americanum*, degeneration occurs upon presentation of the pollen tubes (Huang et al., 1993, *Planta* 191: 256–264; Huang and Russell, 1994, *Planta* 194: 200–214). Hence, the timely expression of SaPIN2a and SaPIN2b in the ovule before pollination is consistent with this anticipated role.

In young buds and in mature flowers, the presence of SaPIN2a and SaPIN2b in the nucellar cells and the outermost cell layer of the placenta would ensure that protein reserves destined for the nourishment of the embryo is free from proteolysis by serine proteinases. Correspondingly, these tissues in young buds and in mature flowers were TUNEL-negative. In the ovules of senescent flowers, the innermost cell layer of the embryo sac and those beneath it, show expression of SaPIN2a and SaPIN2b, respectively. In these ovules, DNA fragmentation was observed in the nucellar cells, however, reduced TUNEL signals were observed in the innermost cell layers, suggesting that SaPIN2a and SaPIN2b could be protecting the embryo from the PCD-associated proteases within the surrounding nucellar cells. High expression of brinjal cysteine proteinase in nucellar cells has been previously observed (Xu and Chye, 1999, *Plant J.* 17: 321–327) and the expression of barley aspartic protease (Chen and Foolad, 1997, *Plant Mol. Biol.* 35: 821–831) and wheat thiolprotease and carboxypeptidase in the degenerating nucellus has been reported (Dominguez and Cejudo, 1998, *Plant J* 15: 569–574). Thus, the function of the nucellar cells in releasing protein reserves to the embryo is likely dependent on the activities of these proteinases and their inhibitors. That the expression of these proteinase inhibitors precedes the expression of the corresponding proteinases is to be expected. These observations of high PIN2 mRNA in nucellar cells prior to pollination and fertilization suggests a role in protecting the protein reserves from proteolysis for subsequent utilization by the embryo.

Results from in situ hybridization studies also demonstrated that other than the ovules, SaPIN2a and SaPIN2b mRNAs are highly expressed in the transmitting tissue of the style during development from young floral buds to open flowers. In the case of SaPIN2a, but not SaPIN2b, mRNA was also detected in the stigma in the young floral bud, while both mRNAs were located in the stigmas of mature buds and open flowers. This differential expression of SaPIN2a and SaPIN2b in stigmas of young buds again supports their overlapping and complementary roles in floral development. The ability to detect their differential expression also ascertained that the RNA probes used were indeed gene-specific.

It has been suggested that the significance in the stigma-specific expression of a PIN2-like mRNA in *Nicotiana alata* immature and mature pistils is associated with a protective role against pests and pathogens (Atkinson et al., 1993, *Plant Cell* 5: 203–213). In contrast, the expression of SaPIN2a and SaPIN2b was not limited to the stigma and their corresponding detection in other tissues that would undergo PCD suggests that they could also function modulating PCD. Northern blot and western blot analyses of their higher expression in early floral development suggest that they act before pollination and fertilization. The detection of SaPIN2a and SaPIN2b mRNAs in the stigma indicates that they could regulate serine proteinases effectively promoting pollen germination at the stigma and tube elongation in the style of compatible species, while inhibiting those of incompatible ones. Also, the presence of these PIN2 proteins in the style would ensure that PCD is withheld prior to pollination because severe cell degeneration in the transmitting tissue occurs only upon pollen tube elongation (reviewed in Wu and Cheung, 2000, *Plant Mol. Biol.* 44: 267–281). PCD in the transmitting tissue creates space for the elongating pollen tubes which occupy a significant volume and probably provides nutrients to these tubes (Wu and Cheung, 2000, *Plant Mol. Biol.* 44: 267–281). In contrast to SaPIN2a, SaPIN2b was not detected in stigmas of buds and open flowers, like in ovules, despite high mRNA expression in these tissues. Its low steady-state levels in stigmas and ovules could be accountable for this. In comparison, the clear detection of SaPIN2b in the transmitting tissue, the vascular bundles and outermost layer of the placenta of young floral buds, mature bud and open flowers suggests that SaPIN2b possesses differing protein turnover rates in various tissues within the flower.

Expression of SaPIN2a and SaPIN2b mRNA and their corresponding proteins in the tapetum was restricted to the earliest stage in floral development, in the young bud. PCD in the tapetum is essential for pollen grain development and likely occurs in mature buds lacking SaPIN2a and SaPIN2b in their tapetal cells. The tapetum must complete its task in preparing the pollen before its demise, culminated by the absence of protein inhibitors. Expression in pollen of buds indicates a putative role in preventing protein degradation during early pollen development. Expression of SaPIN2a and SaPIN2b in the vascular bundles is likely associated with developmental PCD in these tissues. Indications that SaPIN2a and SaPIN2b could function as modulators in developmentally regulated PCD in *S. americanum* flowers correlate well with our previous findings of an endogenous role for SaPIN2a in regulating proteolysis in the sieve elements (Xu et al., 2001, *Plant Mol. Biol.* 47: 727–738).

Results of immunoelectron microscopy demonstrated that both SaPIN2a and SaPIN2b are subcellularly located within vacuoles in ovule sections. Presumably, in the sieve elements, SaPIN2a is deposited to the parietal cytoplasm following rupture of the tonoplast. The vacuolar targeting of SaPIN2a and SaPIN2b is consistent with computer analysis using the SignalP V1.1 program (described in Nielsen et al., 1999, *Protein Engineering* 12:3–9; Nielsen et al., 1997, *Int J Neural Sys* 8:581–599), which deduced that SaPIN2a and SaPIN2b have cleavable N-terminal signal sequences with cleavage sites after amino acid 27 in SaPIN2a and amino acid 25 in SaPIN2b. Using the PSORT program (described in Nakai et al., 1999, *Trends Biochem Sci.* 24:34–6), both these signal peptides were predicted vacuole-targeting signals.

The instant invention demonstrates the successful production of transgenic lettuce expressing SaPIN2a from the CaMV 35S promoter. Stable integration and inheritance of the SaPIN2a cDNA in the genome of transgenic lettuce were demonstrated by Southern blot analysis and segregation analysis of the $R_1$ progeny. Although SaPIN2a mRNA was detected in both the $R_0$ and $R_1$ transformants by northern blot analysis, western blot analysis using anti-peptide antibodies against SaPIN2a failed to detect the presence of SaPIN2a protein. Despite an absence of significant inhibitory activity against bovine trypsin and chymotrypsin in extracts from transgenic lettuce, the endogenous trypsin-like activity in all transgenic lines analyzed was almost completely inhibited, and the endogenous chymotrypsin-like activity, moderately inhibited. Preliminary insect bioassays with $R_0$ transgenic plants showed that some of them acquired enhanced resistance to cabbage looper (*Trichoplusia ni*).

Hence, the heterologous expression of a plant PI, SaPIN2a, not only confers insect-resistance in transgenic lettuce but also inhibits the endogenous trypsin- and chymotrypsin-like activities. Since it has been recently shown that the yield and quality of antibodies produced in transgenic plants are significantly affected by endogenous proteolytic degradation (Stevens et al., 2000, *Plant Physiol* 124(1):173–82), heterologous expression of PIs could be exploited in the protection of heterologous protein production in transgenic plants.

The significant inhibition of trypsin-like activity and the moderate inhibition of chymptrypsin-like activity in transgenic lettuce, resulting from the expression of SaPIN2a, could not be due to a mutation caused by the T-DNA insertion because all three independent lines (TL1, 11 and 33) tested show similar inhibition. This finding suggests that other than a possible role in plant defense, SaPIN2a has an endogenous role in regulating the activity of endogenous proteases in the phloem (Xu et al., 2001, *Plant Mol. Biol.* 47: 727–738). The observations on lack of accumulation of transgene protein despite over-expression of corresponding mRNA have also been reported in transgenic petunia (Jones et al., 1985), tobacco (Jones et al., 1985, *EMBO. J.* 4:2411–2418; Florack et al., 1994, *Plant Mol. Biol.* 24:83–96), tomato (Seymour et al., 1993, *Plant Mol. Biol.* 23:1–9), cauliflower (Passelegue et al., 1996, *Plant Sci.* 113:79–89) and potato (Gatehouse et al., 1997, *Molecular Breeding* 3:49–63). Results of shorter transcripts other than that expected of the SaPIN2a mRNA using the NOS-terminator in transgenic lettuce suggests that the mRNA may not have undergone proper processing and could have been further degraded. Inadvertently, this may be a contributing factor to the failure in the detection of SaPIN2a protein in transgenic lettuce on western blot analysis, despite high accumulation of the SaPIN2a mRNA.

Whether SaPIN2a and SaPIN2b possess the putative inhibitory activity towards bovine trypsin and chymotrypsin, based on its sequence homology to known PIN2s, is still unclear. One possibility is that the amount of SaPIN2a protein accumulated in leaves of transgenic lettuce is not sufficient, as indicated by western blot analysis, for in vitro inhibitory activity assay using bovine trypsin or chymotrypsin, although this amount of SaPIN2a protein is sufficient for inhibiting endogenous trypsin-like activity in lettuce leaves. An alternative explanation is that SaPIN2a is specific to certain plant endogenous proteases and/or the midgut proteases from cabbage looper larvae, but not to bovine trypsin and chymotrypsin. It was found that the *Tribolium*-protease inhibitors from soybean (Birk et al., 1963, *Biochim. Biophys. Acta.* 67:326–328) and wheat (Applebaum and Konijn, 1966, *J. Insect Physiol.* 12:665–669) could markedly inhibit larval gut proteolysis of *Tribolium castaneum* but were inactive towards either mammalian trypsin or chymotrypsin. The maize proteinase inhibitor (MPI), belonging to the potato proteinase inhibitor I (PIN1) family based on its sequence homology to known PIN1s (Cordero et al., 1994, *Plant J.* 6:141–150), has been shown to effectively inhibit midgut chymotrypsin from *S. littoralis* larvae, but it only weakly inhibits bovine chymotrypsin, unlike most members of PIN1 family which are potent inhibitors of mammalian chymotrypsin (Tamayo et al., 2000, *Planta* 211:62–71).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

Plasmid vectors pSa7 and pMLVHisA were deposited with China Center for Type Culture Collection (CCTCC) at Wuhan University, Wuhan 430072 in China on Jun. 9, 2005 and Jul. 25, 2005, respectively, in accordance with the Budapest Treaty on the Deposit of Microorganisms, and accorded accession Nos. CCTCC M 205062 and CCTCC M 205084, respectively, which are incorporated herein by reference in their entireties. These plasmid vectors are described, for example, in Section 6.1, supra.

What is claimed is:

1. An isolated proteinase inhibitor II nucleic acid molecule comprising the nucleotide sequence of SEQ ID NO:1, or a nucleotide sequence that encodes the amino acid sequence of SEQ ID NO:2.

2. A method for producing a transformed plant comprising: (i) transforming a plant with a polynucleotide that comprises the nucleotide sequence of SEQ ID NO:1 or encodes the amino acid sequence of SEQ ID NO:2; and (ii) selecting a transformed plant in which said nucleotide sequence is expressed.

3. The method of claim 2, wherein said transforming is by nuclear transformation.

4. The method of claim 2, wherein said transforming is by plastid transformation.

5. The method of any of claim 2, wherein an endogenous proteinase activity of the transformed plant is inhibited.

6. The method of claim 5, wherein the endogenous protease activity is a trypsin-like activity or chymotrypsin-like activity.

7. A method for inhibiting programmed cell death and senescence in a transformed plant or plant part comprising: (i) transforming a plant with a polynucleotide that comprises the nucleotide sequence of SEQ ID NO:1 or encodes the amino acid sequence of SEQ ID NO:2; and (ii) selecting a transformed plant in which said polynucleotide is expressed.

8. The method of claim 7, wherein said transforming is by nuclear transformation.

9. The method of claim 7, wherein said transforming is by plastid transformation.

10. The method of claim 7, wherein an endogenous proteinase activity of the transformed plant is inhibited.

11. The method of claim 10, wherein the endogenous proteinase activity is a trypsin-like activity or chymotrypsin-like activity.

12. A method for producing a heterologous protein in a plant comprising: (i) transforming a plant with a first polynucleotide that comprises the nucleotide sequence of SEQ ID NO:1, or encodes the amino acid sequence of SEQ ID NO:2; (ii) transforming the plant with a second polynucleotide that encodes a heterologous protein; and (iii) isolating said heterologous protein.

13. The method of claim 12, wherein said transforming is by nuclear transformation.

14. The method of claim 12, wherein said transforming is by plastid transformation.

15. A transformed plant produced by the steps of:
(i) transforming a plant with a recombinant vector comprising a polynucleotide that comprises the nucleotide sequence of SEQ ID NO:1 or encodes the amino acid sequence of SEQ ID NO:2; and (ii) selecting a transformed plant in which said polynucleotide is expressed.

16. The transformed plant of claim 15, which is a transgenic plant.

17. The transformed plant of claim 15, which is a transplastomic plant.

18. A transformed plant comprising a polynucleotide that comprises the nucleotide sequence of SEQ ID NO:1 or encodes the amino acid sequence of SEQ ID NO:2.

19. The transformed plant of claim 18, which is a transgenic plant.

20. The transformed plant of claim 18, which is a transplastomic plant.

21. The transformed plant of any one of claims 15–17 or 18–20, wherein the plant is a leafy vegetable crop.

22. The transformed plant of claim 21, wherein the crop is lettuce.

23. The transformed plant of claim 22, wherein an endogenous proteinase activity of the transformed lettuce is inhibited.

24. The transformed plant of claim 23, wherein the endogenous proteinase activity is a trypsin-like activity or chymotrypsin-like activity.

25. A transgenic lettuce comprising cells that comprise pSa7.

26. A transplastomic tobacco comprising cells that comprise pMLVHisP.

27. A recombinant vector comprising: a polynucleotide that comprises the nucleotide sequence of SEQ ID NO:1 or encodes the amino acid sequence of SEQ ID NO:2.

28. The recombinant vector of claim 27, further comprising one or more regulatory elements operatively linked to said polynucleotide.

29. The recombinant vector of claim 28, wherein the regulatory element is 35S promoter of cauliflower mosaic virus (CaMV 35S).

30. A recombinant vector which is pSa7.

31. A recombinant vector which is pMLVHisP.

32. A recombinant cell comprising-the recombinant vector of claim 27.

33. The recombinant cell of claim 32, wherein the cell is a plant cell.

34. The recombinant cell of claim 33, wherein the plant cell is from a plant selected from the group consisting of tomatoes, ginger, scallions, water chestnuts, pepper, eggplant, lettuce, spinach, broccoli, brussels sprouts, calabrese, kale, cauliflower, red cabbage, white cabbage, cucumber, melon, watermelon, zucchini, squash, peas, beans, sweetcorn, carrots, onions, berries, grapes, banana, pineapple, rosaceous fruit and nut crops, tobacco, mango and papaya.

35. The recombinant cell of claim 33, wherein the plant cell is from a plant selected from the group consisting of *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum, Vicia, Vitis, Vigna,* and *Zea*.

\* \* \* \* \*

SEQUENCE LISTING

<160> NUMBER OF SEQ ID NOS: 14

<210> SEQ ID NO 1
<211> LENGTH: 529
<212> TYPE: DNA
<213> ORGANISM: Solanum americanum

<400> SEQUENCE: 1

```
cataatggct gttcacaaag ttagcttcct tgcttgccta cttgttcttg gatggatgtt      60
tctacttgcg aaacatgttg atgccaaggc ttgtactaga gaatgtggtc attttagcta     120
tggcatatgc ccacgttcag aaggaagtcc ccaaaaacct atatgcacca attgttgctc     180
aggctataag ggttgcaact attacagtgc taaaggagat ttgatttgtg aaggagaatc     240
tgaccctaga aacccaaaag attgtaccatt cgaatgtgat acacagattg cttattcaaa    300
atgtcctcgt tcagaaggaa agatgataat taaacccact ggatgcacca cttgttgcac     360
gggctatcag ggttgctact atttcgatca agatggtgat tttgtctgtg aaggagagag     420
tcctgaaccc aagaccactg cttatttcta atcaatcata tgttgttatc tatcaaaaaa     480
aaatatgtat gcatgatata tgctggttac tgtaatgtgg actttattg                529
```

<210> SEQ ID NO 2
<211> LENGTH: 148
<212> TYPE: PRT
<213> ORGANISM: Solanum americanum

<400> SEQUENCE: 2

```
Met Ala Val His Lys Val Ser Phe Leu Ala Cys Leu Leu Val Leu Gly
1               5                   10                  15

Trp Met Phe Leu Leu Ala Lys His Val Asp Ala Lys Ala Cys Thr Arg
            20                  25                  30

Glu Cys Gly His Phe Ser Tyr Gly Ile Cys Pro Arg Ser Glu Gly Ser
        35                  40                  45

Pro Gln Lys Pro Ile Cys Thr Asn Cys Cys Ser Gly Tyr Lys Gly Cys
    50                  55                  60

Asn Tyr Tyr Ser Ala Lys Gly Asp Leu Ile Cys Glu Gly Glu Ser Asp
65                  70                  75                  80

Pro Arg Asn Pro Lys Asp Cys Thr Phe Glu Cys Asp Thr Gln Ile Ala
                85                  90                  95

Tyr Ser Lys Cys Pro Arg Ser Glu Gly Lys Met Ile Ile Lys Pro Thr
            100                 105                 110
```

```
Gly Cys Thr Thr Cys Cys Thr Gly Tyr Gln Gly Cys Tyr Tyr Phe Asp
            115                 120                 125

Gln Asp Gly Asp Phe Val Cys Glu Gly Glu Ser Pro Glu Pro Lys Thr
    130                 135                 140

Thr Ala Tyr Phe
145

<210> SEQ ID NO 3
<211> LENGTH: 692
<212> TYPE: DNA
<213> ORGANISM: Solanum americanum

<400> SEQUENCE: 3
gaagataatt aatcacgatc gagaaagaat aaatggctgt tcacaaagaa gttagttccc      60
ttgcttacct acttgttctt ggattaatgt ttctacatgt aagcgcggta aaacatgttg     120
atgccaagcc atgtacaaga gaatgtggta atcttgggta tggaatatgc ccgcgttcag     180
aaggaagtcc ggaaaatccc atatgcacga attgttgctc aggctataaa ggttgcaact     240
attatagtgc taatgggact tttatttgcg aaggaagttc tgaccctaaa acccaaata     300 cttgccccctt atttttgtgat ggagatattg cctattcaaa atgtccccgt tcagaaggag     360
agactataat atatcccacg ggatgcacca cctgttgcac ggggtacaag ggttgctact     420
attttagtaa agaaggtgag tttgtgtgtg aaggagagag tgatgaaccc aacgttattt     480
ctaatcaatg aaatgcgttg tagttttttaa tataatgtat gaaataaaag tatgcagtac     540
ggcaatatat gataatcact atagtgtggg catcacagtt gtgctttata tgtaattact     600
aattatctga ataagagaaa aagatcatcc atgaggactt ggctcctctc cagtagtggt     660
gatctccttc ctaaaaaaaa aaaaaaaaaa aa                                    692

<210> SEQ ID NO 4
<211> LENGTH: 152
<212> TYPE: PRT
<213> ORGANISM: Solanum americanum

<400> SEQUENCE: 4

Met Ala Val His Lys Glu Val Ser Ser Leu Ala Tyr Leu Leu Val Leu
1               5                   10                  15

Gly Leu Met Phe Leu His Val Ser Ala Val Lys His Val Asp Ala Lys
            20                  25                  30

Pro Cys Thr Arg Glu Cys Gly Asn Leu Gly Tyr Gly Ile Cys Pro Arg
        35                  40                  45

Ser Glu Gly Ser Pro Glu Asn Pro Ile Cys Thr Asn Cys Cys Ser Gly
    50                  55                  60

Tyr Lys Gly Cys Asn Tyr Tyr Ser Ala Asn Gly Thr Phe Ile Cys Glu
65                  70                  75                  80

Gly Ser Ser Asp Pro Lys Asn Pro Asn Thr Cys Pro Leu Phe Cys Asp
                85                  90                  95

Gly Asp Ile Ala Tyr Ser Lys Cys Pro Arg Ser Glu Gly Glu Thr Ile
            100                 105                 110

Ile Tyr Pro Thr Gly Cys Thr Thr Cys Cys Thr Gly Tyr Lys Gly Cys
        115                 120                 125

Tyr Tyr Phe Ser Lys Glu Gly Glu Phe Val Cys Glu Gly Glu Ser Asp
    130                 135                 140

Glu Pro Asn Val Ile Ser Asn Gln
145                 150
```

<210> SEQ ID NO 5
<211> LENGTH: 26
<212> TYPE: DNA
<213> ORGANISM: Solanum americanum

<400> SEQUENCE: 5
ctccatcaca aaataagggg caagta                                      26

<210> SEQ ID NO 6
<211> LENGTH: 21
<212> TYPE: DNA
<213> ORGANISM: artificial
<220> FEATURE:
<223> OTHER INFORMATION: Description of artificial sequence: primer

<400> SEQUENCE: 6
gctcgaagac gatcagatac c                                           21

<210> SEQ ID NO 7
<211> LENGTH: 21
<212> TYPE: DNA
<213> ORGANISM: artificial
<220> FEATURE:
<223> OTHER INFORMATION: Description of artificial sequence: primer

<400> SEQUENCE: 7
agaaagagct ctcagtctgt c                                           21

<210> SEQ ID NO 8
<211> LENGTH: 11
<212> TYPE: PRT
<213> ORGANISM: artificial
<220> FEATURE:
<223> OTHER INFORMATION: Description of artificial sequence: Amino Acids
      77-87 of SaPIN2a

<400> SEQUENCE: 8

Gly Glu Ser Asp Pro Arg Asn Pro Lys Asp Cys
1               5                   10

<210> SEQ ID NO 9
<211> LENGTH: 14
<212> TYPE: PRT
<213> ORGANISM: artificial
<220> FEATURE:
<223> OTHER INFORMATION: Description of artificial sequence: Amino Acids
      139-152 of SaPIN2a

<400> SEQUENCE: 9

Cys Glu Gly Glu Ser Asp Glu Pro Asn Val Ile Ser Asn Gln
1               5                   10

<210> SEQ ID NO 10
<211> LENGTH: 25
<212> TYPE: DNA
<213> ORGANISM: artificial
<220> FEATURE:
<223> OTHER INFORMATION: Description of artificial sequence: primer

<400> SEQUENCE: 10
caatcccact atccttcgca agacc                                       25

<210> SEQ ID NO 11
<211> LENGTH: 29
<212> TYPE: DNA

```
<213> ORGANISM: artificial
<220> FEATURE:
<223> OTHER INFORMATION: Description of artificial sequence: primer

<400> SEQUENCE: 11
gtctatatta tactgttaaa taacaagcc                                    29

<210> SEQ ID NO 12
<211> LENGTH: 56
<212> TYPE: DNA
<213> ORGANISM: artificial
<220> FEATURE:
<223> OTHER INFORMATION: Description of artificial sequence: primer

<400> SEQUENCE: 12
gagaatccac catggctcat catcatcatc atcatatggc tgttcacaaa gttagc      56

<210> SEQ ID NO 13
<211> LENGTH: 27
<212> TYPE: DNA
<213> ORGANISM: artificial
<220> FEATURE:
<223> OTHER INFORMATION: Description of artificial sequence: primer

<400> SEQUENCE: 13
gagcggccgc ttagaaataa gcagtgg                                      27

<210> SEQ ID NO 14
<211> LENGTH: 21
<212> TYPE: DNA
<213> ORGANISM: artificial
<220> FEATURE:
<223> OTHER INFORMATION: Description of artificial sequence: primer

<400> SEQUENCE: 14
cgatacttcg gcgataaccg c                                            21
```